United States Patent
Llovet et al.

(10) Patent No.: US 8,030,013 B2
(45) Date of Patent: Oct. 4, 2011

(54) METHODS AND COMPOSITIONS FOR THE DIAGNOSIS FOR EARLY HEPATOCELLULAR CARCINOMA

(75) Inventors: Josep M. Llovet, New York, NY (US); Scott L. Friedman, Scarsdale, NY (US); Myron Schwartz, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 11/735,402

(22) Filed: Apr. 13, 2007

(65) Prior Publication Data

US 2008/0038736 A1 Feb. 14, 2008

Related U.S. Application Data

(60) Provisional application No. 60/792,166, filed on Apr. 14, 2006.

(51) Int. Cl.
*C12Q 1/68* (2006.01)
*G01N 33/50* (2006.01)
(52) U.S. Cl. ..................................................... 435/7.23
(58) Field of Classification Search .................. 435/7.23
See application file for complete search history.

(56) References Cited

U.S. PATENT DOCUMENTS

2009/0035290 A1 * 2/2009 Chen et al. .................. 424/94.5

FOREIGN PATENT DOCUMENTS

WO   WO2004/108964   * 12/2004

OTHER PUBLICATIONS

Ikeguchi et al. (Clin. Can. Res. 8:3131-3136 (2002).*
Ikeguchi et al. (Cancer 95(9):1938-1345 (2002)).*
Colombat et al. (J. Pathol 201:260-267 (2003)).*
Lencioni et al., J. Hepatol., 40:162-171 (2004).*

* cited by examiner

*Primary Examiner* — Lynn Bristol
(74) *Attorney, Agent, or Firm* — Marshall, Gerstein & Borun LLP

(57) ABSTRACT

Methods and compositions are provide to allow discrimination of dysplastic nodules from early HCC nodules. More specifically, it has been determined that TERT, GPC3, gankyrin, survivin, TOP2A, LYVE1, Ecadherin, IGFBP3, PDGFRA, TGFA, cyclin D1 and HGF are differentially expressed in HCC as compared to normal liver cells and liver cells that have dysplastic, non-cancerous nodules.

17 Claims, 10 Drawing Sheets

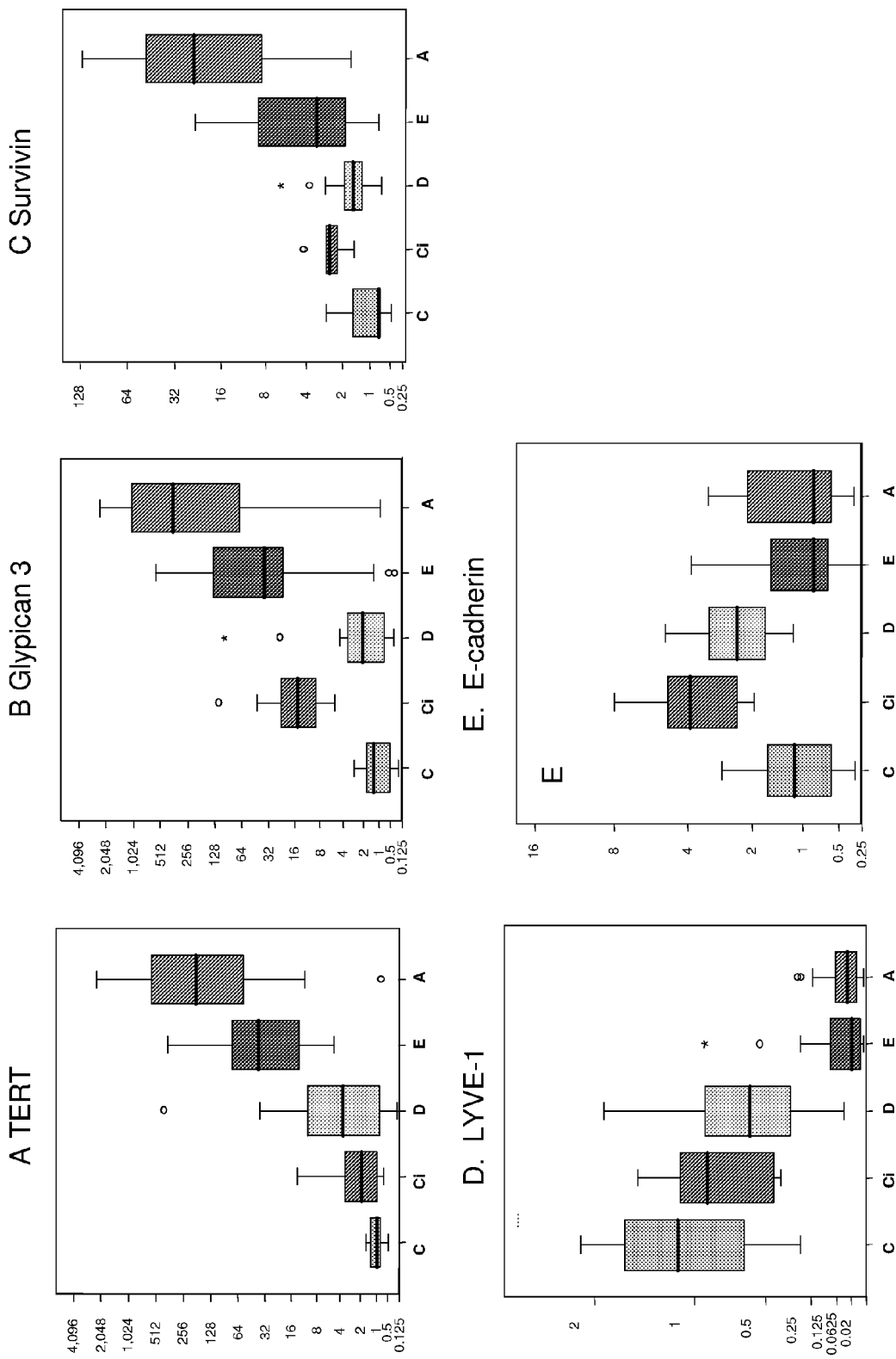
Figure 4A-E

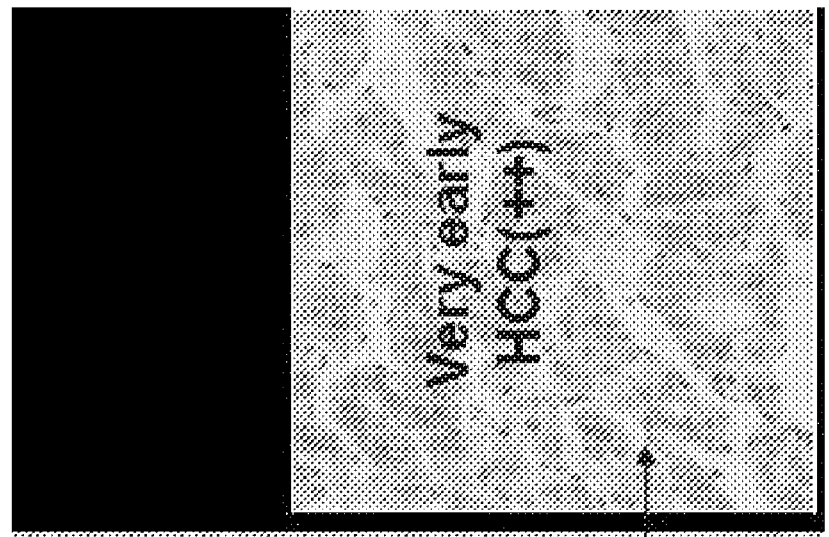
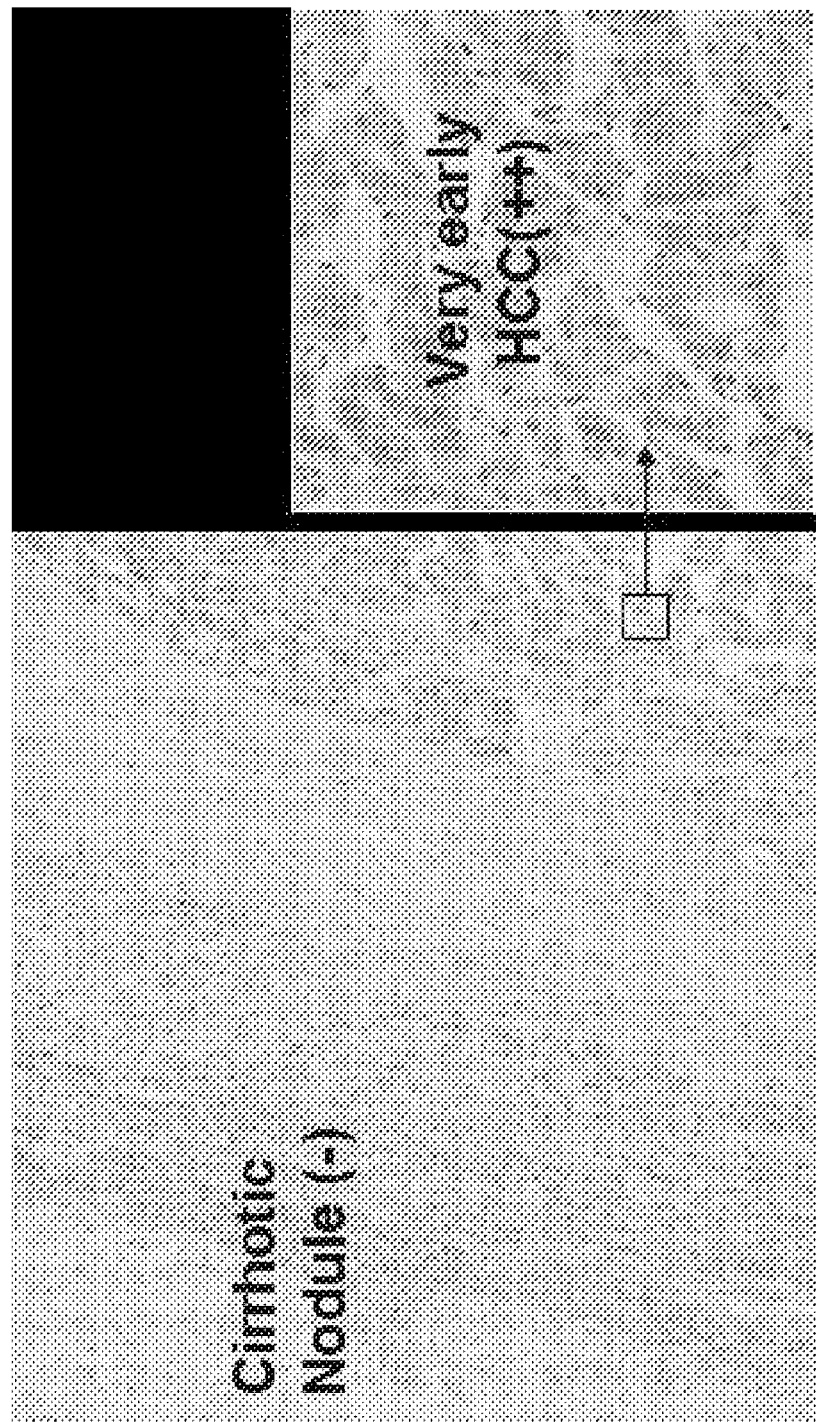
Figure 5A
Figure 5B

Glypican-3 staining in dysplastic nodule (x400)

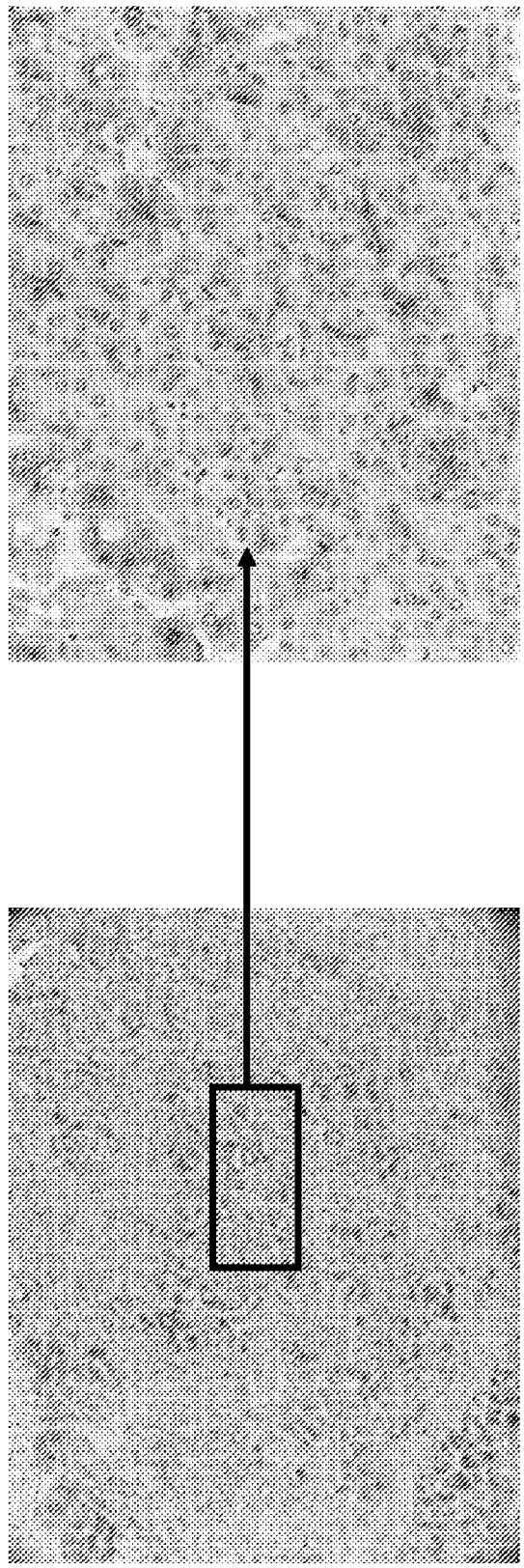

Glypican-3 staining in cirrhotic tissue (x 400)

Glypican-3 staining in cirrhotic tissue (x 100)

```
                        SEQUENCE LISTING

<160> NUMBER OF SEQ ID NOS: 24

<210> SEQ ID NO 1
<211> LENGTH: 4015
<212> TYPE: DNA
<213> ORGANISM: Homo sapiens

<400> SEQUENCE: 1
gcagcgctgc gtcctgctgc gcacgtggga agccctggcc ccggccaccc ccgcgatgcc      60
gcgcgctccc cgctgccgag ccgtgcgctc cctgctgcgc agccactacc gcgaggtgct     120
gccgctggcc acgttcgtgc ggcgcctggg gccccagggc tggcggctgg tgcagcgcgg     180
ggacccggcg gctttccgcg cgctggtggc ccagtgcctg gtgtgcgtgc cctgggacgc     240
acggccgccc ccgccgccc cctccttccg ccaggtgtcc tgcctgaagg agctggtggc     300
ccgagtgctg cagaggctgt gcgagcgcgg cgcgaagaac gtgctggcct tcggcttcgc     360
gctgctggac ggggcccgcg ggggcccccc cgaggccttc accaccagcg tgcgcagcta     420
cctgcccaac acggtgaccg acgcactgcg ggggagcggg gcgtgggggc tgctgctgcg     480
ccgcgtgggc gacgacgtgc tggttcacct gctggcacgc tgcgcgctct ttgtgctggt     540
ggctcccagc tgcgcctacc aggtgtgcgg gccgccgctg taccagctcg gcgctgccac     600
tcaggcccgg ccccgccac acgctagtgg accccgaagg cgtctgggat gcgaacgggc     660
ctggaaccat agcgtcaggg aggccggggt cccctgggc ctgccagccc cgggtgcgag     720
gaggcgcggg ggcagtgcca gccgaagtct gccgttgccc aagaggccca ggcgtggcgc     780 tgccctgag ccgagcgga cgcccgttgg gcagggggtcc tgggcccacc cgggcaggac     840
gcgtggaccg agtgaccgtg gtttctgtgt ggtgtcacct gccagacccg ccgaagaagc     900
cacctctttg gagggtgcgc tctctggcac gcgccactcc cacccatccg tgggccgcca     960
gcaccacgcg ggccccccat ccacatcgcg gccaccacgt ccctgggaca cgccttgtcc    1020
```

```
cccggtgtac gccgagacca agcacttcct ctactcctca ggcgacaagg agcagctgcg    1080
gccctccttc ctactcagct ctctgaggcc cagcctgact ggcgctcgga ggctcgtgga    1140
gaccatcttt ctgggttcca ggccctggat gccagggact cccgcaggt tgccccgcct     1200
gccccagcgc tactggcaaa tgcggcccct gtttctggag ctgcttggga accacgcgca    1260
gtgcccctac ggggtgctcc tcaagacgca ctgcccgctg cgagctgcgg tcaccccagc    1320
agccggtgtc tgtgcccggg agaagcccca gggctctgtg gcggccccg aggaggagga    1380
cacagacccc cgtcgcctgg tgcagctgct ccgccagcac agcagcccct ggcaggtgta    1440
cggcttcgtg cgggcctgcc tgcgccggct ggtgccccca ggcctctggg gctccaggca    1500
caacgaacgc cgcttcctca ggaacaccaa gaagttcatc tccctgggga agcatgccaa    1560
gctctcgctg caggagctga cgtggaagat gagcgtgcgg gactgcgctt ggctgcgcag    1620
gagcccaggg gttggctgtg ttccggccgc agagcaccgt ctgcgtgagg agatcctggc    1680
caagttcctg cactggctga tgagtgtgta cgtcgtcgag ctgctcaggt ctttcttta     1740
tgtcacggag accacgtttc aaaagaacag gctctttttc taccggaaga gtgtctggag    1800
caagttgcaa agcattggaa tcagacagca cttgaagagg gtgcagctgc gggagctgtc    1860
ggaagcagag gtcaggcagc atcgggaagc caggcccgcc ctgctgacgt ccagactccg    1920
cttcatcccc aagcctgacg ggctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcgcg ccccggcctc ctgggcgcct ctgtgctggg     2100
cctggacgat atccacaggg cctggcgcac cttcgtgctg cgtgtgcggg cccaggaccc    2160
gccgcctgag ctgtactttg tcaaggtgga tgtgacgggc gcgtacgaca ccatccccca    2220
ggacaggctc acggaggtca tcgccagcat catcaaaccc cagaacacgt actgcgtgcg    2280
tcggtatgcc gtggtccaga aggccgccca tgggcacgtc cgcaaggcct tcaagagcca    2340
cgtctctacc ttgacagacc tccagccgta catgcgcaca ttcgtggctc acctgcagga    2400
gaccagcccg ctgagggatg ccgtcgtcat cgagcagagc tcctccctga atgaggccag    2460
cagtggcctc ttcgacgtct tcctacgctt catgtgccac cacgccgtgc gcatcagggg    2520
caagtcctac gtccagtgcc aggggatccc gcagggctcc atcctctcca cgctgctctg    2580
cagcctgtgc tacggcgaca tggagaacaa gctgtttgcg gggattcggc gggacgggct    2640
gctcctgcgt ttggtggatg atttcttgtt ggtgacacct cacctcaccc acgcgaaaac    2700
cttcctcagg accctggtcc gaggtgtccc tgagtatggc tgcgtggtga acttgcggaa    2760
gacagtggtg aacttcccct agaagacga ggccctgggt ggcacggctt tgttcagat      2820
gccggcccac ggcctattcc cctggtgcgg cctgctgctg atacccgga ccctggaggt     2880
gcagagcgac tactccagct atgcccggac ctccatcaga gccagtctca ccttcaaccg    2940
cggcttcaag gctgggagga acatgcgtcg caaactcttt ggggtcttgc ggctgaagtg    3000
tcacagcctg tttctggatt tgcaggtgaa cagcctccag acggtgtgca ccaacatcta    3060
caagatcctc ctgctgcagg cgtacaggtt tcacgcatgt gtgctgcagc tcccattca     3120
tcagcaagtt tggaagaacc ccacatttt cctgcgcgtc atctctgaca cggcctccct    3180
ctgctactcc atcctgaaag ccaagaacgc agggatgtcg ctgggggcca agggcgccgc    3240
cggccctctg ccctccgagg ccgtgcagtg gctgtgccac caagcattcc tgctcaagct    3300
gactcgacac cgtgtcacct acgtgccact cctgggtgca ctcaggacag cccagacgca    3360
gctgagtcgg aagctcccgg ggacgacgct gactgccctg gaggccgcag ccaacccggc    3420
```

| | |
|---|---|
| actgccctca gacttcaaga ccatcctgga ctgatggcca cccgcccaca gccaggccga | 3480 |
| gagcagacac cagcagccct gtcacgccgg gctctacgtc caggagggg aggggcggcc | 3540 |
| cacacccagg cccgcaccgc tgggagtctg aggcctgagt gagtgtttgg ccgaggcctg | 3600 |
| catgtccggc tgaaggctga gtgtccggct gaggcctgag cgagtgtcca gccaagggct | 3660 |
| gagtgtccag cacacctgcc gtcttcactt ccccacaggc tggcgctcgg ctccacccca | 3720 |
| gggccagctt ttcctcacca ggagcccggc ttcactcccc acataggaa tagtccatcc | 3780 |
| ccagattcgc cattgttcac ccctcgccct gccctccttt gccttccacc cccaccatcc | 3840 |
| aggtggagac cctgagaagg accctgggag ctctgggaat ttggagtgac caaaggtgtg | 3900 |
| ccctgtacac aggcgaggac cctgcacctg gatggggtc cctgtgggtc aaattggggg | 3960 |
| gaggtgctgt gggagtaaaa tactgaatat atgagttttt cagttttgaa aaaaa | 4015 |

<210> SEQ ID NO 2
<211> LENGTH: 2382
<212> TYPE: DNA
<213> ORGANISM: Homo sapiens

<400> SEQUENCE: 2

| | |
|---|---|
| ccctgccccg cgccgccaag cggttcccgc cctcgcccag cgcccaggta gctgcgagga | 60 |
| aacttttgca gcggctgggt agcagcacgt ctcttgctcc tcagggccac tgccaggctt | 120 |
| gccgagtcct gggactgctc tcgctccggc tgccactctc ccgcgctctc ctagctccct | 180 |
| gcgaagcagg atggccggga ccgtgcgcac cgcgtgcttg gtggtggcga tgctgctcag | 240 |
| cttggacttc ccgggacagg cgcagccccc gccgccgccg ccggacgcca cctgtcacca | 300 |
| agtccgctcc ttcttccaga gactgcagcc cggactcaag tgggtgccag aaactcccgt | 360 |
| gccaggatca gatttgcaag tatgtctccc taagggccca acatgctgct caagaaagat | 420 |
| ggaagaaaaa taccaactaa cagcacgatt gaacatggaa cagctgcttc agtctgcaag | 480 |
| tatggagctc aagttcttaa ttattcagaa tgctgcggtt ttccaagagg cctttgaaat | 540 |
| tgttgttcgc catgccaaga actacaccaa tgccatgttc aagaacaact acccaagcct | 600 |
| gactccacaa gcttttgagt ttgtgggtga attttcaca gatgtgtctc tctacatctt | 660 |
| gggttctgac atcaatgtag atgacatggt caatgaattg tttgacagcc tgtttccagt | 720 |
| catctatacc cagctaatga acccaggcct gcctgattca gccttggaca tcaatgagtg | 780 |
| cctccgagga gcaagacgtg acctgaaagt atttgggaat tcccccaagc ttattatgac | 840 |
| ccaggtttcc aagtcactgc aagtcactag gatcttcctt caggtctga atcttggaat | 900 |
| tgaagtgatc aacacaactg atcacctgaa gttcagtaag gactgtggcc gaatgctcac | 960 |
| cagaatgtgg tactgctctt actgccaggg actgatgatg gttaaaccct gtggcggtta | 1020 |
| ctgcaatgtg gtcatgcaag gctgtatggc aggtgtggtg gagattgaca gtactggag | 1080 |
| agaatacatt ctgtcccttg aagaacttgt gaatggcatg tacagaatct atgacatgga | 1140 |
| gaacgtactg cttggtctct tttcaacaat ccatgattct atccagtatg tccagaagaa | 1200 |
| tgcaggaaag ctgaccacca ctattggcaa gttatgtgcc cattctcaac aacgccaata | 1260 |
| tagatctgct tattatcctg aagatctctt tattgacaag aaagtattaa agttgctca | 1320 |
| tgtagaacat gaagaaacct tatccagccg aagaagggaa ctaattcaga agttgaagtc | 1380 |
| tttcatcagc ttctatagtg cttttgcctgg ctacatctgc agccatagcc ctgtggcgga | 1440 |
| aaacgacacc ctttgctgga atggacaaga actcgtggag agatacagcc aaaaggcagc | 1500 |
| aaggaatgga atgaaaaacc agttcaatct ccatgagctg aaaatgaagg ccctgagcc | 1560 |

| | |
|---|---|
| agtggtcagt caaattattg acaaactgaa gcacattaac cagctcctga gaaccatgtc | 1620 |
| tatgcccaaa ggtagagttc tggataaaaa cctggatgag gaagggtttg aaagtggaga | 1680 |
| ctgcggtgat gatgaagatg agtgcattgg aggctctggt gatggaatga taaaagtgaa | 1740 |
| gaatcagctc cgcttccttg cagaactggc ctatgatctg gatgtggatg atgcgcctgg | 1800 |
| aaacagtcag caggcaactc cgaaggacaa cgagataagc acctttcaca acctcgggaa | 1860 |
| cgttcattcc ccgctgaagc ttctcaccag catggccatc tcggtggtgt gcttcttctt | 1920 |
| cctggtgcac tgactgcctg gtgcccagca catgtgctgc cctacagcac cctgtggtct | 1980 |
| tcctcgataa agggaaccac tttcttattt ttttctattt ttttttttttt gttatcctgt | 2040 |
| atacctcctc cagccatgaa gtagaggact aaccatgtgt tatgttttcg aaaatcaaat | 2100 |
| ggtatctttt ggaggaagat acattttagt ggtagcatat agattgtcct tttgcaaaga | 2160 |
| aagaaaaaaa accatcaagt tgtgccaaat tattctccta tgtttggctg ctagaacatg | 2220 |
| gttaccatgt ctttctctct cactcccctcc cttttctatcg ttctctcttt gcatggattt | 2280 |
| ctttgaaaaa aaataaattg ctcaaataaa aaaaaaaaaa aaaaaaaaaa aaaaaaaaaa | 2340 |
| aaaaaaaaaa aaaaaaaaaa aaaaaaaaaa aaaaaaaaaa aa | 2382 |

<210> SEQ ID NO 3
<211> LENGTH: 1467
<212> TYPE: DNA
<213> ORGANISM: Homo sapiens

<400> SEQUENCE: 3

| | |
|---|---|
| attggtgaag ctctaacggc tgttttgact ggcgtagccg gagccggcga cgtgaggcgg | 60 |
| gcgttgctcg cgcgacaagt agttgctggg acagcgaaat ggaggggtgt gtgtctaacc | 120 |
| taatggtctg caacctggcc tacagcggga agctggaaga gttgaaggag agtattctgg | 180 |
| ccgataaatc cctggctact agaactgacc aggacagcag aactgcattg cactgggcat | 240 |
| gctcagctgg acatacagaa attgttgaat ttttgttgca acttggagtg ccagtgaatg | 300 |
| ataaagacga tgcaggttgg tctcctcttc atattgcggc ttctgctggc cgggatgaga | 360 |
| ttgtaaaagc ccttctggga aaaggtgctc aagtgaatgc tgtcaatcaa atggctgta | 420 |
| ctcccttaca ttatgcagct tcgaaaaaca ggcatgagat cgctgtcatg ttactggaag | 480 |
| gcggggctaa tccagatgct aaggaccatt atgaggctac agcaatgcac cgggcagcag | 540 |
| ccaaggacac ttagcctgtg atgaggagag agtggaagaa gcaaaactgc tggtgtccca | 600 |
| aggagcaagt atttacattg agaataaaga agaaagaca cccctgcaag tggccaaagg | 660 |
| tggcctgggt ttaatactca agagaatggt ggaaggttaa acagcttgga tttattctta | 720 |
| cttttgtatgt tgtgttgttg tccccagtgt cctacaaact aatgtatttg tgcacaagac | 780 |
| atcatctatg aatgatgaag ttttctcacc ttcaaagtct tataaacatg ttgactcttg | 840 |
| ttcctgctga gttacttgtt cgaagcttac agcttgtttt ccaggcatcg aataactgtt | 900 |
| gagattgttc tactgttgtc gtatattctt ctatattgaa ttctggttaa tttggagtaa | 960 |
| ctaattctgt ggctgttgtg agtcttcagc accctcccat gtaccttata tccctctctg | 1020 |
| aaacagaaca gctccaatag caacaagcta gttgttctgc cagatgtttc tatgtggatt | 1080 |
| ctgtaatgtt cctccataca gttaaaacat cctaacttgt ttttcaagct cactcaggcc | 1140 |
| tacgccaaac gtttctgttt ttttaacca tgaggtttaa tttatttttg tgataggagg | 1200 |
| gatatttaca tattttagtg gaccacattt taagttggat ggtgtgctct aaaatactga | 1260 |
| aaaacaatag cccatatacc tatgtatttg ttttgatgg gttgtttact ctgaaataaa | 1320 |

| atgtatggtt tcttaaaag gaagttttaa agtacctatt tgtgtcatc ctgtattgaa | 1380 |
| aagaatgtca agcttgttaa aatgacatgt aacaaaaatg tattttgatt tgtatttcag | 1440 |
| aaactaaaaa ataaaatgtt gaaagaa | 1467 |

<210> SEQ ID NO 4
<211> LENGTH: 2655
<212> TYPE: DNA
<213> ORGANISM: Homo sapiens

<400> SEQUENCE: 4

| cccagaaggc cgcgggggt ggaccgccta agagggcgtg cgctcccgac atgccccgcg | 60 |
| gcgcgccatt aaccgccaga tttgaatcgc gggacccgtt ggcagaggtg cggcggcgg | 120 |
| catgggtgcc ccgacgttgc ccctgcctg cagccctttt ctcaaggacc accgcatctc | 180 |
| tacattcaag aactggccct tcttggaggg ctgcgcctgc accccggagc ggatggccga | 240 |
| ggctggcttc atccactgcc ccactgagaa cgagccagac ttggcccagt gtttcttctg | 300 |
| cttcaaggag ctggaaggct gggagccaga tgacgacccc atagaggaac ataaaaagca | 360 |
| ttcgtccggt tgcgctttcc tttctgtcaa gaagcagttt gaagaattaa cccttggtga | 420 |
| attttttgaaa ctggacagag aaagagccaa gaacaaaatt gcaaggaaa ccaacaataa | 480 |
| gaagaaagaa tttgaggaaa ctgcggagaa agtgcgccgt gccatcgagc agctggctgc | 540 |
| catggattga ggcctctggc cggagctgcc tggtcccaga gtggctgcac cacttccagg | 600 |
| gtttattccc tggtgccacc agccttcctg tgggcccctt agcaatgtct taggaaagga | 660 |
| gatcaacatt tcaaattag atgtttcaac tgtgctcttg ttttgtcttg aaagtggcac | 720 |
| cagaggtgct tctgcctgtg cagcgggtgc tgctggtaac agtggctgct tctctctctc | 780 |
| tctctctttt ttgggggctc attttttgctg ttttgattcc cgggcttacc aggtgagaag | 840 |
| tgagggagga agaaggcagt gtccccttttg ctagagctga cagcttttgtt cgcgtgggca | 900 |
| gagccttcca cagtgaatgt gtctggacct catgttgttg aggctgtcac agtcctgagt | 960 |
| gtggacttgg caggtgcctg ttgaatctga gctgcaggtt ccttatctgt cacacctgtg | 1020 |
| cctcctcaga ggacagtttt tttgttgttg tgttttttttg ttttttttt tttggtagat | 1080 |
| gcatgacttg tgtgtgatga gagaatggag acagagtccc tggctcctct actgtttaac | 1140 |
| aacatggctt tcttattttg tttgaattgt taattcacag aatagcacaa actacaatta | 1200 |
| aaactaagca caaagccatt ctaagtcatt ggggaaacgg ggtgaacttc aggtggatga | 1260 |
| ggagacagaa tagagtgata ggaagcgtct ggcagatact ccttttgcca ctgctgtgtg | 1320 |
| attagacagg cccagtgagc cgcggggcac atgctggccg ctcctccctc agaaaaaggc | 1380 |
| agtggcctaa atccttttta aatgacttgg ctcgatgctg tggggactg gctgggctgc | 1440 |
| tgcaggccgt gtgtctgtca gcccaacctt cacatctgtc acgttctcca cacggggag | 1500 |
| agacgcagtc cgcccaggtc cccgcttct ttggaggcag cagctcccgc agggctgaag | 1560 |
| tctggcgtaa gatgatggat ttgattcgcc ctcctccctg tcatagagct gcagggtgga | 1620 |
| ttgttacagc ttcgctggaa acctctggag gtcatctcgg ctgttcctga aaataaaaa | 1680 |
| gcctgtcatt tcaaacactg ctgtggaccc tactgggttt ttaaaatatt gtcagttttt | 1740 |
| catcgtcgtc cctagcctgc caacagccat ctgcccagac agccgcagtg aggatgagcg | 1800 |
| tcctggcaga gacgcagttg tctctgggcg cttgccagag ccacgaaccc cagacctgtt | 1860 |
| tgtatcatcc gggctccttc cgggcagaaa caactgaaaa tgcacttcag acccacttat | 1920 |
| ttctgccaca tctgagtcgg cctgagatag acttttccct ctaaactggg agaatatcac | 1980 |

| | |
|---|---|
| agtggttttt gttagcagaa aatgcactcc agcctctgta ctcatctaag ctgcttattt | 2040 |
| ttgatatttg tgtcagtctg taaatggata cttcacttta ataactgttg cttagtaatt | 2100 |
| ggctttgtag agaagctgga aaaaaatggt tttgtcttca actcctttgc atgccaggcg | 2160 |
| gtgatgtgga tctcggcttc tgtgagcctg tgctgtgggc agggctgagc tggagccgcc | 2220 |
| cctctcagcc cgcctgccac ggcctttcct taaaggccat ccttaaaacc agaccctcat | 2280 |
| ggctaccagc acctgaaagc ttcctcgaca tctgttaata aagccgtagg cccttgtcta | 2340 |
| agtgcaaccg cctagacttt cttttcagata catgtccaca tgtccatttt tcaggttctc | 2400 |
| taagttggag tggagtctgg aaggggttgt gaatgaggct tctgggctat gggtgaggtt | 2460 |
| ccaatggcag gttagagccc ctcgggccaa ctgccatcct ggaaagtaga gacagcagtg | 2520 |
| cccgctgccc agaagagacc agcaagccaa actggagccc ccattgcagg ctgtcgccat | 2580 |
| gtggaaagag taactcacaa ttgccaataa agtctcatgt ggttttatct aaaaaaaaaa | 2640 |
| aaaaaaaaaa aaaaa | 2655 |

<210> SEQ ID NO 5
<211> LENGTH: 5698
<212> TYPE: DNA
<213> ORGANISM: Homo sapiens

<400> SEQUENCE: 5

| | |
|---|---|
| aggttcaagt ggagctctcc taaccgacgc gcgtctgtgg agaagcggct tggtcggggg | 60 |
| tggtctcgtg gggtcctgcc tgtttagtcg cttttcaggggt tcttgagccc cttcacgacc | 120 |
| gtcaccatgg aagtgtcacc attgcagcct gtaaatgaaa atatgcaagt caacaaaata | 180 |
| aagaaaaatg aagatgctaa gaaaagactg tctgttgaaa gaatctatca aaagaaaaca | 240 |
| caattggaac atattttgct ccgcccagac acctacattg ttctgtgga attagtgacc | 300 |
| cagcaaatgt gggtttacga tgaagatgtt ggcattaact ataggggaagt cacttttgtt | 360 |
| cctggttttgt acaaaatctt tgatgagatt ctagttaatg ctgcggacaa caaacaaagg | 420 |
| gacccaaaaa tgtcttgtat tagagtcaca attgatccgg aaaacaattt aattagtata | 480 |
| tggaataatg gaaaaggtat tcctgttgtt gaacacaaag ttgaaaagat gtatgtccca | 540 |
| gctctcatat ttggacagct cctaactttct agtaactatg atgatgatga aagaaagtg | 600 |
| acaggtggtc gaaatggcta tggagccaaa ttgtgtaaca tattcagtac caaatttact | 660 |
| gtggaaacag ccagtagaga atacaagaaa atgttcaaac agacatggat ggataatatg | 720 |
| ggaagagctg tgagatgga actcaagccc ttcaatggag aagattatac atgtatcacc | 780 |
| tttcagcctg atttgtctaa gtttaaaatg caaagcctgg acaaagatat tgttgcacta | 840 |
| atggtcagaa gagcatatga tattgctgga tccaccaaag atgtcaaagt ctttcttaat | 900 |
| ggaaataaac tgccagtaaa aggatttcgt agttatgtgg acatgtattt gaaggacaag | 960 |
| ttggatgaaa ctggtaactc cttgaaagta atacatgaac aagtaaacca caggtgggaa | 1020 |
| gtgtgtttaa ctatgagtga aaaaggctttt cagcaaatta gctttgtcaa cagcattgct | 1080 |
| acatccaagg gtggcagaca tgttgattat gtagctgatc agattgtgac taaacttgtt | 1140 |
| gatgttgtga agaagaagaa caagggtggt gttgcagtaa aagcacatca ggtgaaaaat | 1200 |
| cacatgtgga ttttttgtaaa tgccttaatt gaaaacccaa cctttgactc tcagacaaaa | 1260 |
| gaaaacatga ctttacaacc caagagctttt ggatcaacat gccaattgag tgaaaaattt | 1320 |
| atcaaagctg ccattggctg tggtattgta gaaagcatac taaactgggt gaagtttaag | 1380 |
| gcccaagtcc agttaaacaa gaagtgttca gctgtaaaac ataatagaat caagggaatt | 1440 |

```
cccaaactcg atgatgccaa tgatgcaggg ggccgaaact ccactgagtg tacgcttatc      1500
ctgactgagg gagattcagc caaaactttg gctgtttcag gccttggtgt ggttgggaga      1560
gacaaatatg gggtttttccc tcttagagga aaaatactca atgttcgaga agcttctcat    1620
aagcagatca tggaaaatgc tgagattaac aatatcatca agattgtggg tcttcagtac     1680
aagaaaaact atgaagatga agattcattg aagacgcttc gttatgggaa gataatgatt     1740 atgcacagatc aggaccaaga tggttcccac atcaaaggct tgctgattaa ttttatccat   1800
cacaactggc cctctcttct gcgacatcgt tttctggagg aatttatcac tcccattgta     1860
aaggtatcta aaaacaagca agaaatggca ttttacagcc ttcctgaatt tgaagagtgg     1920
aagagttcta ctccaaatca taaaaaatgg aaagtcaaat attacaaagg tttgggcacc    1980
agcacatcaa aggaagctaa agaatacttt gcagatatga aaagacatcg tatccagttc    2040
aaatattctg gtcctgaaga tgatgctgct atcagcctgg cctttagcaa aaaacagata    2100
gatgatcgaa aggaatggtt aactaatttc atggaggata aagacaacg aaagttactt     2160 gggcttcctg aggattactt gtatggacaa actaccacat atctgacata taatgacttc    2220
atcaacaagg aacttatctt gttctcaaat tctgataacg agagatctat cccttctatg    2280
gtggatggtt tgaaaccagg tcagagaaag gttttgttta cttgcttcaa acggaatgac   2340
aagcgagaag taaaggttgc ccaattagct ggatcagtgg ctgaaatgtc ttcttatcat   2400
catggtgaga tgtcactaat gatgaccatt atcaatttgg ctcagaattt tgtgggtagc    2460
aataatctaa acctcttgca gcccattggt cagtttggta ccaggctaca tggtggcaag    2520
gattctgcta gtccacgata catctttaca atgctcagct ctttggctcg attgttattt   2580
ccaccaaaag atgatcacac gttgaagttt ttatatgatg acaaccagcg tgttgagcct    2640
gaatggtaca ttcctattat tcccatggtg ctgataaatg gtgctgaagg aatcggtact    2700
gggtggtcct gcaaaatccc caactttgat gtgcgtgaaa ttgtaaataa catcaggcgt   2760
ttgatggatg gagaagaacc tttgccaatg cttccaagtt acaagaactt caagggtact    2820
attgaagaac tggctccaaa tcaatatgtg attagtggtg aagtagctat tcttaattct    2880
acaaccattg aaatctcaga gcttcccgtc agaaacatgga cccagacata caagaacaa    2940 gttctagaac ccatgttgaa tggcaccgag aagacacctc ctctcataac agactatagg    3000
gaataccata cagataccac tgtgaaattt gttgtgaaga tgactgaaga aaaactggca    3060
gaggcagaga gagttggact acacaaagtc ttcaaactcc aaactagtct cacatgcaac    3120
tctatggtgc ttttttgacca cgtaggctgt ttaaagaaat atgacacggt gttggatatt   3180
ctaagagact ttttttgaact cagacttaaa tattatggat taagaaaaga atggctccta   3240
ggaatgcttg gtgctgaatc tgctaaactg aataatcagg ctcgctttat cttagagaaa    3300
atagatggca aaataatcat tgaaaataag cctaagaaag aattaattaa agttctgatt   3360 cagagggggat atgattcgga tcctgtgaag gcctggaaaa aagcccagca aaaggttcca    3420
gatgaagaag aaaatgaaga gagtgacaac gaaaaggaaa ctgaaaagag tgactccgta    3480
acagattctg gaccaacctt caactatctt cttgatatgc cccttttggta tttaaccaag    3540 gaaaagaaag atgaactctg caggctaaga aatgaaaaag aacaagagct ggacacatta    3600
aaaagaaaga gtccatcaga tttgtggaaa gaagacttgg ctacatttat tgaagaattg    3660
gaggctgttg aagccaagga aaaacaagat gaacaagtcg gacttcctgg gaaaggggggg   3720 aaggccaagg ggaaaaaaac acaaatggct gaagttttgc cttctccgcg tggtcaaaga    3780
gtcattccac gaataaccat agaaatgaaa gcagaggcag aaaagaaaaa taaaagaaa     3840
```

-continued

```
attaagaatg aaaatactga aggaagccct caagaagatg gtgtggaact agaaggccta      3900
aaacaaagat tagaaaagaa acagaaaaga gaaccaggta caaagacaaa gaaacaaact      3960
acattggcat ttaagccaat caaaaaagga aagaagagaa atccctggtc tgattcagaa      4020
tcagatagga gcagtgacga aagtaatttt gatgtccctc cacgagaaac agagccacgg      4080
agagcagcaa caaaaacaaa attcacaatg gatttggatt cagatgaaga tttctcagat      4140
tttgatgaaa aaactgatga tgaagatttt gtcccatcag atgctagtcc acctaagacc      4200
aaaacttccc caaaacttag taacaaagaa ctgaaccac agaaaagtgt cgtgtcagac       4260
cttgaagctg atgatgttaa gggcagtgta ccactgtctt caagcccctcc tgctacacat     4320 ttcccagatg aaactgaaat tacaaaccca gttcctaaaa agaatgtgac agtgaagaag      4380
acagcagcaa aaagtcagtc ttccacctcc actaccggtg ccaaaaaaag gctgccccca     4440
aaaggaacta aaagggatcc agctttgaat tctggtgtct ctcaaaagcc tgatcctgcc     4500
aaaaccaaga atcgccgcaa aaggaagcca tccacttctg atgattctga ctctaatttt     4560
gagaaaattg tttcgaaagc agtcacaagc aagaaatcca aggggagag tgatgacttc      4620 catatggact ttgactcagc tgtggctcct cgggcaaaat ctgtacgggc aaagaaacct     4680
ataaagtacc tggaagagtc agatgaagat gatctgtttt aaaatgtgag gcgattattt     4740
taagtaatta tcttaccaag cccaagactg gttttaaagt tacctgaagc tcttaacttc     4800
ctcccctctg aatttagttt ggggaaggtg tttttagtac aagacatcaa agtgaagtaa     4860
agcccaagtg ttctttagct ttttataata ctgtctaaat agtgaccatc tcatgggcat     4920
tgttttcttc tctgctttgt ctgtgttttg agtctgcttt cttttgtctt taaaacctga    4980
tttttaagtt cttctgaact gtagaaatag ctatctgatc acttcagcgt aaagcagtgt    5040
gtttattaac catccactaa gctaaaacta gagcagtttg atttaaaagt gtcactcttc    5100 ctcctttct actttcagta gatatgagat agagcataat tatctgtttt atcttagttt    5160
tatacataat ttaccatcag atagaacttt atggttctag tacagatact ctactacact    5220
cagcctctta tgtgccaagt ttttctttaa gcaatgagaa attgctcatg ttcttcatct    5280
tctcaaatca tcagaggcca aagaaaaaca ctttggctgt gtctataact tgacacagtc    5340
aatagaatga agaaaattag agtagttatg tgattatttc agctcttgac ctgtcccctc    5400
tggctgcctc tgagtctgaa tctcccaaag agagaaacca atttctaaga ggactggatt    5460
gcagaagact cggggacaac atttgatcca agatcttaaa tgttatattg ataaccatgc    5520
tcagcaatga gctattagat tcattttggg aaatctccat aatttcaatt tgtaaacttt    5580
gttaagacct gtctacattg ttatatgtgt gtgacttgag taatgttatc aacgttttttg   5640 taaatattta ctatgttttt ctattagcta aattccaaca attttgtact ttaataaa      5698
```

<210> SEQ ID NO 6
<211> LENGTH: 2436
<212> TYPE: DNA
<213> ORGANISM: Homo sapiens

<400> SEQUENCE: 6

```
attcatttcc cccagtgacc ttgacaagtc agaagcttga aagcagggaa atccggatgt        60
ctcggttatg aagtggagca gtgagtgtga gcctcaacat agttccagaa ctctccatcc       120
ggactagtta ttgagcatct gcctctcata tcaccagtgg ccatctgagg tgtttccctg       180
gctctgaagg ggtaggcacg atggccaggt gcttcagcct ggtgttgctt ctcacttcca       240
tctggaccac gaggctcctg gtccaaggct ctttgcgtgc agaagagctt tccatccagg       300
```

```
tgtcatgcag aattatgggg atcacccttg tgagcaaaaa ggcgaaccag cagctgaatt    360
tcacagaagc taaggaggcc tgtaggctgc tgggactaag tttggccggc aaggaccaag    420
ttgaaacagc cttgaaagct agctttgaaa cttgcagcta tggctgggtt ggagatggat    480
tcgtggtcat ctctaggatt agcccaaacc ccaagtgtgg gaaaaatggg gtgggtgtcc    540
tgatttggaa ggttccagtg agccgacagt ttgcagccta ttgttacaac tcatctgata    600
cttggactaa ctcgtgcatt ccagaaatta tcaccaccaa agatcccata ttcaacactc    660
aaactgcaac acaaacaaca gaatttattg tcagtgacag tacctactcg gtggcatccc    720
cttactctac aatacctgcc cctactacta ctcctcctgc tccagcttcc acttctattc    780
cacggagaaa aaaattgatt tgtgtcacag aagtttttat ggaaactagc accatgtcta    840
cagaaactga accatttgtt gaaaataaag cagcattcaa gaatgaagct gctgggtttg    900
gaggtgtccc cacggctctg ctagtgcttg ctctcctctt ctttggtgct gcagctggtc    960
ttggattttg ctatgtcaaa aggtatgtga aggccttccc ttttacaaac aagaatcagc   1020
agaaggaaat gatcgaaacc aaagtagtaa aggaggagaa ggccaatgat agcaacccta   1080
atgaggaatc aaagaaaact gataaaaacc agaagagtc caagagtcca agcaaaacta   1140
ccgtgcgatg cctggaagct gaagtttaga tgagacagaa atgaggagac acacctgagg   1200
ctggtttctt tcatgctcct taccctgccc cagctgggga aatcaaaagg gccaaagaac   1260
caaagaagaa agtccaccct tggttcctaa ctggaatcag ctcaggactg ccattggact   1320
atggagtgca ccaaagagaa tgcccttctc cttattgtaa ccctgtctgg atcctatcct   1380
cctacctcca aagcttccca cggcctttct agcctggcta tgtcctaata atatcccact   1440
gggagaaagg agttttgcaa agtgcaagga cctaaaacat ctcatcagta tccagtggta   1500
aaaaggcctc ctggctgtct gaggctaggt gggttgaaag ccaaggagtc actgagacca   1560
aggcttctc tactgattcc gcagctcaga cccttttcttc agctctgaaa gagaaacacg   1620
tatcccacct gacatgtcct tctgagcccg gtaagagcaa aagaatggca gaaaagttta   1680
gccccctgaaa gccatggaga ttctcataac ttgagaccta atctctgtaa agctaaaata   1740
aagaaataga caaggctga ggatacgaca gtacactgtc agcagggact gtaaacacag   1800
acagggtcaa agtgttttct ctgaacacat tgagttggaa tcactgttta gaacacacac   1860
acttactttt tctggtctct accactgctg atattttctc taggaaatat acttttacaa   1920
gtaacaaaaa taaaaactct tataaatttc tattttttatc tgagttacag aaatgattac   1980
taaggaagat tactcagtaa tttgtttaaa aagtaataaa attcaacaaa catttgctga   2040
atagctacta tatgtcaagt gctgtgcaag gtattacact ctgtaattga atattattcc   2100
tcaaaaaatt gcacatagta gaacgctatc tgggaagcta tttttttcag ttttgatatt   2160
tctagcttat ctacttccaa actaattttt attttttgctg agactaatct tattcattt   2220
ctctaatatg gcaaccatta taaccttaat ttattattaa catacctaag aagtacattg   2280
ttacctctat ataccaaagc acattttaaa agtgccatta caaatgtat cactagccct    2340
ccttttttcca acaagagggg actgagagat gcagaaatat ttgtgacaaa aaattaaagc   2400
atttagaaaa cttaaaaaaa aaaaaaaaa aaaaaa                              2436
```

<210> SEQ ID NO 7
<211> LENGTH: 4828
<212> TYPE: DNA
<213> ORGANISM: Homo sapiens

<400> SEQUENCE: 7

```
agtggcgtcg gaactgcaaa gcacctgtga gcttgcggaa gtcagttcag actccagccc    60
gctccagccc ggcccgaccc gaccgcaccc ggcgcctgcc ctcgctcggc gtccccggcc   120
agccatgggc ccttggagcc gcagcctctc ggcgctgctg ctgctgctgc aggtctcctc   180
ttggctctgc caggagccgg agccctgcca ccctggcttt gacgccgaga gctacacgtt   240
cacggtgccc cggcgccacc tggagagagg ccgcgtcctg ggcagagtga attttgaaga   300
ttgcaccggt cgacaaagga cagcctattt ttccctcgac acccgattca agtgggcac   360 agatggtgtg attacagtca aaaggcctct acggtttcat aacccacaga tccatttctt   420
ggtctacgcc tgggactcca cctacagaaa gttttccacc aaagtcacgc tgaatacagt   480
ggggcaccac caccgccccc cgccccatca ggcctccgtt tctggaatcc aagcagaatt   540
gctcacattt cccaactcct ctcctggcct cagaagacag aagagagact gggttattcc   600
tcccatcagc tgcccagaaa atgaaaaagg cccatttcct aaaaacctgg ttcagatcaa   660
atccaacaaa gacaaagaag gcaaggtttt ctacagcatc actggccaag agctgacac   720 accccctgtt ggtgtcttta ttattgaaag agaaacagga tggctgaagg tgacagagcc   780
tctggataga gaacgcattg ccacatacac tctcttctct cacgctgtgt catccaacgg   840
gaatgcagtt gaggatccaa tggagatttt gatcacggta accgatcaga atgacaacaa   900
gcccgaattc acccaggagg tctttaaggg gtctgtcatg gaaggtgctc ttccaggaac   960
ctctgtgatg gaggtcacag ccacagacgc ggacgatgat gtgaacacct acaatgccgc  1020
catcgcttac accatcctca gccaagatcc tgagctccct gacaaaaata tgttcaccat  1080
taacaggaac acaggagtca tcagtgtggt caccactggg ctggaccgag agagtttccc  1140
tacgtatacc ctggtggttc aagctgctga ccttcaaggt gaggggttaa gcacaacagc  1200
aacagctgtg atcacagtca ctgacaccaa cgataatcct ccgatcttca atcccaccac  1260
gtacaagggt caggtgcctg agaacgaggc taacgtcgta atcaccacac tgaaagtgac  1320
tgatgctgat gccccccaata cccccagcgtg ggaggctgta tacaccatat tgaatgatga  1380
tggtggacaa tttgtcgtca ccacaaatcc agtgaacaac gatggcattt tgaaaacagc  1440
aaagggcttg gattttgagg ccaagcagca gtacattcta cacgtagcag tgacgaatgt  1500
ggtacctttt gaggtctctc tcaccacctc cacagccacc gtcaccgtgg atgtgctgga  1560
tgtgaatgaa gcccccatct tgtgcctcc tgaaaagaga gtggaagtgt ccgaggactt  1620
tggcgtgggc caggaaatca catcctacac tgcccaggag ccagacacat ttatggaaca  1680
gaaaataaca tatcggattt ggagagacac tgccaactgg ctggagatta tccggacac  1740 tggtgccatt tccactcggg ctgagctgga cagggaggat tttgagcacg tgaagaacag  1800
cacgtacaca gccctaatca tagctacaga caatggttct ccagttgcta ctggaacagg  1860
gacacttctg ctgatcctgt ctgatgtgaa tgacaacgcc cccataccag aacctcgaac  1920
tatattcttc tgtgagagga atccaaagcc tcaggtcata aacatcattg atgcagacct  1980
tcctcccaat acatctccct tcacagcaga actaacacac ggggcgagtg ccaactggac  2040
cattcagtac aacgacccaa cccaagaatc tatcattttg aagccaagaa tggccttaga  2100
ggtgggtgac tacaaaatca atctcaagct catggataac cagaataaag accaagtgac  2160
caccttagag gtcagcgtgt gtgactgtga agggcgcc ggcgtctgta ggaaggcaca  2220
gcctgtcgaa gcaggattgc aaattcctgc cattctgggg attcttggag gaattcttgc  2280
tttgctaatt ctgattctgc tgctcttgct gtttcttcgg aggagagcgg tggtcaaaga  2340
gcccttactg cccccagagg atgacacccg ggacaacgtt tattactatg atgaagaagg  2400
```

| | |
|---|---|
| aggcggagaa gaggaccagg actttgactt gagccagctg cacaggggcc tggacgctcg | 2460 |
| gcctgaagtg actcgtaacg acgttgcacc aaccctcatg agtgtccccc ggtatcttcc | 2520 |
| ccgccctgcc aatcccgatg aaattggaaa ttttattgat gaaaatctga agcggctga | 2580 |
| tactgacccc acagcccgc cttatgattc tctgctcgtg tttgactatg aaggaagcgg | 2640 |
| ttccgaagct gctagtctga gctccctgaa ctcctcagag tcagacaaag accaggacta | 2700 |
| tgactacttg aacgaatggg gcaatcgctt caagaagctg gctgacatgt acggaggcgg | 2760 |
| cgaggacgac tagggactc gagagaggcg ggccccagac ccatgtgctg ggaaatgcag | 2820 |
| aaatcacgtt gctggtggtt tttcagctcc cttcccttga gatgagtttc tggggaaaaa | 2880 |
| aaagagactg gttagtgatg cagttagtat agctttatac tctctccact ttatagctct | 2940 |
| aataagtttg tgttagaaaa gtttcgactt atttcttaaa gctttttttt ttttcccatc | 3000 |
| actctttaca tggtggtgat gtccaaaaga tacccaaatt ttaatattcc agaagaacaa | 3060 |
| ctttagcatc agaaggttca cccagcaccct tgcagatttt cttaaggaat tttgtctcac | 3120 |
| ttttaaaaag aaggggagaa gtcagctact ctagttctgt tgttttgtgt atataatttt | 3180 |
| ttaaaaaaaa tttgtgtgct tctgctcatt actacactgg tgtgtccctc tgcctttttt | 3240 |
| tttttttta agacagggtc tcattctatc ggccaggctg gagtgcagtg gtgcaatcac | 3300 |
| agctcactgc agccttgtcc tcccaggctc aagctatcct tgcacctcag cctcccaagt | 3360 |
| agctgggacc acaggcatgc accactacgc atgactaatt ttttaaatat ttgagacggg | 3420 |
| gtctccctgt gttacccagg ctggtctcaa actcctgggc tcaagtgatc ctcccatctt | 3480 |
| ggcctcccag agtattggga ttacagacat gagccactgc acctgccccag ctccccaact | 3540 |
| ccctgccatt ttttaagaga cagtttcgct ccatcgccca ggcctgggat gcagtgatgt | 3600 |
| gatcatagct cactgtaacc tcaaactctg gggctcaagc agttctccca ccagcctcct | 3660 |
| tttatttttt ttgtacagat ggggtcttgc tatgttgccc aagctggtct taaactcctg | 3720 |
| gcctcaagca atccttctgc cttggccccc caaagtgctg ggattgtggg catgagctgc | 3780 |
| tgtgcccagc ctccatgttt taatatcaac tctcactcct gaattcagtt gctttgccca | 3840 |
| agataggagt tctctgatgc agaaattatt gggctctttt agggtaagaa gtttgtgtct | 3900 |
| ttgtctggcc acatcttgac taggtattgt ctactctgaa gacctttaat ggcttccctc | 3960 |
| tttcatctcc tgagtatgta acttgcaatg ggcagctatc cagtgacttg ttctgagtaa | 4020 |
| gtgtgttcat taatgtttat ttagctctga agcaagagtg atatactcca ggacttagaa | 4080 |
| tagtgcctaa agtgctgcag ccaaagacag agcggaacta tgaaaagtgg gcttggagat | 4140 |
| ggcaggagag cttgtcattg agcctggcaa tttagcaaac tgatgctgag gatgattgag | 4200 |
| gtgggtctac ctcatctctg aaaattctgg aaggaatgga ggagtctcaa catgtgtttc | 4260 |
| tgacacaaga tccgtggttt gtactcaaag cccagaatcc ccaagtgcct gcttttgatg | 4320 |
| atgtctacag aaaatgctgg ctgagctgaa cacatttgcc caattccagg tgtgcacaga | 4380 |
| aaaccgagaa tattcaaaat tccaaatttt ttcttaggag caagaagaaa atgtggccct | 4440 |
| aaagggggtt agttgagggg taggggtag tgaggatctt gatttggatc tcttttttatt | 4500 |
| taaatgtgaa tttcaacttt tgacaatcaa agaaaagact tttgttgaaa tagctttact | 4560 |
| gtttctcaag tgttttggag aaaaaaatca accctgcaat cacttttttgg aattgtcttg | 4620 |
| attttttcggc agttcaagct atatcgaata tagttctgtg tagagaatgt cactgtagtt | 4680 |
| ttgagtgtat acatgtgtgg gtgctgataa ttgtgtatttt tctttggggg tggaaaagga | 4740 |
| aaacaattca agctgagaaa agtattctca aagatgcatt tttataaatt ttattaaaca | 4800 |

```
attttgttaa accataaaaa aaaaaaaa                                         4828
```

<210> SEQ ID NO 8
<211> LENGTH: 2620
<212> TYPE: DNA
<213> ORGANISM: Homo sapiens

<400> SEQUENCE: 8

```
agatgcgagc actgcggctg ggcgctgagg atcagccgct tcctgcctgg attccacagc       60
ttcgcgccgt gtactgtcgc cccatccctg cgcgcccagc ctgccaagca gcgtgccccg      120
gttgcaggcg tcatgcagcg ggcgcgaccc acgctctggg ccgctgcgct gactctgctg      180
gtgctgctcc gcgggccgcc ggtggcgcgg gctggcgcga gctcggcggg cttgggtccc      240
gtggtgcgct gcgagccgtg cgacgcgcgt gcactggccc agtgcgcgcc tccgcccgcc      300
gtgtgcgcgg agctggtgcg cgagccgggc tgcggctgct gcctgacgtg cgcactgagc      360
gagggccagc cgtgcggcat ctacaccgag cgctgtggcc ccggccttcg ctgccagccg      420
tcgcccgacg aggcgcgacc gctgcaggcg ctgctggacg gccgcgggct ctgcgtcaac      480
gctagtgccg tcagccgcct gcgcgcctac ctgctgccag cgccgccagc tccaggaaat      540
gctagtgagt cggaggaaga ccgcagcgcc ggcagtgtgg agagcccgtc cgtctccagc      600
acgcaccggg tgtctgatcc caagttccac cccctccatt caaagataat catcatcaag      660
aaagggcatg ctaaagacag ccagcgctac aaagttgact acgagtctca gagcacagat      720
acccagaact tctcctccga gtccaagcgg gagacagaat atggtccctg ccgtagagaa      780
atggaagaca cactgaatca cctgaagttc ctcaatgtgc tgagtcccag gggtgtacac      840
attcccaact gtgacaagaa gggatttttat aagaaaaagc agtgtcgccc ttccaaaggc      900
aggaagcggg gcttctgctg gtgtgtggat aagtatgggg agcctctccc aggctacacc      960
accaagggga aggaggacgt gcactgctac agcatgcaga gcaagtagac gcctgccgca     1020
aggttaatgt ggagctcaaa tatgccttat tttgcacaaa agactgccaa ggacatgacc     1080
agcagctggc tacagcctcg atttatattt ctgtttgtgg tgaactgatt ttttttaaac     1140
caaagtttag aaagaggttt ttgaaaatgcc tatggtttct ttgaatggta aacttgagca     1200
tcttttcact ttccagtagt cagcaaagag cagtttgaat tttcttgtcg cttcctatca     1260
aaatattcag agactcgagc acagcaccca gacttcatgc gcccgtggaa tgctcaccac     1320
atgttggtcg aagcggccga ccactgactt tgtgacttag gcggctgtgt tgcctatgta     1380
gagaacacgc ttcaccccca ctcccgtac agtgcgcaca ggctttatcg agaataggaa     1440
aacctttaaa ccccggtcat ccggacatcc aacgcatgc tcctggagct cacagccttc     1500
tgtggtgtca tttctgaaac aagggcgtgg atccctcaac caagaagaat gtttatgtct     1560
tcaagtgacc tgtactgctt ggggactatt ggagaaaata aggtggagtc ctacttgttt     1620
aaaaaatatg tatctaagaa tgttctaggg cactctggga acctataaag gcaggtattt     1680
cgggccctcc tcttcaggaa tcttcctgaa gacatggccc agtcgaaggc ccaggatggc     1740
ttttgctgcg gccccgtggg gtaggaggga cagagagaca gggagagtca gcctccacat     1800
tcagaggcat cacaagtaat ggcacaattc ttcggatgac tgcagaaaat agtgttttgt     1860
agttcaacaa ctcaagacga agcttatttc tgaggataag ctctttaaag gcaaagcttt     1920
attttcatct ctcatctttt gtcctcctta gcacaatgta aaaagaata gtaatatcag     1980
aacaggaagg aggaatggct tgctggggag cccatccagg acactgggag cacatagaga     2040
ttcacccatg tttgttgaac ttagagtcat tctcatgctt tcctttataa ttcacacata     2100
```

| tatgcagaga agatatgttc ttgttaacat tgtatacaac atagccccaa atatagtaag | 2160 |
| atctatacta gataatccta gatgaaatgt tagagatgct atatgataca actgtggcca | 2220 |
| tgactgagga aaggagctca cgcccagaga ctgggctgct ctcccggagg ccaaacccaa | 2280 |
| gaaggtctgg caaagtcagg ctcagggaga ctctgccctg ctgcagacct cggtgtggac | 2340 |
| acacgctgca tagagctctc cttgaaaaca gaggggtctc aagacattct gcctacctat | 2400 |
| tagcttttct ttattttttt aacttttttgg ggggaaaagt attttttgaga agtttgtctt | 2460 |
| gcaatgtatt tataaatagt aaataaagtt tttaccatta aaaaaatatc tttcccttttg | 2520 |
| ttattgacca tctctgggct ttgtatcact aattattttta ttttattata taataattat | 2580 |
| tttattataa taaaatcctg aaaggggaaa ataaaaaaaa | 2620 |

<210> SEQ ID NO 9
<211> LENGTH: 6405
<212> TYPE: DNA
<213> ORGANISM: Homo sapiens

<400> SEQUENCE: 9

| ggtttttgag cccattactg ttggagctac agggagagaa acagaggagg agactgcaag | 60 |
| agatcattgg aggccgtggg cacgctcttt actccatgtg tgggacattc attgcggaat | 120 |
| aacatcggag gagaagtttc ccagagctat ggggacttcc catccggcgt tcctggtctt | 180 |
| aggctgtctt ctcacagggc tgagcctaat cctctgccag ctttcattac cctctatcct | 240 |
| tccaaatgaa aatgaaaagg ttgtgcagct gaattcatcc tttctctga gatgctttgg | 300 |
| ggagagtgaa gtgagctggc agtaccccat gtctgaagaa gagagctccg atgtggaaat | 360 |
| cagaaatgaa gaaaacaaca gcggcctttt tgtgacggtc ttggaagtga gcagtgcctc | 420 |
| ggcggcccac acagggttgt acacttgcta ttacaaccac actcagacag aagagaatga | 480 |
| gcttgaaggc aggcacattt acatctatgt gccagaccca gatgtagcct ttgtacctct | 540 |
| aggaatgacg gattatttag tcatcgtgga ggatgatgat tctgccatta taccttgtcg | 600 |
| cacaactgat cccgagactc ctgtaacctt acacaacagt gagggggtgg tacctgcctc | 660 |
| ctacgacagc agacagggct ttaatgggac cttcactgta gggccctata tctgtgaggc | 720 |
| caccgtcaaa ggaaagaagt tccagaccat cccatttaat gtttatgctt taaaagcaac | 780 |
| atcagagctg gatctagaaa tggaagctct taaaaccgtg tataagtcag ggaaaacgat | 840 |
| tgtggtcacc tgtgctgttt ttaacaatga ggtggttgac cttcaatgga cttaccctgg | 900 |
| agaagtgaaa ggcaaaggca tcacaatgct ggaagaaatc aaagtcccat ccatcaaatt | 960 |
| ggtgtacact ttgacggtcc ccgaggccac ggtgaaagac agtggagatt acgaatgtgc | 1020 |
| tgcccgccag gctaccaggg aggtcaaaga aatgaagaaa gtcactattt ctgtccatga | 1080 |
| gaaaggtttc attgaaatca aacccaccttt cagccagttg gaagctgtca acctgcatga | 1140 |
| agtcaaacat tttgttgtag aggtgcgggc ctacccacct cccaggatat cctggctgaa | 1200 |
| aaacaatctg actctgattg aaaatctcac tgagatcacc actgatgtgg aaaagattca | 1260 |
| ggaaataagg tatcgaagca aattaaagct gatccgtgct aaggaagaag acagtggcca | 1320 |
| ttatactatt gtagctcaaa atgaagatgc tgtgaagagc tatacttttg aactgttaac | 1380 |
| tcaagttcct tcatccattc tggacttggt cgatgatcac catggctcaa ctggggggaca | 1440 |
| gacggtgagg tgcacagctg aaggcacgcc gcttcctgat attgagtgga tgatatgcaa | 1500 |
| agatattaag aaaatgtaata atgaaacttc ctggactatt ttggccaaca atgtctcaaa | 1560 |
| catcatcacg gagatccact cccgagacag gagtaccgtg gagggccgtg tgactttcgc | 1620 |

```
caaagtggag gagaccatcg ccgtgcgatg cctggctaag aatctccttg gagctgagaa    1680
ccgagagctg aagctggtgg ctcccaccct gcgttctgaa ctcacggtgg ctgctgcagt    1740
cctggtgctg ttggtgattg tgatcatctc acttattgtc ctggttgtca tttggaaaca    1800
gaaaccgagg tatgaaattc gctggagggt cattgaatca atcagccag atggacatga     1860 atatatttat gtggacccga tgcagctgcc ttatgactca agatgggagt ttccaagaga    1920
tggactagtg cttggtcggg tcttggggtc tggagcgttt gggaaggtgg ttgaaggaac    1980
agcctatgga ttaagccggt cccaacctgt catgaaagtt gcagtgaaga tgctaaaacc    2040
cacggccaga tccagtgaaa acaagctct catgtctgaa ctgaagataa tgactcacct     2100
ggggccacat ttgaacattg taaacttgct gggagcctgc accaagtcag gccccattta    2160
catcatcaca gagtattgct tctatggaga tttggtcaac tatttgcata agaatagga     2220 tagcttcctg agccaccacc cagagaagcc aaagaaagag ctggatatct ttggattgaa    2280
ccctgctgat gaaagcacac ggagctatgt tattttatct tttgaaaaca atggtgacta    2340
catggacatg aagcaggctg atactacaca gtatgtcccc atgctagaaa ggaaagaggt    2400
ttctaaatat tccgacatcc agagatcact ctatgatcgt ccagcctcat ataagaagaa    2460
atctatgtta gactcagaag tcaaaaacct cctttcagat gataactcag aaggccttac    2520
tttattggat ttgttgagct tcacctatca agttgcccga ggaatggagt ttttggcttc    2580
aaaaaattgt gtccaccgtg atctggctgc tcgcaacgtc ctcctggcac aaggaaaaat    2640
tgtgaagatc tgtgactttg gcctggccag agacatcatg catgattcga actatgtgtc    2700
gaaaggcagt acctttctgc ccgtgaagtg gatggctcct gagagcatct ttgacaacct    2760
ctacaccaca ctgagtgatg tctgtgtctta tggcattctg ctctgggaga tcttttccct   2820
tggtggcacc ccttaccccg gcatgatggt ggattctact ttctacaata agatcaagag    2880
tgggtaccgg atggccaagc ctgaccacgc taccagtgaa gtctacgaga tcatggtgaa    2940
atgctggaac agtgagccgg agaagagacc ctccttttac cacctgagtg agattgtgga    3000
gaatctgctg cctggacaat ataaaaagag ttatgaaaaa attcacctgg acttcctgaa    3060
gagtgaccat cctgctgtgg cacgcatgcg tgtggactca gacaatgcat acattggtgt    3120
cacctacaaa aacgaggaag acaagctgaa ggactgggag ggtggtctgg atgagcagag    3180
actgagcgct gacagtggct acatcattcc tctgcctgac attgaccctg tccctgagga    3240
ggaggacctg ggcaagagga acagacacag ctcgcagacc tctgaagaga gtgccattga    3300
gacgggttcc agcagttcca ccttcatcaa gagagaggac gagaccattg aagacatcga    3360
catgatggac gacatcggca tagactcttc agacctggtg gaagacagct tcctgtaact    3420
ggcggattcg aggggttcct tccacttctg ggccacctc tggatcccgt tcagaaaacc     3480
actttattgc aatgcggagg ttgagaggag gacttggttg atgtttaaag agaagttccc    3540
agccaagggc ctcggggagc gttctaaata tgaatgaatg ggatattttg aaatgaactt    3600
tgtcagtgtt gcctcttgca atgcctcagt agcatctcag tggtgtgtga gtttggaga    3660 tagatggata agggaataat aggccacaga aggtgaactt tgtgcttcaa ggacattggt    3720
gagagtccaa cagacacaat ttatactgcg acagaacttc agcattgtaa ttatgtaaat    3780
aactctaacc aaggctgtgt ttagattgta ttaactatct tctttggact tctgaagaga    3840
ccactcaatc catccatgta cttccctctt gaaacctgat gtcagctgct gttgaacttt    3900
ttaaagaagt gcatgaaaaa ccattttga accttaaaag gtactggtac tatagcattt      3960
tgctatcttt tttagtgtta aagagataaa gaataataat taaccaacct tgtttaatag    4020
```

```
atttgggtca tttagaagcc tgacaactca ttttcatatt gtaatctatg tttataatac    4080
tactactgtt atcagtaatg ctaaatgtgt aataatgtaa catgatttcc ctccagagaa    4140
agcacaattt aaaacaatcc ttactaagta ggtgatgagt ttgacagttt ttgacattta    4200
tattaaataa catgtttctc tataaagtat ggtaatagct ttagtgaatt aaatttagtt    4260
gagcatagag aacaaagtaa aagtagtgtt gtccaggaag tcagaatttt taactgtact    4320
gaataggttc cccaatccat cgtattaaaa aacaattaac tgccctctga aataatggga    4380
ttagaaacaa acaaaactct taagtcctaa aagttctcaa tgtagaggca taaacctgtg    4440
ctgaacataa cttctcatgt atattaccca atggaaaata taatgatcag caaaaagact    4500
ggatttgcag aagttttttt tttttttttc ttcatgcctg atgaaagctt tggcgacccc    4560
aatatatgta ttttttgaat ctatgaacct gaaaagggtc agaaggatgc ccagacatca    4620
gcctccttct ttcaccccctt accccaaaga gaaagagttt gaaactcgag accataaaga    4680
tattctttag tggaggctgg atgtgcatta gcctggatcc tcagttctca aatgtgtgtg    4740
gcagccagga tgactagatc ctgggtttcc atccttgaga ttctgaagta tgaagtctga    4800
gggaaaccag agtctgtatt tttctaaact ccctggctgt tctgatcggc cagttttcgg    4860
aaacactgac ttaggtttca ggaagttgcc atgggaaaca aataatttga actttggaac    4920
agggttggaa ttcaaccacg caggaagcct actatttaaa tccttggctt caggttagtg    4980
acatttaatg ccatctagct agcaattgcg accttaattt aactttccag tcttagctga    5040
ggctgagaaa gctaaagttt ggttttgaca ggttttccaa aagtaaagat gctacttccc    5100
actgtatggg ggagattgaa cttccccgt ctcccgtctt ctgcctccca ctccataccc    5160
cgccaaggaa aggcatgtac aaaaattatg caattcagtg ttccaagtct ctgtgtaacc    5220
agctcagtgt tttggtggaa aaaacatttt aagtttact gataatttga ggttagatgg    5280
gaggatgaat tgtcacatct atccacactg tcaaacaggt tggtgtgggt tcattggcat    5340
tctttgcaat actgcttaat tgctgatacc atatgaatga acatgggct gtgattactg    5400 caatcactgt gctatcggca gatgatgctt tggaagatgc agaagcaata ataaagtact    5460
tgactaccta ctggtgtaat ctcaatgcaa gccccaactt tcttatccaa cttttttcata    5520 gtaagtgcga agactgagcc agattggcca attaaaaacg aaaacctgac taggttctgt    5580
agagccaatt agacttgaaa tacgtttgtg tttctagaat cacagctcaa gcattctgtt    5640
tatcgctcac tctcccttgt acagccttat tttgttggtg ctttgcattt tgatattgct    5700
gtgagccttg catgacatca tgaggccgga tgaaacttct cagtccagca gtttccagtc    5760
ctaacaaatg ctcccacctg aatttgtata tgactgcatt tgtgtgtgtg tgtgtgtttt    5820
cagcaaattc cagatttgtt tccttttggc ctcctgcaaa gtctccagaa gaaaatttgc    5880
caatctttcc tactttctat ttttatgatg acaatcaaag ccggcctgag aaacactatt    5940
tgtgactttt taaacgatta gtgatgtcct taaaatgtgg tctgccaatc tgtacaaaat    6000
ggtcctattt ttgtgaagag ggacataaga taaaatgatg ttatacatca atatgtatat    6060
atgtatttct atatagactt ggagaatact gccaaaacat ttatgacaag ctgtatcact    6120
gccttcgttt atattttttt aactgtgata atccccacag gcacattaac tgttgcactt    6180
ttgaatgtcc aaaatttata ttttagaaat aataaaaaga aagatactta catgttccca    6240
aaacaatggt gtggtgaatg tgtgagaaaa actaacttga tagggtctac caatacaaaa    6300
tgtattacga atgcccctgt tcatgttttt gttttaaaac gtgtaaatga agatctttat    6360
atttcaataa atgatatata atttaaagtt aaaaaaaaaa aaaaa                   6405
```

<210> SEQ ID NO 10
<211> LENGTH: 4119
<212> TYPE: DNA
<213> ORGANISM: Homo sapiens

<400> SEQUENCE: 10

```
ctggagagcc tgctgcccgc ccgcccgtaa aatggtcccc tcggctggac agctcgccct      60
gttcgctctg ggtattgtgt tggctgcgtg ccaggccttg gagaacagca cgtcccgct     120
gagtgcagac ccgcccgtgg ctgcagcagt ggtgtcccat tttaatgact gcccagattc     180
ccacactcag ttctgcttcc atggaacctg caggtttttg gtgcaggagg acaagccagc     240
atgtgtctgc cattctgggt acgttggtgc acgctgtgag catgcggacc tcctggccgt     300
ggtggctgcc agccagaaga agcaggccat caccgccttg gtggtggtct ccatcgtggc     360
cctggctgtc cttatcatca catgtgtgct gatacactgc tgccaggtcc gaaaacactg     420
tgagtggtgc cgggccctca tctgccggca cgagaagccc agcgccctcc tgaagggaag     480
aaccgcttgc tgccactcag aaacagtggt ctgaagagcc cagaggagga gtttggccag     540
gtggactgtg gcagatcaat aaagaaaggc ttcttcagga cagcactgcc agagatgcct     600
gggtgtgcca cagaccttcc tacttggcct gtaatcacct gtgcagcctt ttgtgggcct     660
tcaaaactct gtcaagaact ccgtctgctt ggggttattc agtgtgacct agagaagaaa     720
tcagcggacc acgatttcaa gacttgttaa aaagaactg caaagagacg gactcctgtt     780
caccctaggtg aggtgtgtgc agcagttggt gtctgagtcc acatgtgtgc agttgtcttc     840
tgccagccat ggattccagg ctatatattt cttttaatg ggccacctcc ccacaacaga     900
attctgccca acacaggaga tttctatagt tattgttttc tgtcatttgc ctactgggga     960
agaaagtgaa ggaggggaaa ctgtttaata tcacatgaag acccctagctt taagagaagc    1020
tgtatcctct aaccacgaga ctctcaacca gcccaacatc ttccatggac acatgacatt    1080
gaagaccatc ccaagctatc gccacccttg gagatgatgt cttatttatt agatggataa    1140
tggttttatt tttaatctct taagtcaatg taaaaagtat aaaaccccctt cagacttcta    1200
cattaatgat gtatgtgttg ctgactgaaa agctatactg attagaaatg tctggcctct    1260
tcaagacagc taaggcttgg gaaaagtctt ccagggtgcg gagatggaac cagaggctgg    1320
gttactggta ggaataaagg taggggttca gaaatggtgc cattgaagcc acaaagccgg    1380
taaatgcctc aatacgttct gggagaaaac ttagcaaatc catcagcagg gatctgtccc    1440
ctctgttggg gagagaggaa gagtgtgtgt gtctacacag gataaaccca atacatattg    1500
tactgctcag tgattaaatg ggttcacttc ctcgtgagcc ctcggtaagt atgtttagaa    1560
atagaacatt agccacgagc cataggcatt tcaggccaaa tccatgaaag ggggaccagt    1620
cattttatttt ccattttgtt gcttggttgg tttgttgctt tattttttaaa aggagaagtt    1680
taactttgct atttattttc gagcactagg aaaactattc cagtaattt ttttttcctca    1740
tttccattca ggatgccggc tttattaaca aaaactctaa caagtcacct ccactatgtg    1800
ggtcttcctt tccctcaag agaaggagca attgttcccc tgacatctgg gtccatctga    1860
cccatggggc ctgcctgtga gaaacagtgg gtcccttcaa atacatagtg gatagctcat    1920
ccctaggaat tttcattaaa atttggaaac agagtaatga agaaataata tataaactcc    1980
ttatgtgagg aaatgctact aatatctgaa aagtgaaaga tttctatgta ttaactctta    2040
agtgcaccta gcttattaca tcgtgaaagg tacatttaaa atatgttaaa ttggcttgaa    2100
attttcagag aattttgtct tcccctaatt cttcttcctt ggtctggaag aacaatttct    2160
```

```
atgaattttc tctttatttt ttttttataa ttcagacaat tctatgaccc gtgtcttcat    2220
ttttggcact cttatttaac aatgccacac ctgaagcact tggatctgtt cagagctgac    2280
cccctagcaa cgtagttgac acagctccag gttttttaaat tactaaaata agttcaagtt   2340
tacatccctt gggccagata tgtgggttga ggcttgactg tagcatcctg cttagagacc    2400
aatcaatgga cactggtttt tagacctcta tcaatcagta gttagcatcc aagagacttt    2460
gcagaggcgt aggaatgagg ctggacagat ggcggaacga gaggttccct gcgaagactt    2520
gagatttagt gtctgtgaat gttctagttc ctaggtccag caagtcacac ctgccagtgc    2580
cctcatcctt atgcctgtaa cacacatgca gtgagaggcc tcacatatac gcctccctag    2640
aagtgccttc caagtcagtc ctttggaaac cagcaggtct gaaaagagg ctgcatcaat     2700 gcaagcctgg ttggaccatt gtccatgcct caggatagaa cagcctggct tatttgggga    2760 ttttcttct agaaatcaaa tgactgataa gcattggctc cctctgccat ttaatggcaa     2820
tggtagtctt tggttagctg caaaaatact ccatttcaag ttaaaaatgc atcttctaat    2880
ccatctctgc aagctccctg tgtttccttg ccctttagaa aatgaattgt tcactacaat    2940
tagagaatca tttaacatcc tgacctggta agctgccaca cacctggcag tggggagcat    3000
cgctgtttcc aatggctcag gagacaatga aaagccccca tttaaaaaaa taacaaacat    3060
tttttaaaag gcctccaata ctcttatgga gcctggattt tcccactgc tctacaggct     3120 gtgactttt ttaagcatcc tgacaggaaa tgttttcttc tacatggaaa gatagacagc     3180
agccaaccct gatctggaag acagggcccc ggctggacac acgtggaacc aagccaggga    3240
tgggctggcc attgtgtccc cgcaggagag atgggcagaa tggccctaga gttcttttcc    3300
ctgagaaagg agaaaaagat gggattgcca ctcacccacc cacactggta agggaggaga    3360
atttgtgctt ctggagcttc tcaagggatt gtgttttgca ggtacagaaa actgcctgtt    3420
atcttcaagc caggttttcg agggcacatg ggtcaccagt tgcttttca gtcaatttgg    3480 ccgggatgga ctaatgaggc tctaacactg ctcaggagac ccctgccctc tagttggttc    3540
tgggctttga tctcttccaa cctgcccagt cacagaagga ggaatgactc aaatgcccaa    3600
aaccaagaac acattgcaga agtaagcaaa acatgtatat ttttaaatgt tctaacataa   3660
gacctgttct ctctagccat tgatttacca ggctttctga aagatctagt ggttcacaca    3720
gagagagaga gagtactgaa aaagcaactc ctcttcttag tcttaataat ttactaaaat    3780
ggtcaacttt tcattatctt tattataata aacctgatgc ttttttttag aactccttac    3840
tctgatgtct gtatatgttg cactgaaaag gttaatattt aatgttttaa tttattttgt    3900
gtggtaagtt aattttgatt tctgtaatgt gttaatgtga ttagcagtta ttttccttaa    3960
tatctgaatt atacttaaag agtagtgagc aatataagac gcaattgtgt ttttcagtaa    4020
tgtgcattgt tattgagttg tactgtacct tatttggaag gatgaaggaa tgaacctttt    4080
tttcctaaaa aaaaaaaaaa aaaaaaaaa aaaaaaaa                             4119

<210> SEQ ID NO 11
<211> LENGTH: 4304
<212> TYPE: DNA
<213> ORGANISM: Homo sapiens

<400> SEQUENCE: 11
cacacggact acaggggagt tttgttgaag ttgcaaagtc ctggagcctc cagagggctg      60
tcggcgcagt agcagcgagc agcagagtcc gcacgctccg gcgaggggca gaagagcgcg     120
agggagcgcg gggcagcaga agcgagagcc gagcgcggac ccagccagga cccacagccc    180
```

```
tccccagctg cccaggaaga gccccagcca tggaacacca gctcctgtgc tgcgaagtgg   240
aaaccatccg ccgcgcgtac cccgatgcca acctcctcaa cgaccgggtg ctgcgggcca   300
tgctgaaggc ggaggagacc tgcgcgccct cggtgtccta cttcaaatgt gtgcagaagg   360
aggtcctgcc gtccatgcgg aagatcgtcg ccacctggat gctggaggtc tgcgaggaac   420
agaagtgcga ggaggaggtc ttcccgctgg ccatgaacta cctggaccgc ttcctgtcgc   480
tggagcccgt gaaaaagagc cgcctgcagc tgctgggggc cacttgcatg ttcgtggcct   540
ctaagatgaa ggagaccatc cccctgacgg ccgagaagct gtgcatctac accgacaact   600
ccatccggcc cgaggagctg ctgcaaatgg agctgctcct ggtgaacaag ctcaagtgga   660
acctggccgc aatgaccccg cacgatttca ttgaacactt cctctccaaa atgccagagg   720
cggaggagaa caaacagatc atccgcaaac acgcgcagac cttcgttgcc ctctgtgcca   780
cagatgtgaa gttcatttcc aatccgccct ccatggtggc agcggggagc gtggtggccg   840
cagtgcaagg cctgaacctg aggagcccca caacttcct gtcctactac cgcctcacac   900
gcttcctctc cagagtgatc aagtgtgacc cggactgcct ccgggcctgc aggagcaga   960 tcgaagccct gctggagtca agcctgcgcc aggcccagca gaacatggac cccaaggccg   1020
ccgaggagga ggaagaggag gaggaggagg tggacctggc ttgcacaccc accgacgtgc   1080
gggacgtgga catctgaggg cgccaggcag gcgggcgcca ccgccacccg cagcgagggc   1140
ggagccggcc ccaggtgctc ccctgacagt ccctcctctc cggagcattt tgataccaga   1200
agggaaagct tcattctcct tgttgttggt tgttttttcc tttgctcttt cccccttcca   1260
tctctgactt aagcaaaaga aaagattac ccaaaaactg tctttaaaag agagagagag   1320
aaaaaaaaaa tagtatttgc ataaccctga gcggtggggg aggaggggttg tgctacagat   1380 gatagaggat tttataccc aataatcaac tcgttttat attaatgtac ttgtttctct   1440
gttgtaagaa taggcattaa cacaaaggag gcgtctcggg agaggattag gttccatcct   1500
ttacgtgttt aaaaaaaagc ataaaaacat tttaaaaaca tagaaaaatt cagcaaacca   1560
tttttaaagt agaagagggt tttaggtaga aaaacatatt cttgtgctttt tcctgataaa   1620 gcacagctgt agtgggttc taggcatctc tgtactttgc ttgctcatat gcatgtagtc   1680
actttataag tcattgtatg ttattatatt ccgtaggtag atgtgtaacc tcttcacctt   1740
attcatggct gaagtcacct cttggttaca gtagcgtagc gtgcccgtgt gcatgtcctt   1800
tgcgcctgtg accaccaccc caacaaacca tccagtgaca aaccatccag tggaggtttg   1860
tcgggcacca gccagcgtag cagggtcggg aaaggccacc tgtcccactc ctacgatacg   1920
ctactataaa gagaagacga aatagtgaca taatatattc tatttttata ctcttcctat   1980
ttttgtagtg acctgtttat gagatgctgg ttttctaccc aacggccctg cagccagctc   2040
acgtccaggt tcaacccaca gctacttggt ttgtgttctt cttcatattc taaaaccatt   2100
ccatttccaa gcactttcag tccaataggt gtaggaaata gcgctgtttt tgttgtgtgt   2160
gcagggaggg cagttttcta atggaatggt ttgggaatat ccatgtactt gtttgcaagc   2220
aggactttga ggcaagtgtg ggccactgtg gtggcagtgg aggtgggtg tttgggaggc   2280 tgcgtgccag tcaagaagaa aaaggtttgc attctcacat tgccaggatg ataagttcct   2340 ttcctttttct ttaaagaagt tgaagtttag gaatcctttg gtgccaactg gtgtttgaaa   2400
gtagggacct cagaggttta cctagagaac aggtggtttt taagggttat cttagatgtt   2460
tcacaccgga aggtttttaa acactaaaat atataattta tagttaaggc taaaaagtat   2520
atttattgca gaggatgttc ataaggccag tatgatttat aaatgcaatc tccccttgat   2580
```

| | | | | |
|---|---|---|---|---|
| ttaaacacac | agatacacac | acacacacac | acacacacaa | accttctgcc tttgatgtta | 2640 |
| cagatttaat | acagtttatt | tttaaagata | gatccttta | taggtgagaa aaaaacaatc | 2700 |
| tggaagaaaa | aaaccacaca | aagacattga | ttcagcctgt | ttggcgtttc ccagagtcat | 2760 |
| ctgattggac | aggcatgggt | gcaaggaaaa | ttagggtact | caacctaagt tcggttccga | 2820 |
| tgaattctta | tccccctgccc | cttccttaa | aaaacttagt | gacaaaatag acaatttgca | 2880 |
| catcttggct | atgtaattct | tgtaattttt | atttaggaag | tgttgaaggg aggtggcaag | 2940 |
| agtgtggagg | ctgacgtgtg | agggaggaca | ggcgggagga | ggtgtgagga ggaggctccc | 3000 |
| gaggggaagg | ggcggtgccc | acccggggga | caggccgcag | ctccattttc ttattgcgct | 3060 |
| gctaccgttg | acttccaggc | acggtttgga | aatattcaca | tcgcttctgt gtatctcttt | 3120 |
| cacattgttt | gctgctattg | gaggatcagt | tttttgtttt | acaatgtcat atactgccat | 3180 |
| gtactagttt | tagttttctc | ttagaacatt | gtattacaga | tgccttttt gtagtttttt | 3240 |
| tttttttat | gtgatcaatt | ttgacttaat | gtgattactg | ctctattcca aaaaggttgc | 3300 |
| tgtttcacaa | tacctcatgc | ttcacttagc | catggtggac | ccagcgggca ggttctgcct | 3360 |
| gctttggcgg | gcagacacgc | gggcgcgatc | ccacacaggc | tggcggggc cggccccgag | 3420 |
| gccgcgtgcg | tgagaaccgc | gccggtgtcc | ccagagacca | ggctgtgtcc ctcttctctt | 3480 |
| ccctgcgcct | gtgatgctgg | gcacttcatc | tgatcgggg | cgtagcatca tagtagtttt | 3540 |
| tacagctgtg | ttattctttg | cgtgtagcta | tggaagttgc | ataattatta ttattattat | 3600 |
| tataacaagt | gtgtcttacg | tgccaccacg | gcgttgtacc | tgtaggactc tcattcggga | 3660 |
| tgattggaat | agcttctgga | atttgttcaa | gttttgggta | tgtttaatct gttatgtact | 3720 |
| agtgttctgt | ttgttattgt | tttgttaatt | acaccataat | gctaatttaa agagactcca | 3780 |
| aatctcaatg | aagccagctc | acagtgctgt | gtgccccggt | cacctagcaa gctgccgaac | 3840 |
| caaaagaatt | tgcaccccgc | tgcgggccca | cgtggttggg | gccctgccct ggcagggtca | 3900 |
| tcctgtgctc | ggaggccatc | tcgggcacag | gcccaccccg | ccccacccct ccagaacacg | 3960 |
| gctcacgctt | acctcaacca | tcctggctgc | ggcgtctgtc | tgaaccacgc gggggccttg | 4020 |
| agggacgctt | tgtctgtcgt | gatggggcaa | gggcacaagt | cctggatgtt gtgtgtatcg | 4080 |
| agaggccaaa | ggctggtggc | aagtgcacgg | ggcacagcgg | agtctgtcct gtgacgcgca | 4140 |
| agtctgaggg | tctgggcggc | gggcggctgg | gtctgtgcat | ttctggttgc accgcggcgc | 4200 |
| ttcccagcac | caacatgtaa | ccggcatgtt | tccagcagaa | gacaaaaaga caaacatgaa | 4260 |
| agtctagaaa | taaaactggt | aaaaccccaa | aaaaaaaaa | aaaa | 4304 |

<210> SEQ ID NO 12
<211> LENGTH: 2820
<212> TYPE: DNA
<213> ORGANISM: Homo sapiens

<400> SEQUENCE: 12

| | | | | |
|---|---|---|---|---|
| gggagttcag | acctagatct | ttccagttaa | tcacacaaca | aacttagctc atcgcaataa | 60 |
| aaagcagctc | agagccgact | ggctcttta | ggcactgact | ccgaacagga ttcttttcacc | 120 |
| caggcatctc | ctccagaggg | atccgccagc | ccgtccagca | gcaccatgtg ggtgaccaaa | 180 |
| ctcctgccag | ccctgctgct | gcagcatgtc | tcctgcatc | tcctcctgct ccccatcgcc | 240 |
| atcccctatg | cagagggaca | aaggaaaaga | agaaatacaa | ttcatgaatt caaaaaatca | 300 |
| gcaaagacta | ccctaatcaa | aatagatcca | gcactgaaga | taaaaaccaa aaagtgaat | 360 |
| actgcagacc | aatgtgctaa | tagatgtact | aggaataaag | gacttccatt cacttgcaag | 420 |

```
gcttttgttt ttgataaagc aagaaaacaa tgcctctggt tccccttcaa tagcatgtca    480
agtggagtga aaaagaatt tggccatgaa tttgacctct atgaaaacaa agactacatt    540
agaaactgca tcattggtaa aggacgcagc tacaagggaa cagtatctat cactaagagt    600
ggcatcaaat gtcagccctg gagttccatg ataccacacg aacacagctt tttgccttcg    660
agctatcggg gtaaagacct acaggaaaac tactgtcgaa atcctcgagg ggaagaaggg    720
ggaccctggt gtttcacaag caatccagag gtacgctacg aagtctgtga cattcctcag    780
tgttcagaag ttgaatgcat gacctgcaat ggggagagtt atcgaggtct catggatcat    840
acagaatcag gcaagatttg tcagcgctgg gatcatcaga caccacaccg gcacaaattc    900
ttgcctgaaa gatatcccga caagggcttt gatgataatt attgccgcaa tcccgatggc    960
cagccgaggc catggtgcta tactcttgac cctcacaccc gctgggagta ctgtgcaatt   1020
aaaacatgcg ctgacaatac tatgaatgac actgatgttc ctttggaaac aactgaatgc   1080
atccaaggtc aaggagaagg ctacaggggc actgtcaata ccatttggaa tggaattcca   1140
tgtcagcgtt gggattctca gtatcctcac gagcatgaca tgactcctga aaatttcaag   1200
tgcaaggacc tacgagaaaa ttactgccga atccagatgg gtctgaatc  acctggtgt   1260 tttaccactg atccaaacat ccgagttggc tactgctccc aaattccaaa ctgtgatatg   1320
tcacatggac aagattgtta tcgtgggaat ggcaaaaatt atatgggcaa cttatcccaa   1380
acaagatctg gactaacatg ttcaatgtgg gacaagaaca tggaagactt acatcgtcat   1440
atcttctggg aaccagatgc aagtaagctg aatgagaatt actgccgaaa tccagatgat   1500
gatgctcatg gaccctggtg ctacacggga atccactca ttccttggga ttattgccct   1560
atttctcgtt gtgaaggtga taccacacct acaatagtca atttagacca tcccgtaata   1620
tcttgtgcca aaacgaaaca attgcgagtt gtaaatggga ttccaacacg aacaaacata   1680
ggatggatgg ttagtttgag atacagaaat aaacatatct gcggaggatc attgataaag   1740
gagagttggg ttcttactgc acgacagtgt ttcccttctc gagacttgaa agattatgaa   1800
gcttggcttg gaattcatga tgtccacgga agaggagatg agaaatgcaa acaggttctc   1860
aatgtttccc agctggtata tggccctgaa ggatcagatc tggttttaat gaagcttgcc   1920
aggcctgctg tcctggatga ttttgttagt acgattgatt tacctaatta tggatgcaca   1980
attcctgaaa agaccagttg cagtgtttat ggctggggct acactggatt gatcaactat   2040
gatggcctat tacgagtggc acatctctat ataatgggaa atgagaaatg cagccagcat   2100
catcgaggga aggtgactct gaatgagtct gaaaatgtg ctgggctga aaagattgga   2160 tcaggaccat gtgaggggga ttatggtggc ccacttgttt gtgagcaaca taaaatgaga   2220
atggttcttg gtgtcattgt tcctggtcgt ggatgtgcca ttccaaatcg tcctggtatt   2280
tttgtccgag tagcatatta tgcaaaatgg atacacaaaa ttattttaac atataaggta   2340
ccacagtcat agctgaagta agtgtgtctg aagcacccac caatacaact gtcttttaca   2400
tgaagatttc agagaatgtg aatttaaaaa tgtcacttac aacaatccta agacaactac   2460
tggagagtca tgtttgttga aattctcatt aatgtttatg ggtgttttct gttgttttgt   2520
ttgtcagtgt tattttgtca atgttgaagt gaattaaggt acatgcaagt gtaataacat   2580
atctcctgaa gatacttgaa tggattaaaa aaacacacag gtatatttgc tggatgataa   2640
agatttcatg ggaaaaaaaa tcaattaatc tgtctaagct gctttctgat gttggtttct   2700
taataatgag taaaccacaa attaaatgtt attttaacct caccaaaaca atttatacct   2760
tgtgtcccta aattgtagcc ctatattaaa ttatattaca tttcaaaaaa aaaaaaaaaa   2820
```

```
<210> SEQ ID NO 13
<211> LENGTH: 1132
<212> TYPE: PRT
<213> ORGANISM: Homo sapiens

<400> SEQUENCE: 13

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380
```

```
Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
            405                 410                 415

Ala Ala Val Thr Pro Ala Ala Gly Val Cys Ala Arg Glu Lys Pro Gln
        420                 425                 430

Gly Ser Val Ala Ala Pro Glu Glu Asp Thr Asp Pro Arg Arg Leu
    435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
            485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
            565                 570                 575

Arg Lys Ser Val Trp Ser Lys Leu Gln Ser Ile Gly Ile Arg Gln His
        580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
            645                 650                 655

Arg Val Lys Ala Leu Phe Ser Val Leu Asn Tyr Glu Arg Ala Arg Arg
        660                 665                 670

Pro Gly Leu Leu Gly Ala Ser Val Leu Gly Leu Asp Asp Ile His Arg
    675                 680                 685

Ala Trp Arg Thr Phe Val Leu Arg Val Arg Ala Gln Asp Pro Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735

Asn Thr Tyr Cys Val Arg Arg Tyr Ala Val Val Gln Lys Ala Ala His
        740                 745                 750

Gly His Val Arg Lys Ala Phe Lys Ser His Val Ser Thr Leu Thr Asp
    755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
            805                 810                 815
```

```
Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 14
<211> LENGTH: 580
<212> TYPE: PRT
<213> ORGANISM: Homo sapiens

<400> SEQUENCE: 14

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45
```

```
Leu Lys Trp Val Pro Glu Thr Pro Val Pro Gly Ser Asp Leu Gln Val
    50                  55                  60
Cys Leu Pro Lys Gly Pro Thr Cys Cys Ser Arg Lys Met Glu Glu Lys
65                  70                  75                  80
Tyr Gln Leu Thr Ala Arg Leu Asn Met Glu Gln Leu Leu Gln Ser Ala
                85                  90                  95
Ser Met Glu Leu Lys Phe Leu Ile Ile Gln Asn Ala Ala Val Phe Gln
            100                 105                 110
Glu Ala Phe Glu Ile Val Val Arg His Ala Lys Asn Tyr Thr Asn Ala
        115                 120                 125
Met Phe Lys Asn Asn Tyr Pro Ser Leu Thr Pro Gln Ala Phe Glu Phe
    130                 135                 140
Val Gly Glu Phe Phe Thr Asp Val Ser Leu Tyr Ile Leu Gly Ser Asp
145                 150                 155                 160
Ile Asn Val Asp Asp Met Val Asn Glu Leu Phe Asp Ser Leu Phe Pro
                165                 170                 175
Val Ile Tyr Thr Gln Leu Met Asn Pro Gly Leu Pro Asp Ser Ala Leu
            180                 185                 190
Asp Ile Asn Glu Cys Leu Arg Gly Ala Arg Arg Asp Leu Lys Val Phe
        195                 200                 205
Gly Asn Phe Pro Lys Leu Ile Met Thr Gln Val Ser Lys Ser Leu Gln
    210                 215                 220
Val Thr Arg Ile Phe Leu Gln Ala Leu Asn Leu Gly Ile Glu Val Ile
225                 230                 235                 240
Asn Thr Thr Asp His Leu Lys Phe Ser Lys Asp Cys Gly Arg Met Leu
                245                 250                 255
Thr Arg Met Trp Tyr Cys Ser Tyr Cys Gln Gly Leu Met Met Val Lys
            260                 265                 270
Pro Cys Gly Gly Tyr Cys Asn Val Val Met Gln Gly Cys Met Ala Gly
        275                 280                 285
Val Val Glu Ile Asp Lys Tyr Trp Arg Glu Tyr Ile Leu Ser Leu Glu
    290                 295                 300
Glu Leu Val Asn Gly Met Tyr Arg Ile Tyr Asp Met Glu Asn Val Leu
305                 310                 315                 320
Leu Gly Leu Phe Ser Thr Ile His Asp Ser Ile Gln Tyr Val Gln Lys
                325                 330                 335
Asn Ala Gly Lys Leu Thr Thr Thr Ile Gly Lys Leu Cys Ala His Ser
            340                 345                 350
Gln Gln Arg Gln Tyr Arg Ser Ala Tyr Tyr Pro Glu Asp Leu Phe Ile
        355                 360                 365
Asp Lys Lys Val Leu Lys Val Ala His Val Glu His Glu Glu Thr Leu
    370                 375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                405                 410                 415
Glu Asn Asp Thr Leu Cys Trp Asn Gly Gln Glu Leu Val Glu Arg Tyr
            420                 425                 430
Ser Gln Lys Ala Ala Arg Asn Gly Met Lys Asn Gln Phe Asn Leu His
        435                 440                 445
Glu Leu Lys Met Lys Gly Pro Glu Pro Val Val Ser Gln Ile Ile Asp
    450                 455                 460
Lys Leu Lys His Ile Asn Gln Leu Leu Arg Thr Met Ser Met Pro Lys
```

```
                465                 470                 475                 480
Gly Arg Val Leu Asp Lys Asn Leu Asp Glu Glu Gly Phe Glu Ser Gly
                    485                 490                 495

Asp Cys Gly Asp Asp Glu Asp Glu Cys Ile Gly Gly Ser Gly Asp Gly
                500                 505                 510

Met Ile Lys Val Lys Asn Gln Leu Arg Phe Leu Ala Glu Leu Ala Tyr
            515                 520                 525

Asp Leu Asp Val Asp Ala Pro Gly Asn Ser Gln Gln Ala Thr Pro
        530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 15
<211> LENGTH: 151
<212> TYPE: PRT
<213> ORGANISM: Homo sapiens

<400> SEQUENCE: 15

Met Glu Gly Cys Val Ser Asn Leu Met Val Cys Asn Leu Ala Tyr Ser
1               5                   10                  15

Gly Lys Leu Glu Glu Leu Lys Glu Ser Ile Leu Ala Asp Lys Ser Leu
            20                  25                  30

Ala Thr Arg Thr Asp Gln Asp Ser Arg Thr Ala Leu His Trp Ala Cys
        35                  40                  45

Ser Ala Gly His Thr Glu Ile Val Glu Phe Leu Gln Leu Gly Val
    50                  55                  60

Pro Val Asn Asp Lys Asp Asp Ala Gly Trp Ser Pro Leu His Ile Ala
65                  70                  75                  80

Ala Ser Ala Gly Arg Asp Glu Ile Val Lys Ala Leu Leu Gly Lys Gly
                85                  90                  95

Ala Gln Val Asn Ala Val Asn Gln Asn Gly Cys Thr Pro Leu His Tyr
            100                 105                 110

Ala Ala Ser Lys Asn Arg His Glu Ile Ala Val Met Leu Leu Glu Gly
        115                 120                 125

Gly Ala Asn Pro Asp Ala Lys Asp His Tyr Glu Ala Thr Ala Met His
    130                 135                 140

Arg Ala Ala Ala Lys Asp Thr
145                 150

<210> SEQ ID NO 16
<211> LENGTH: 142
<212> TYPE: PRT
<213> ORGANISM: Homo sapiens

<400> SEQUENCE: 16

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60
```

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140

<210> SEQ ID NO 17
<211> LENGTH: 1531
<212> TYPE: PRT
<213> ORGANISM: Homo sapiens

<400> SEQUENCE: 17

Met Glu Val Ser Pro Leu Gln Pro Val Asn Glu Asn Met Gln Val Asn
1               5                   10                  15

Lys Ile Lys Lys Asn Glu Asp Ala Lys Lys Arg Leu Ser Val Glu Arg
            20                  25                  30

Ile Tyr Gln Lys Lys Thr Gln Leu Glu His Ile Leu Leu Arg Pro Asp
        35                  40                  45

Thr Tyr Ile Gly Ser Val Glu Leu Val Thr Gln Gln Met Trp Val Tyr
    50                  55                  60

Asp Glu Asp Val Gly Ile Asn Tyr Arg Glu Val Thr Phe Val Pro Gly
65                  70                  75                  80

Leu Tyr Lys Ile Phe Asp Glu Ile Leu Val Asn Ala Ala Asp Asn Lys
                85                  90                  95

Gln Arg Asp Pro Lys Met Ser Cys Ile Arg Val Thr Ile Asp Pro Glu
            100                 105                 110

Asn Asn Leu Ile Ser Ile Trp Asn Asn Gly Lys Gly Ile Pro Val Val
        115                 120                 125

Glu His Lys Val Glu Lys Met Tyr Val Pro Ala Leu Ile Phe Gly Gln
    130                 135                 140

Leu Leu Thr Ser Ser Asn Tyr Asp Asp Asp Glu Lys Lys Val Thr Gly
145                 150                 155                 160

Gly Arg Asn Gly Tyr Gly Ala Lys Leu Cys Asn Ile Phe Ser Thr Lys
                165                 170                 175

Phe Thr Val Glu Thr Ala Ser Arg Glu Tyr Lys Lys Met Phe Lys Gln
            180                 185                 190

Thr Trp Met Asp Asn Met Gly Arg Ala Gly Glu Met Glu Leu Lys Pro
        195                 200                 205

Phe Asn Gly Glu Asp Tyr Thr Cys Ile Thr Phe Gln Pro Asp Leu Ser
    210                 215                 220

Lys Phe Lys Met Gln Ser Leu Asp Lys Asp Ile Val Ala Leu Met Val
225                 230                 235                 240

Arg Arg Ala Tyr Asp Ile Ala Gly Ser Thr Lys Asp Val Lys Val Phe
                245                 250                 255

Leu Asn Gly Asn Lys Leu Pro Val Lys Gly Phe Arg Ser Tyr Val Asp
            260                 265                 270

Met Tyr Leu Lys Asp Lys Leu Asp Glu Thr Gly Asn Ser Leu Lys Val
        275                 280                 285

Ile His Glu Gln Val Asn His Arg Trp Glu Val Cys Leu Thr Met Ser
    290                 295                 300

-continued

```
Glu Lys Gly Phe Gln Gln Ile Ser Phe Val Asn Ser Ile Ala Thr Ser
305                 310                 315                 320
Lys Gly Gly Arg His Val Asp Tyr Val Ala Asp Gln Ile Val Thr Lys
            325                 330                 335
Leu Val Asp Val Val Lys Lys Asn Lys Gly Gly Val Ala Val Lys
        340                 345                 350
Ala His Gln Val Lys Asn His Met Trp Ile Phe Val Asn Ala Leu Ile
    355                 360                 365
Glu Asn Pro Thr Phe Asp Ser Gln Thr Lys Glu Asn Met Thr Leu Gln
370                 375                 380
Pro Lys Ser Phe Gly Ser Thr Cys Gln Leu Ser Glu Lys Phe Ile Lys
385                 390                 395                 400
Ala Ala Ile Gly Cys Gly Ile Val Glu Ser Ile Leu Asn Trp Val Lys
                405                 410                 415
Phe Lys Ala Gln Val Gln Leu Asn Lys Lys Cys Ser Ala Val Lys His
            420                 425                 430
Asn Arg Ile Lys Gly Ile Pro Lys Leu Asp Asp Ala Asn Asp Ala Gly
        435                 440                 445
Gly Arg Asn Ser Thr Glu Cys Thr Leu Ile Leu Thr Glu Gly Asp Ser
450                 455                 460
Ala Lys Thr Leu Ala Val Ser Gly Leu Gly Val Val Gly Arg Asp Lys
465                 470                 475                 480
Tyr Gly Val Phe Pro Leu Arg Gly Lys Ile Leu Asn Val Arg Glu Ala
                485                 490                 495
Ser His Lys Gln Ile Met Glu Asn Ala Glu Ile Asn Asn Ile Ile Lys
            500                 505                 510
Ile Val Gly Leu Gln Tyr Lys Lys Asn Tyr Glu Asp Glu Asp Ser Leu
        515                 520                 525
Lys Thr Leu Arg Tyr Gly Lys Ile Met Ile Met Thr Asp Gln Asp Gln
530                 535                 540
Asp Gly Ser His Ile Lys Gly Leu Leu Ile Asn Phe Ile His His Asn
545                 550                 555                 560
Trp Pro Ser Leu Leu Arg His Arg Phe Leu Glu Glu Phe Ile Thr Pro
                565                 570                 575
Ile Val Lys Val Ser Lys Asn Lys Gln Glu Met Ala Phe Tyr Ser Leu
            580                 585                 590
Pro Glu Phe Glu Glu Trp Lys Ser Ser Thr Pro Asn His Lys Lys Trp
        595                 600                 605
Lys Val Lys Tyr Tyr Lys Gly Leu Gly Thr Ser Thr Ser Lys Glu Ala
610                 615                 620
Lys Glu Tyr Phe Ala Asp Met Lys Arg His Arg Ile Gln Phe Lys Tyr
625                 630                 635                 640
Ser Gly Pro Glu Asp Asp Ala Ala Ile Ser Leu Ala Phe Ser Lys Lys
                645                 650                 655
Gln Ile Asp Asp Arg Lys Glu Trp Leu Thr Asn Phe Met Glu Asp Arg
            660                 665                 670
Arg Gln Arg Lys Leu Leu Gly Leu Pro Glu Asp Tyr Leu Tyr Gly Gln
        675                 680                 685
Thr Thr Thr Tyr Leu Thr Tyr Asn Asp Phe Ile Asn Lys Glu Leu Ile
690                 695                 700
Leu Phe Ser Asn Ser Asp Asn Glu Arg Ser Ile Pro Ser Met Val Asp
705                 710                 715                 720
Gly Leu Lys Pro Gly Gln Arg Lys Val Leu Phe Thr Cys Phe Lys Arg
```

-continued

```
                725                 730                 735
Asn Asp Lys Arg Glu Val Lys Val Ala Gln Leu Ala Gly Ser Val Ala
            740                 745                 750

Glu Met Ser Ser Tyr His His Gly Glu Met Ser Leu Met Met Thr Ile
            755                 760                 765

Ile Asn Leu Ala Gln Asn Phe Val Gly Ser Asn Asn Leu Asn Leu Leu
            770                 775                 780

Gln Pro Ile Gly Gln Phe Gly Thr Arg Leu His Gly Gly Lys Asp Ser
785                 790                 795                 800

Ala Ser Pro Arg Tyr Ile Phe Thr Met Leu Ser Ser Leu Ala Arg Leu
                805                 810                 815

Leu Phe Pro Pro Lys Asp Asp His Thr Leu Lys Phe Leu Tyr Asp Asp
                820                 825                 830

Asn Gln Arg Val Glu Pro Glu Trp Tyr Ile Pro Ile Pro Met Val
                835                 840                 845

Leu Ile Asn Gly Ala Glu Gly Ile Gly Thr Gly Trp Ser Cys Lys Ile
            850                 855                 860

Pro Asn Phe Asp Val Arg Glu Ile Val Asn Asn Ile Arg Arg Leu Met
865                 870                 875                 880

Asp Gly Glu Glu Pro Leu Pro Met Leu Pro Ser Tyr Lys Asn Phe Lys
                885                 890                 895

Gly Thr Ile Glu Glu Leu Ala Pro Asn Gln Tyr Val Ile Ser Gly Glu
            900                 905                 910

Val Ala Ile Leu Asn Ser Thr Thr Ile Glu Ile Ser Glu Leu Pro Val
            915                 920                 925

Arg Thr Trp Thr Gln Thr Tyr Lys Glu Gln Val Leu Glu Pro Met Leu
        930                 935                 940

Asn Gly Thr Glu Lys Thr Pro Pro Leu Ile Thr Asp Tyr Arg Glu Tyr
945                 950                 955                 960

His Thr Asp Thr Thr Val Lys Phe Val Val Lys Met Thr Glu Glu Lys
                965                 970                 975

Leu Ala Glu Ala Glu Arg Val Gly Leu His Lys Val Phe Lys Leu Gln
            980                 985                 990

Thr Ser Leu Thr Cys Asn Ser Met Val Leu Phe Asp His Val Gly Cys
        995                 1000                1005

Leu Lys Lys Tyr Asp Thr Val Leu Asp Ile Leu Arg Asp Phe Phe
    1010                1015                1020

Glu Leu Arg Leu Lys Tyr Tyr Gly Leu Arg Lys Glu Trp Leu Leu
    1025                1030                1035

Gly Met Leu Gly Ala Glu Ser Ala Lys Leu Asn Asn Gln Ala Arg
    1040                1045                1050

Phe Ile Leu Glu Lys Ile Asp Gly Lys Ile Ile Ile Glu Asn Lys
    1055                1060                1065

Pro Lys Lys Glu Leu Ile Lys Val Leu Ile Gln Arg Gly Tyr Asp
    1070                1075                1080

Ser Asp Pro Val Lys Ala Trp Lys Glu Ala Gln Gln Lys Val Pro
    1085                1090                1095

Asp Glu Glu Glu Asn Glu Glu Ser Asp Asn Glu Lys Glu Thr Glu
    1100                1105                1110

Lys Ser Asp Ser Val Thr Asp Ser Gly Pro Thr Phe Asn Tyr Leu
    1115                1120                1125

Leu Asp Met Pro Leu Trp Tyr Leu Thr Lys Glu Lys Lys Asp Glu
    1130                1135                1140
```

```
Leu Cys Arg Leu Arg Asn Glu Lys Glu Gln Glu Leu Asp Thr Leu
1145                1150                1155

Lys Arg Lys Ser Pro Ser Asp Leu Trp Lys Glu Asp Leu Ala Thr
1160                1165                1170

Phe Ile Glu Glu Leu Glu Ala Val Glu Ala Lys Glu Lys Gln Asp
1175                1180                1185

Glu Gln Val Gly Leu Pro Gly Lys Gly Lys Ala Lys Gly Lys
1190                1195                1200

Lys Thr Gln Met Ala Glu Val Leu Pro Ser Pro Arg Gly Gln Arg
1205                1210                1215

Val Ile Pro Arg Ile Thr Ile Glu Met Lys Ala Glu Ala Glu Lys
1220                1225                1230

Lys Asn Lys Lys Lys Ile Lys Asn Glu Asn Thr Glu Gly Ser Pro
1235                1240                1245

Gln Glu Asp Gly Val Glu Leu Glu Gly Leu Lys Gln Arg Leu Glu
1250                1255                1260

Lys Lys Gln Lys Arg Glu Pro Gly Thr Lys Thr Lys Lys Gln Thr
1265                1270                1275

Thr Leu Ala Phe Lys Pro Ile Lys Lys Gly Lys Lys Arg Asn Pro
1280                1285                1290

Trp Ser Asp Ser Glu Ser Asp Arg Ser Ser Asp Glu Ser Asn Phe
1295                1300                1305

Asp Val Pro Pro Arg Glu Thr Glu Pro Arg Arg Ala Ala Thr Lys
1310                1315                1320

Thr Lys Phe Thr Met Asp Leu Asp Ser Asp Glu Asp Phe Ser Asp
1325                1330                1335

Phe Asp Glu Lys Thr Asp Asp Glu Asp Phe Val Pro Ser Asp Ala
1340                1345                1350

Ser Pro Pro Lys Thr Lys Thr Ser Pro Lys Leu Ser Asn Lys Glu
1355                1360                1365

Leu Lys Pro Gln Lys Ser Val Val Ser Asp Leu Glu Ala Asp Asp
1370                1375                1380

Val Lys Gly Ser Val Pro Leu Ser Ser Ser Pro Ala Thr His
1385                1390                1395

Phe Pro Asp Glu Thr Glu Ile Thr Asn Pro Val Pro Lys Lys Asn
1400                1405                1410

Val Thr Val Lys Lys Thr Ala Ala Lys Ser Gln Ser Ser Thr Ser
1415                1420                1425

Thr Thr Gly Ala Lys Lys Arg Ala Ala Pro Lys Gly Thr Lys Arg
1430                1435                1440

Asp Pro Ala Leu Asn Ser Gly Val Ser Gln Lys Pro Asp Pro Ala
1445                1450                1455

Lys Thr Lys Asn Arg Arg Lys Arg Lys Pro Ser Thr Ser Asp Asp
1460                1465                1470

Ser Asp Ser Asn Phe Glu Lys Ile Val Ser Lys Ala Val Thr Ser
1475                1480                1485

Lys Lys Ser Lys Gly Glu Ser Asp Asp Phe His Met Asp Phe Asp
1490                1495                1500

Ser Ala Val Ala Pro Arg Ala Lys Ser Val Arg Ala Lys Lys Pro
1505                1510                1515

Ile Lys Tyr Leu Glu Glu Ser Asp Glu Asp Asp Leu Phe
1520                1525                1530

<210> SEQ ID NO 18
```

<211> LENGTH: 322
<212> TYPE: PRT
<213> ORGANISM: Homo sapiens

<400> SEQUENCE: 18

```
Met Ala Arg Cys Phe Ser Leu Val Leu Leu Thr Ser Ile Trp Thr
1               5                   10                  15

Thr Arg Leu Leu Val Gln Gly Ser Leu Arg Ala Glu Glu Leu Ser Ile
            20                  25                  30

Gln Val Ser Cys Arg Ile Met Gly Ile Thr Leu Val Ser Lys Lys Ala
            35                  40                  45

Asn Gln Gln Leu Asn Phe Thr Glu Ala Lys Glu Ala Cys Arg Leu Leu
        50                  55                  60

Gly Leu Ser Leu Ala Gly Lys Asp Gln Val Glu Thr Ala Leu Lys Ala
65                  70                  75                  80

Ser Phe Glu Thr Cys Ser Tyr Gly Trp Val Gly Asp Gly Phe Val Val
                85                  90                  95

Ile Ser Arg Ile Ser Pro Asn Pro Lys Cys Gly Lys Asn Gly Val Gly
                100                 105                 110

Val Leu Ile Trp Lys Val Pro Val Ser Arg Gln Phe Ala Ala Tyr Cys
                115                 120                 125

Tyr Asn Ser Ser Asp Thr Trp Thr Asn Ser Cys Ile Pro Glu Ile Ile
130                 135                 140

Thr Thr Lys Asp Pro Ile Phe Asn Thr Gln Thr Ala Thr Gln Thr Thr
145                 150                 155                 160

Glu Phe Ile Val Ser Asp Ser Thr Tyr Ser Val Ala Ser Pro Tyr Ser
                165                 170                 175

Thr Ile Pro Ala Pro Thr Thr Thr Pro Pro Ala Pro Ala Ser Thr Ser
                180                 185                 190

Ile Pro Arg Arg Lys Lys Leu Ile Cys Val Thr Glu Val Phe Met Glu
                195                 200                 205

Thr Ser Thr Met Ser Thr Glu Thr Glu Pro Phe Val Glu Asn Lys Ala
210                 215                 220

Ala Phe Lys Asn Glu Ala Ala Gly Phe Gly Gly Val Pro Thr Ala Leu
225                 230                 235                 240

Leu Val Leu Ala Leu Leu Phe Phe Gly Ala Ala Ala Gly Leu Gly Phe
                245                 250                 255

Cys Tyr Val Lys Arg Tyr Val Lys Ala Phe Pro Phe Thr Asn Lys Asn
                260                 265                 270

Gln Gln Lys Glu Met Ile Glu Thr Lys Val Val Lys Glu Glu Lys Ala
                275                 280                 285

Asn Asp Ser Asn Pro Asn Glu Glu Ser Lys Lys Thr Asp Lys Asn Pro
            290                 295                 300

Glu Glu Ser Lys Ser Pro Ser Lys Thr Thr Val Arg Cys Leu Glu Ala
305                 310                 315                 320

Glu Val
```

<210> SEQ ID NO 19
<211> LENGTH: 882
<212> TYPE: PRT
<213> ORGANISM: Homo sapiens

<400> SEQUENCE: 19

```
Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
```

```
                    20                  25                  30
Asp Ala Glu Ser Tyr Thr Phe Thr Val Pro Arg Arg His Leu Glu Arg
            35                  40                  45

Gly Arg Val Leu Gly Arg Val Asn Phe Glu Asp Cys Thr Gly Arg Gln
        50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro His
        115                 120                 125

Gln Ala Ser Val Ser Gly Ile Gln Ala Glu Leu Leu Thr Phe Pro Asn
        130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
        210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
        290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
        370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445
```

```
Gln Tyr Ile Leu His Val Ala Val Thr Asn Val Val Pro Phe Glu Val
            450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                    485                 490                 495

Glu Asp Phe Gly Val Gly Gln Glu Ile Thr Ser Tyr Thr Ala Gln Glu
                500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
                580                 585                 590

Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
            610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
                660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
            690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Leu Phe Leu Arg Arg Arg Ala Val
                725                 730                 735

Val Lys Glu Pro Leu Leu Pro Pro Glu Asp Asp Thr Arg Asp Asn Val
                740                 745                 750

Tyr Tyr Tyr Asp Glu Glu Gly Gly Glu Glu Asp Gln Asp Phe Asp
                755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                    805                 810                 815

Ala Ala Asp Thr Asp Pro Thr Ala Pro Pro Tyr Asp Ser Leu Leu Val
                820                 825                 830

Phe Asp Tyr Glu Gly Ser Gly Ser Glu Ala Ala Ser Leu Ser Ser Leu
                835                 840                 845

Asn Ser Ser Glu Ser Asp Lys Asp Gln Asp Tyr Asp Tyr Leu Asn Glu
                850                 855                 860

Trp Gly Asn Arg Phe Lys Lys Leu Ala Asp Met Tyr Gly Gly Gly Glu
865                 870                 875                 880
```

Asp Asp

<210> SEQ ID NO 20
<211> LENGTH: 291
<212> TYPE: PRT
<213> ORGANISM: Homo sapiens

<400> SEQUENCE: 20

Met Gln Arg Ala Arg Pro Thr Leu Trp Ala Ala Leu Thr Leu Leu
1               5                   10                  15

Val Leu Leu Arg Gly Pro Pro Val Ala Arg Ala Gly Ser Ser Ala
                20                  25                  30

Gly Leu Gly Pro Val Val Arg Cys Glu Pro Cys Asp Ala Arg Ala Leu
                35                  40                  45

Ala Gln Cys Ala Pro Pro Ala Val Cys Ala Glu Leu Val Arg Glu
        50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
                100                 105                 110

Leu Cys Val Asn Ala Ser Ala Val Ser Arg Leu Arg Ala Tyr Leu Leu
                115                 120                 125

Pro Ala Pro Pro Ala Pro Gly Asn Ala Ser Glu Ser Glu Glu Asp Arg
        130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Lys
                165                 170                 175

Lys Gly His Ala Lys Asp Ser Gln Arg Tyr Lys Val Asp Tyr Glu Ser
                180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
                260                 265                 270

Pro Gly Tyr Thr Thr Lys Gly Lys Glu Asp Val His Cys Tyr Ser Met
        275                 280                 285

Gln Ser Lys
        290

<210> SEQ ID NO 21
<211> LENGTH: 1089
<212> TYPE: PRT
<213> ORGANISM: Homo sapiens

<400> SEQUENCE: 21

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro

```
                    20                  25                  30
Asn Glu Asn Glu Lys Val Val Gln Leu Asn Ser Ser Phe Ser Leu Arg
                35                  40                  45
Cys Phe Gly Glu Ser Glu Val Ser Trp Gln Tyr Pro Met Ser Glu Glu
         50                  55                  60
Glu Ser Ser Asp Val Glu Ile Arg Asn Glu Glu Asn Asn Ser Gly Leu
 65                  70                  75                  80
Phe Val Thr Val Leu Glu Val Ser Ser Ala Ser Ala Ala His Thr Gly
                 85                  90                  95
Leu Tyr Thr Cys Tyr Tyr Asn His Thr Gln Thr Glu Glu Asn Glu Leu
                100                 105                 110
Glu Gly Arg His Ile Tyr Ile Tyr Val Pro Asp Pro Asp Val Ala Phe
                115                 120                 125
Val Pro Leu Gly Met Thr Asp Tyr Leu Val Ile Val Glu Asp Asp Asp
                130                 135                 140
Ser Ala Ile Ile Pro Cys Arg Thr Thr Asp Pro Glu Thr Pro Val Thr
145                 150                 155                 160
Leu His Asn Ser Glu Gly Val Val Pro Ala Ser Tyr Asp Ser Arg Gln
                165                 170                 175
Gly Phe Asn Gly Thr Phe Thr Val Gly Pro Tyr Ile Cys Glu Ala Thr
                180                 185                 190
Val Lys Gly Lys Lys Phe Gln Thr Ile Pro Phe Asn Val Tyr Ala Leu
                195                 200                 205
Lys Ala Thr Ser Glu Leu Asp Leu Glu Met Glu Ala Leu Lys Thr Val
                210                 215                 220
Tyr Lys Ser Gly Glu Thr Ile Val Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Met Leu Glu Glu Ile Lys Val Pro Ser Ile Lys Leu Val
                260                 265                 270
Tyr Thr Leu Thr Val Pro Glu Ala Thr Val Lys Asp Ser Gly Asp Tyr
                275                 280                 285
Glu Cys Ala Ala Arg Gln Ala Thr Arg Glu Val Lys Glu Met Lys Lys
                290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Pro Arg Ile Ser Trp Leu Lys Asn
                340                 345                 350
Asn Leu Thr Leu Ile Glu Asn Leu Thr Glu Ile Thr Thr Asp Val Glu
                355                 360                 365
Lys Ile Gln Glu Ile Arg Tyr Arg Ser Lys Leu Lys Leu Ile Arg Ala
                370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gln Thr
                420                 425                 430
Val Arg Cys Thr Ala Glu Gly Thr Pro Leu Pro Asp Ile Glu Trp Met
                435                 440                 445
```

```
Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ser Leu Ile Val
530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
        610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
                740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
                820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880
```

```
Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
                915                 920                 925

Met Val Lys Cys Trp Asn Ser Glu Pro Glu Lys Arg Pro Ser Phe Tyr
        930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
                980                 985                 990

Tyr Lys Asn Glu Glu Asp Lys Leu Lys Asp Trp Glu Gly Gly Leu Asp
            995                 1000                1005

Glu Gln Arg Leu Ser Ala Asp Ser Gly Tyr Ile Ile Pro Leu Pro
        1010                1015                1020

Asp Ile Asp Pro Val Pro Glu Glu Asp Leu Gly Lys Arg Asn
    1025                1030                1035

Arg His Ser Ser Gln Thr Ser Glu Glu Ser Ala Ile Glu Thr Gly
        1040                1045                1050

Ser Ser Ser Ser Thr Phe Ile Lys Arg Glu Asp Glu Thr Ile Glu
    1055                1060                1065

Asp Ile Asp Met Met Asp Asp Ile Gly Ile Asp Ser Ser Asp Leu
    1070                1075                1080

Val Glu Asp Ser Phe Leu
    1085

<210> SEQ ID NO 22
<211> LENGTH: 160
<212> TYPE: PRT
<213> ORGANISM: Homo sapiens

<400> SEQUENCE: 22

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Pro Val Ala Ala Ala Val Ser His Phe Asn Asp Cys Pro
        35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Ala Ala Ser Gln Lys
                85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
        115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145                 150                 155                 160
```

<210> SEQ ID NO 23
<211> LENGTH: 295
<212> TYPE: PRT
<213> ORGANISM: Homo sapiens

<400> SEQUENCE: 23

```
Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
        275                 280                 285

Asp Val Arg Asp Val Asp Ile
    290                 295
```

<210> SEQ ID NO 24
<211> LENGTH: 728
<212> TYPE: PRT
<213> ORGANISM: Homo sapiens

<400> SEQUENCE: 24

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30
```

```
Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
            130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
            290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
            370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
            450                 455                 460
```

-continued

```
Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

METHODS AND COMPOSITIONS FOR THE DIAGNOSIS FOR EARLY HEPATOCELLULAR CARCINOMA

The present application claims the benefit of priority of U.S. Provisional Application No. 60/792,166 which was filed Apr. 14, 2006. The entire text of the aforementioned application is incorporated herein by reference.

STATEMENT OF GOVERNMENT FUNDING

The studies described herein were performed in part using Government funding in the form of a grant from the National Institute of Health grant number DK37340.

BACKGROUND

Hepatocellular carcinoma (HCC), a malignant tumor of the liver, is a major health problem (Llovet et al., Lancet, 362: 1907-1917 (2003)). It is the third leading cause of cancer-related death in the world, and its incidence is increasing in Europe and the US. HCC is now the leading cause of death among cirrhotic patients and accounts for 80% to 90% of all liver cancers. It occurs more often in men than women and occurs mostly in people 50 to 60 years old. The disease is more common in parts of Africa and Asia than in North or South America and Europe.

The cause of liver cancer is usually cirrhosis, or scarring of the liver. Cirrhosis may be caused by viral hepatitis, primarily hepatitis B and C, alcohol abuse, hemochromatosis, certain autoimmune diseases of the liver, and a whole host of other diseases that result in chronic inflammation of the liver leading to scarring. While in the U.S. the most common cause for cirrhosis is alcohol abuse, globally, HCV infection is the most prevalent etiology of HCC in Europe, US and Japan (Bosch et al., Gastroenterology, 127(5 Suppl 1):S5-S16 (2004)). HCC is notoriously refractory to treatment. Typically, chemotherapy and radiation treatments are not usually effective but may be used to shrink large tumors so that surgery has a greater chance of success. In some instances, where the tumors are small or slow-growing, surgery or liver transplantation may be successful. However, liver transplant is only effective if such small or slow-growing tumors are diagnosed early in the course of the disease.

Nevertheless, as a result of screening programs in the West and Japan, early diagnosis of HCC is now feasible in 30-60% of cases, enabling the application of curative treatments (Llovet et al., Lancet, 362:1907-1917 (2003); Sangiovanni et al., Gastroenterology, 126(4):1005-1014 (2004)). Simultaneously, however, an increasing number of small nodules of ~2 cm are detected, which are difficult to characterize by imaging techniques or conventional pathologic examination (Ikai et al., Cancer, 101:796-802 (2004); Bolondi et al., Hepatology, 42:27-34 (2005); Kojiro et al., Liver Transpl., 10(2 Suppl 1):S3-S8 (2004)).

Distinguishing pre-neoplastic lesions, particularly high grade dysplastic nodules (HGDN), from early tumors is an unresolved challenge. Expert hepatopathologists often disagree about the final diagnosis of early tumors, some of which are misclassified as dysplastic nodules, a situation that is estimated to be especially common in non-expert hands (Kojiro et al., Liver Transpl., 10(2 Suppl 1):S3-S8 (2004)). Immunostaining with CD34 and alpha fetoprotein (AFP) has significant diagnostic limitations (Park et al., Am. J. Surg. Pathol., 22:656-662 (1998)). Nonetheless, pathology is considered the gold-standard of diagnosis. Non-invasive radiological criteria have been developed by using state-of-the art imaging techniques, such as contrastenhanced ultrasonography, helical computed tomography or magnetic resonance imaging (Bruix et al., J. Hepatol., 35:421-430 (2001); Burrel et al., Hepatology, 38:1034-1042 (2003)). However, reliable diagnosis is confined almost entirely to tumors exceeding 2 cm in diameter (Lencioni et al., J. Hepatol., 40:162-171 (2004)). Finally, serum biomarkers such as AFP, desgamma-carboxyprothrombin (DGCP) and AFP-L3 fraction are currently not reliable for the early diagnosis of HCC (Bruix et al., Hepatology, 42:1208-1236 (2005); Marrero et al., Gastroenterology, 127(5 Suppl 1):S113-S119 (2004)).

There is a clear distinction between tissue biomarkers and serum biomarkers. Tissue markers should be able to distinguish early HCC from other entities (preneoplastic lesions, cirrhotic tissue and other neoplasms). Eventually, some of them may be further tested as serum markers for surveillance purposes, as defined by the Early Detection Research Network of the National Cancer Institute (Marrero et al., Gastroenterology, 127(5 Suppl 1):S113-S119 (2004)). A variety of genomic studies using genome-wide DNA microarray or quantitative real time reverse-transcriptase polymerase chain reaction (RT-PCR) have attempted to identify markers of early HCC, including heat shock protein 70 (HSP70) (Chuma et al., Hepatology, 37:198-207 (2003)), Glypican-3 (GPC3) (Capurro et al., Gastroenterology, 125:89-97 (2003); Nakatsura et al., Biochem. Biophys. Res. Commun., 306:16-25 (2003); Hippo et al., Cancer Res., 64:2418-2423 (2004)), telomerase reverse transcriptase (TERT) (Smith et al., Cancer Res., 63:859-864 (2003)), serine/threonine kinase 15 (STK6) and phospholipase A2 (PLAG12B) (Paradis et al., Am. J. Pathol., 163:733-741 (2003)). A molecular index including a 13-gene set has also been proposed (including TERT, TOP2A and PDGFRA) (Nam et al., Hepatology, 42:809-818 (2005)). More recently a microarray-generated signature of 120 genes was reported to discriminate between dysplastic nodules and HCC in HBV patients (Paradis et al., Hepatology, 41:40-47 (2005)). Proteomic studies in tissue have not identified informative HCC markers so far (Borzio et al., J. Hepatol., 39:208-214 (2003)).

A major limitation of these studies, however, has been the comparison between the gene expression of cancer with nontumoral cirrhotic tissue. Data regarding gene expression in dysplastic nodules and early HCC is scarce, and direct comparisons are lacking in HCV patients. Overall, an ideal candidate set of genes has not been identified, and none of the reported genes or signatures is accepted as a molecular marker in standardized guidelines of HCC management (Bruix et al., J. Hepatol., 35:421-430 (2001); Bruix et al., Hepatology, 42:1208-1236 (2005)). Distinction between pre-neoplastic nodules and early small tumors has critical clinical implications. According to the management guidelines of HCC in Europe and the US (Bruix et al., J. Hepatol., 35:421-430 (2001); Bruix et al., Hepatology, 42:1208-1236 (2005)), dysplastic lesions should be followed by regular imaging studies, since approximately one-third of them will develop a malignant phenotype, with the remaining nodules either disappearing or remaining stable for years (Terasaki et al., Gastroenterology, 115:1216-1222 (1998); Kojiro et al., Semin. Liv. Dis., 25:133-142 (2005)). Malignant transformation from low-grade dysplastic nodules is less evident, although these are the precursors of HGDN (Llovet et al., Semin. Liver Dis., 25:181-200 (2005)). On the other hand, early small tumors are the ideal targets for curative treatments such as resection, transplantation and percutaneous ablation that can provide median survivals exceeding 60 months (Llovet et al., Lancet, 362:1907-1917 (2003); International Working Party, Hepatology, 17:27-35 (1995)). Thus, there is an urgent need to identify better tools to characterize these lesions. In the absence of addressing this need, the cost-effectiveness of the recall policies applied within surveillance programs will be significantly undermined.

SUMMARY OF THE INVENTION

In the present invention, transcriptional profiles are provided to allow discrimination of dysplastic nodules from early cancers in patients with hepatitis infection. More particularly, transcriptional profiles of at least 3, and more particularly at least 5 genes has been found herein to allow accurate such discrimination.

Thus, in one embodiment the invention provides methods of determining whether a patient is afflicted with hepatocellular carcinoma (HCC), the method comprising determining the level of expression of a marker in a patient sample, wherein the marker is selected from the group consisting of TERT, GPC3, gankyrin, survivin, TOP2A, LYVE1, Ecadherin, IGFBP3, PDGFRA, TGFA, cyclin D1 and HGF; determining the level of expression of the marker in a sample from a control sample; comparing the level of expression of the marker in the patient sample and in the sample from a control sample; and identifying the patient as being afflicted with HCC when a significant difference between the level of expression of the marker in the patient sample and the sample from a control sample is an indication that the patient is afflicted with HCC, thereby determining whether a patient is afflicted with HCC.

In such methods, the level of expression from a control sample may be determined by a method selected from: (a) a level determined from liver cells from the patient which are non-cancerous; (b) a level determined from liver cells from a subject having benign dysplasia or normal tissue; and (c) a predetermined level using an average of the levels of expression from a population of subjects having benign dysplastic nodules or normal liver cells.

In some embodiments, the marker corresponds to a secreted protein. In other embodiments, the marker comprises a transcribed polynucleotide or portion thereof. The sample to be tested, in some embodiments, comprises a sample selected from: a) liver cells obtained from the patient; and b) fluid selected from the group consisting of blood fluid, lymph, urine, prostatic fluid and semen. In specific embodiments, the presence of a marker protein is detected using a reagent which specifically binds with the protein. Exemplary such agents include an antibody, an antibody derivative, and an antibody fragment or even ligands where the marker is a receptor, or portions of a receptor (or the whole receptor) where the marker is a ligand for a receptor.

The level of expression of the marker in the sample is determined by detecting the presence in the sample of a transcribed polynucleotide or portion thereof, corresponding to a nucleic acid marker. Methods for achieving such determination are known to those of skill in the art. In some such methods detecting a transcribed polynucleotide comprises amplifying the transcribed polynucleotide. In other such methods, the level of expression of the marker in the sample is determined by detecting the presence in the sample of a transcribed polynucleotide which anneals with a nucleic acid marker or a portion thereof under stringent hybridization conditions.

In preferred embodiments, the level of expression of the marker in the sample differs from the normal level of expression of the marker in a patient not afflicted with HCC by a factor of at least about 2 or at least about 5.

In the diagnostic methods taught herein, a patient is identified as having HCC when said patient comprises an up-regulation of at least two genes selected from the group consisting of TERT, Glypican-3 (GPC3), gankyrin (PSMD10), and survivin (BRIC5), and TOP2A. In other embodiments, the patient is identified as having HCC when said patient comprises a down-regulation of at least two genes selected from the group consisting of were up-regulated LYVE1 (XLKD1), E-cadherin (CDH1), IGFBP3, PDGFRA, TGFA, cyclin D1 (CCND1) and HGF. The methods may comprise use of a combination of the up-regulated genes and the down-regulated genes.

In the methods of the invention, the expression of at least two markers is determined. For example, the at least two markers are GPC3, and LYVE1. In other embodiments, the expression of at least three markers is determined. In certain embodiments, the at least three markers are GPC3, survivin and LYVE1. In still further embodiments, the expression of at least five markers is determined. An exemplary set of the at least five markers from the set of twelve genes is GPC3, LYVE 1, survivin, TERT and E-cadherin.

In particular embodiments, the expression of the markers is determined by using real time RT-PCR.

In some methods of the invention, the patient sample comprises a small liver nodule obtained from said patient. The small liver nodule is a nodule that is less that 3 cm in size.

The invention also is directed to a method of determining whether small liver nodule is a dysplastic nodule or an early HCC comprising determining the expression of at least three markers selected from the group consisting of TERT, GPC3, gankyrin, survivin, TOP2A, LYVE1, Ecadherin, IGFBP3, PDGFRA, TGFA, cyclin D1 and HGF in said nodule and identifying the nodule as an HCC nodule if the expression of at least two genes selected from the group consisting of up-regulated LYVE1 (XLKD1), E-cadherin (CDH1), IGFBP3, PDGFRA, TGFA, cyclin D1 (CCND1) and HGF is down-regulated as compared to control cells and/or the expression of at least two genes selected from the group consisting of TERT, Glypican-3 (GPC3), gankyrin (PSMD10), and survivin (BRIC5), and TOP2A is up-regulated as compared to control cells; wherein said control cells are selected from the group consisting of (i) liver cells from the patient which are non-cancerous; (ii) liver cells from a subject having benign dysplasia or normal tissue; and (iii) a predetermined level that is obtained an average of the levels of expression from a population of subjects having benign dysplastic nodules or normal liver cells.

Once diagnosis is achieved through the methods discussed herein, the methods may further comprise the step of treating said for HCC if the patient expression profile of the nodules shows that said patient has HCC. Such treating may comprise resection of the nodules, and/or radiation and/or chemotherapy for HCC. Typically, the HCC nodules being diagnosed in the methods of the invention are less than 3 cm in size, although the methods of the invention also are equally applicable to larger tumors to facilitate detection of HCC.

Also contemplated is a method for monitoring the progression of HCC in a patient, the method comprising: a) determining the level of expression of a marker in a patient sample from a first point in time, wherein the marker is selected from the group consisting of TERT, GPC3, gankyrin, survivin, TOP2A, LYVE1, Ecadherin, IGFBP3, PDGFRA, TGFA, cyclin D1 and HGF; b) determining the level of expression of the marker in a sample from the patient at a subsequent point in time; and c) comparing the level of expression detected in steps a) and b), thereby monitoring the progression of HCC in the patient, wherein a change in expression of the marker is indicative of either progression or regression of HCC.

A further aspect of the invention provides for a method of identifying a candidate test compound for inhibiting HCC in a patient, the method comprising: a) determining the expression of a marker in a first sample obtained from the patient and exposed to a test compound, wherein the marker is selected from the group c consisting of TERT, GPC3, gankyrin, survivin, TOP2A, LYVE1, Ecadherin, IGFBP3, PDGFRA, TGFA, cyclin D1 and HGF, b) determining the expression of the marker in a second sample obtained from the patient, wherein the sample is not exposed to the test compound, c) comparing the expression of the marker in the sample exposed to the test compound and the sample not exposed to the test compound; and d) determining a test compound is a candidate compound for inhibiting HCC in a patient when:

(i) the compound up-regulates the expression of two or more genes selected from the group consisting of LYVE1 (XLKD1), E-cadherin (CDH1), IGFBP3, PDGFRA, TGFA, cyclin D1 (CCND1) and HGF and/or (ii) the compound down-regulates the expression of two or more genes selected from the group consisting of TERT, Glypican-3 (GPC3), gankyrin (PSMD10), and survivin (BRIC5), and TOP2A in the sample exposed to the test compound, relative to the second sample, is an indication that the test compound is efficacious for inhibiting HCC in the patient.

In these screening methods, the first and second samples may be portions of a single sample obtained from the patient, or the first and second samples are portions of pooled samples obtained from the patient.

Also provided in the invention are kits for determining whether a patient is afflicted with HCC, the kit comprising reagents for determining expression of at least three markers selected from the group consisting TERT, GPC3, gankyrin, survivin, TOP2A, LYVE1, Ecadherin, IGFBP3, PDGFRA, TGFA, cyclin D1 and HGF; wherein the kit comprises reagents that are selected from: a) at least one nucleic acid probe wherein the probe or probes specifically bind with transcribed polynucleotides corresponding to at least one marker selected from the group consisting of TERT, GPC3, gankyrin, survivin, TOP2A, LYVE1, Ecadherin, IGFBP3, PDGFRA, TGFA, cyclin D1 and HGF; and b) at least one antibody, wherein the antibody or antibodies specifically bind with proteins corresponding to at least one marker selected from the group consisting of TERT, GPC3, gankyrin, survivin, TOP2A, LYVE1, Ecadherin, IGFBP3, PDGFRA, TGFA, cyclin D1 and HGF.

Other kits may be provided for determining whether small liver nodule is a dysplastic nodule or an early HCC comprising reagents for determining expression of GPC3, survivin and LYVE1; wherein the kit comprises reagents that are selected from: a) at least one nucleic acid probe wherein the probe or probes specifically bind with transcribed polynucleotides corresponding to each of the markers GPC3, survivin, and LYVE1; and b) at least one antibody for each of the markers GPC3, survivin, and LYVE1.

In these kits, the at least one nucleic acid probe may be arranged on a microarray.

Also contemplated is a microarray chip that comprises at least one nucleic acid probe that is unique to each of the genes selected from the group consisting of TERT, GPC3, gankyrin, survivin, TOP2A, LYVE1, Ecadherin, IGFBP3, PDGFRA, TGFA, cyclin D1 and HGF.

Another aspect of the invention is directed to a set of genes comprising at least three and more preferably, at least five members of the group consisting of TERT, GPC3, gankyrin, survivin, TOP2A, LYVE1, Ecadherin, IGFBP3, PDGFRA, TGFA, cyclin D1 and HGF, and fragments thereof. In this set of genes, preferably, the set of genes comprises at least GPC3. More preferably, the set of genes comprise at least TERT, GPC3 and survivin. In additional embodiments, the set of genes comprise at least TERT, GPC3, LYVE-1 and survivin. In still other embodiments, the set of genes comprise at least TERT, GPC3, LYVE-1, surviving and E-cadherin. The set of genes is provided in individual containers. One or more of the genes in said set of genes may comprise a detectable label. The genes also may be disposed at a solid surface. In specific embodiments, the set of genes comprises TERT, GPC3, gankyrin, survivin, TOP2A, LYVE1, Ecadherin, IGFBP3, PDGFRA, TGFA, cyclin D1 and HGF, and fragments thereof. In other embodiments, the set of genes consists essentially of TERT, GPC3, gankyrin, survivin, TOP2A, LYVE1, Ecadherin, IGFBP3, PDGFRA, TGFA, cyclin D1 and HGF, and fragments thereof.

Additional aspects of the invention provide kits for determining whether a patient is afflicted with HCC, the kit comprising reagents for determining expression of at least three markers selected from the group consisting TERT, GPC3, gankyrin, survivin, TOP2A, LYVE1, Ecadherin, IGFBP3, PDGFRA, TGFA, cyclin D1 and HGF; wherein the kit comprises reagents that are selected from: a) at least one nucleic acid probe wherein the probe or probes specifically bind with transcribed polynucleotides corresponding to at least one marker selected from the group consisting of TERT, GPC3, gankyrin, survivin, TOP2A, LYVE1, Ecadherin, IGFBP3, PDGFRA, TGFA, cyclin D1 and HGF; and b) reagents for performing RT-PCR.

Another kit contemplated for determining whether small liver nodule is a dysplastic nodule or an early HCC comprises reagents for determining expression of GPC3, survivin and LYVE1; wherein the kit comprises reagents that are selected from: a) at least one nucleic acid probe wherein the probe or probes specifically bind with transcribed polynucleotides corresponding to each of the markers GPC3, survivin, and LYVE1; and b) reagents for performing RT-PCR.

These kits typically will comprise a plurality of probes for one or more of the genes selected from the group consisting of TERT, GPC3, gankyrin, survivin, TOP2A, LYVE1, Ecadherin, IGFBP3, PDGFRA, TGFA, cyclin D1 and HGF. In specific embodiments, the kits comprise probes for at least TERT, GPC3, LYVE-1 and survivin. In other embodiments, the kits comprise probes for at least TERT, GPC3, LYVE-1, survivin and E-cadherin. Some or all of the probes in these kits may be detectably labeled. The probes may be labeled with the same label or with different labels. Certain RT-PCR kits of the invention comprise probes for at least five genes selected from the group consisting of TERT, GPC3, gankyrin, survivin, TOP2A, LYVE1, Ecadherin, IGFBP3, PDGFRA, TGFA, cyclin D1 and HGF. Other exemplary kits comprise at least one probe for each of TERT, GPC3, gankyrin, survivin, TOP2A, LYVE1, Ecadherin, IGFBP3, PDGFRA, TGFA, cyclin D1 and HGF, and fragments thereof.

Other features and advantages of the present invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIGS. 4A-E. Gene expression profiles of the five genes included in the best gene signatures in all the stages of the hepatocarcinogenic process. Results are expressed as foldchange. Boxes reflect median gene expression (25-75 percentile). Legend: Controls (C, n=10), Cirrhosis (Ci,n=10), Dysplastic nodules (D, n=17), early HCC ([E, including very early and early HCC, n=20), Advanced HCC [A, including advanced and very advanced HCC, n=20].

FIGS. 5A-E: Immunostaining for GPC3, counterstained with hematoxylin: A. GPC3 in 0.8 cm HCC and negative staining in the cirrhotic nodule (×100); B. Higher magnification showing diffuse cytoplasmic staining for GPC3 in tumor cells (×400). C. Low grade dysplastic nodule, negative for GPC3 (×200). D. Advanced HCC stained strongly for GPC3 (×100); E. Higher magnification showing the cytoplasmic and canalicular localization of GPC3 in tumor cells (×200).

DETAILED DESCRIPTION OF EXEMPLARY EMBODIMENTS OF THE PRESENT INVENTION

Figure 1:
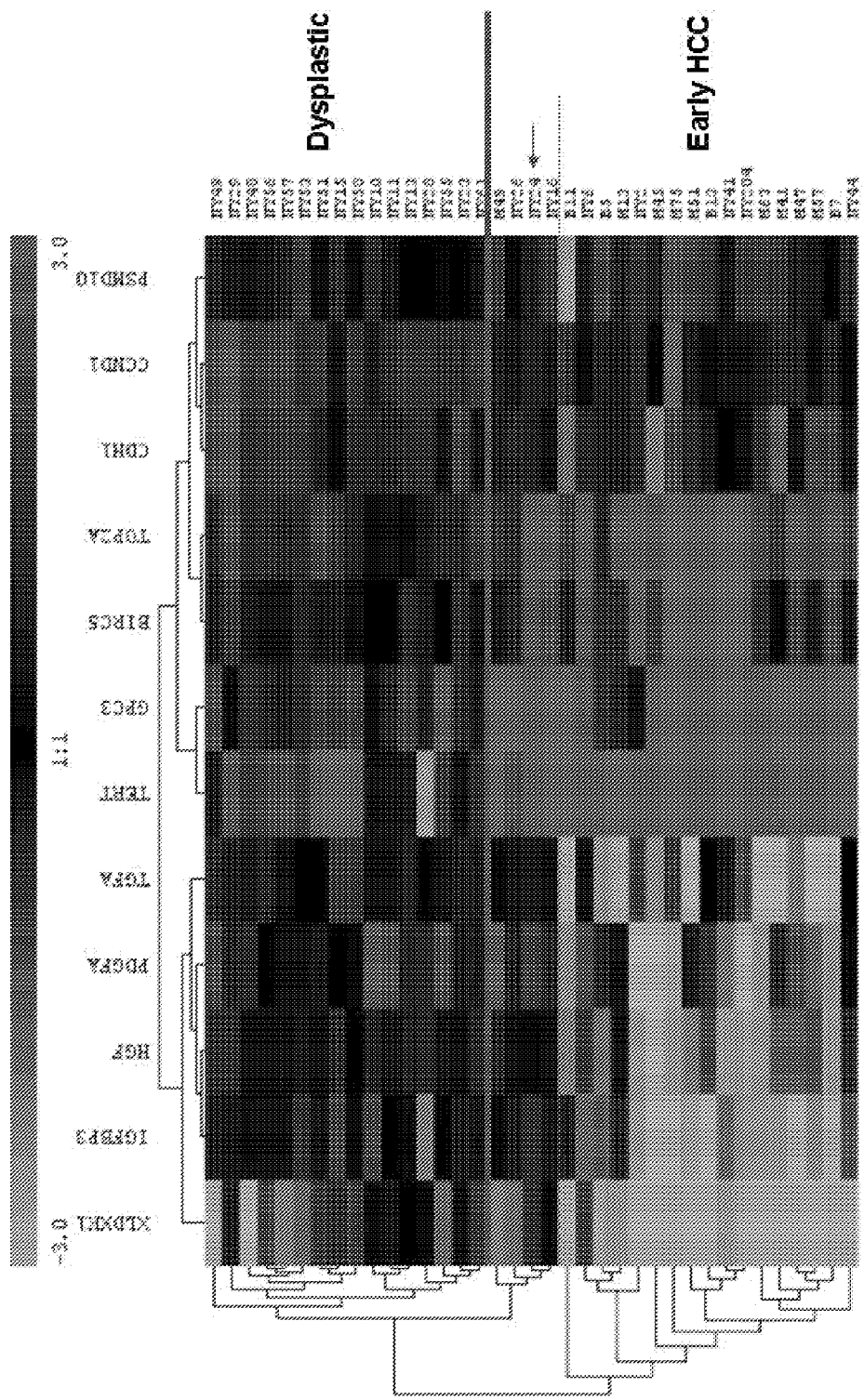
FIG. 1. A dendrogram heat map graph showing a hierarchical clustering of 12 genes significantly dys-regulated in dysplastic nodules (n=17) and early HCC (n=20) according to the gene transcriptional profiles obtained by real time RT-PCR. The genes are in the rows and the samples are in the columns. Red and green represent gene up-regulation and down-regulation, respectively. The line divides the samples as dysplastic nodules or early HCC according to the gene expression analyzed by using average linkage and Pearson correlation distance. Only one sample was misclassified (arrow, NY24) as early HCC.

As discussed above, detection of small liver nodules, e.g., nodules that are about 2 cm or smaller, has proven difficult. The preexisting radiological or pathological examination are insufficient to yield a proper characterization of these nodules. In the present invention, there is an identification of molecular markers that are able to discriminate dysplastic nodules from early hepatocellular carcinoma (HCC).

The transcriptional profiles of candidate genes were obtained from dysplastic nodules that had a diameter of about 10 mm in diameter and early HCC nodules having diameter of 18 mm from HCV-cirrhotic patients undergoing resection or transplantation. In addition profiles also were obtained from non-tumoral cirrhotic tissues normal liver tissues. As described in greater detail below, twelve genes were significantly, differentially expressed in early HCCs as compared to dysplastic nodules (>2-fold change), with an area under the ROC curve>0.8: this included TERT, GPC3, gankyrin, survivin, TOP2A, LYVE1, Ecadherin, IGFBP3, PDGFRA, TGFA, cyclin D1 and HGF. Logistic regression analysis identified a 3-gene set including GPC3 (18-fold increase in HCC, p=0.01), LYVE1 (12-fold decrease in HCC, p=0.0001), and survivin (2.2-fold increase in HCC, p=0.02) which had a discriminative accuracy of 94%. Combination of upregulated genes in cancer [GPC3-TERT; GPC3-survivin] was also informative (accuracy 92%). GPC3 immunostaining was positive in all HCCs and negative in dysplastic nodules (20/20 vs 0/7, p<0.001), but weak focal staining was detected in 7/27 non-tumoral cirrhotic tissues. Nuclear staining for survivin was positive in 12/13 advanced HCC cases, but in 1/7 early tumors. Given the findings of the present inventors, molecular data based on gene transcriptional profiles of a 3-gene set allow reliable discrimination between dysplastic nodules and early HCC. More specifically, it has been shown herein that determining the expression pattern of GPC3, TERT and survivin is a sufficient indicator to discriminate between HCC and dysplastic small liver nodules. These data were confirmed using immunostaining of GPC3 and nuclear staining for survivin. Thus, from the present invention it is now possible to reliably obtain methods of diagnosing HCC even for small liver nodules. Methods of diagnosis and surveillance will lead to further refined therapies for HCC. Such methods are described in further detail below.

The invention relates to markers that can be used for determining whether a small liver nodule is an HCC nodule or whether it is likely to develop into HCC. The use of nucleic acid probes and proteins encoded by the genes selected from the group consisting of TERT, GPC3, gankyrin, survivin, TOP2A, LYVE1, Ecadherin, IGFBP3, PDGFRA, TGFA, cyclin D1 and HGF is contemplated for diagnostic purposes in the present invention. Simply determining the expression levels of GPC3, TERT, LYVE 1, and survivin alone is sufficient to show whether a given nodule in a liver biopsy is an HCC nodule or whether it is merely a dysplastic small liver nodule.

Further antibodies, antibody derivatives and antibody fragments which bind specifically with such marker proteins and/or fragments of the marker proteins will be useful in achieving the diagnoses of the invention. Thus, the invention will provide for various methods, reagents and kits for diagnosing, staging, prognosing, monitoring and treating HCC. Antibodies against GPC3, TERT, LYVE 1, and survivin will be particularly useful.

In one embodiment, for example, the diagnostic methods of assessing whether a patient has HCC or has higher than normal risk for developing HCC will involve comparing the level of expression of TERT, GPC3, gankyrin, survivin, TOP2A, LYVE1, Ecadherin, IGFBP3, PDGFRA, TGFA, cyclin D1 and HGF in a patient sample and the normal level of expression of the marker or markers in a control, e.g., a sample from a patient without HCC.

A significantly altered level of expression of the marker or markers in the patient sample in accordance with the expression patterns described herein can be indicative of a patient having or at risk for developing HCC. The methods of the present invention can be of use in identifying patients having an enhanced risk of developing HCC (e.g., patients having a familial history of HCC, or patients that have had HCV infection,). The methods are also useful diagnostics for assessing whether a patient has a HCC or is likely to develop HCC.

The methods of the present invention may be useful in predicting the specific stage of HCC, as well as in assessing whether the cancer has metastasized (e.g., metastasis to the lymph nodes). Still further, the methods of the present invention also may be useful in predicting the clinical outcome for a patient with HCC, or for a patient who has undergone therapy to eradicate HCC. Additionally, the methods of the present invention also may be useful in assessing the efficacy of treatment of a HCC patient (e.g., the efficacy of chemotherapy).

According to the invention, the markers are selected such that the positive predictive value of the methods of the invention is at least about 10%, preferably about 25%, more preferably about 50% and most preferably about 90%. Also preferred are embodiments of the method wherein the marker is over-expressed by at least five-fold in at least about 15% of liver cancer patients as compared to normal non-liver cancer patients.

The invention further provides a diagnostic method of assessing whether a patient is afflicted with a HCC which has metastasized or is likely to metastasize, the method comprising comparing the level of expression of one or more of the genes selected from TERT, GPC3, gankyrin, survivin, TOP2A, LYVE1, Ecadherin, IGFBP3, PDGFRA, TGFA, cyclin D1 and HGF in a sample from the patient, and the level of expression of the marker or markers in a sample from a control subject having a non-metastasized liver tumor. A significantly higher level of expression in the patient sample of TERT, Glypican-3 (GPC3), gankyrin (PSMD10), and survivin (BRIC5), and TOP2A (i.e., that set of genes shown in the Example to be up-regulated in HCC) and/or a significantly lower level of expression in the patient sample of LYVE1 (XLKD1), E-cadherin (CDH1), IGFBP3, PDGFRA, TGFA, cyclin D1 (CCND1) and HGF (i.e., that set of genes shown in the Example to be down-regulated in HCC) as compared to the level in the sample from the control subject is an indication that the HCC has metastasized or is likely to metastasize.

The invention also provides a method for predicting the clinical outcome of a HCC patient, comprising comparing the level of expression of two, three, four, five, six, seven, eight, nine, ten, eleven or all twelve genes selected from the group of TERT, GPC3, gankyrin, survivin, TOP2A, LYVE1, Ecadherin, IGFBP3, PDGFRA, TGFA, cyclin D1 and HGF in a sample from the patient and the level of expression of that gene in a sample for a control subject having a good clinical outcome (e.g., a patient that has had HCC but has been cancer-free for a period of at least five years). A significant alteration in the expression of the genes in the direction described herein for the individual genes in the patient sample as compared to the expression level in the sample from the control subject is an indication that the patient has a poor outcome (e.g., less than three years of disease free survival).

The efficacy of a therapy for inhibiting HCC in a patient also can be monitored with the methods of the invention by simply comparing the expression levels and patterns of at least two (at least three, at least four, at least five, at least six, at least seven, at least eight, at least nine, at least ten, at least eleven, or all twelve) genes selected from the group consisting of TERT, GPC3, gankyrin, survivin, TOP2A, LYVE1, Ecadherin, IGFBP3, PDGFRA, TGFA, cyclin D1 and HGF. Such methods comprise comparing expression of the given marker or markers in a first sample that is obtained isolated from the patient prior to the initiation of the therapy to the patient and, with the expression of the marker or markers in a second sample obtained from the patient after the patient has undergone appropriate therapy for a desired period of time. A significant alteration in the expression of the marker or markers in the second sample relative to that in the first sample is an indication that the therapy is efficacious for inhibiting HCC in the patient. For example, where the therapy increases the expression of the genes that are identified herein as being down-regulated in HCC nodules, and/or decreases the expression of the genes that are indicated herein as being up-regulated in HCC, such therapy will be identified as being effective at inhibiting HCC in the patient.

AS used herein, the "therapy" methods may be any therapy typically used for treating cancer, including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In some examples, the invention involves therapy using a chemical or biologic agent.

In other embodiments, the invention involves monitoring the progression of HCC cancer in a patient, the method comprising: detecting in a sample from the patient at a first time point, the expression of at least two markers of the invention and then repeating the detection of expression step at a subsequent time point(s) in time; and comparing the level of expression detected in the first and second detection steps, thereby monitoring the progression of HCC in the patient. A significantly higher level of expression of TERT, Glypican-3 (GPC3), gankyrin (PSMD10), and survivin (BRIC5), and TOP2A and/or a significantly lower expression of LYVE1 (XLKD1), E-cadherin (CDH1), IGFBP3, PDGFRA, TGFA, cyclin D1 (CCND1) and HGF in the sample at the subsequent time point from that of the sample at the first time point is an indication that the HCC has progressed in the patient, whereas a significantly lower level of expression of TERT, Glypican-3 (GPC3), gankyrin (PSMD10), and survivin (BRIC5), and TOP2A and/or higher level of expression of LYVE1 (XLKD1), E-cadherin (CDH1), IGFBP3, PDGFRA, TGFA, cyclin D1 (CCND1) and HGF may be indicative that the HCC has regressed.

Also provided herein are methods of screening for and selecting candidate agents that will inhibit HCC in a patient. This method comprises the steps of: obtaining a sample comprising HCC cells from the patient; separately maintaining at least one sample comprising cancer cells from the patient in the presence of at least one test composition; comparing expression of at least three markers of the invention in each of the aliquots; and selecting a test composition as a candidate composition for inhibition of liver cancer where the composition significantly alters the level of expression of at least one marker of the invention in the aliquot containing that test composition, relative to the levels of expression of the marker in the presence of the other test compositions.

The methods of the invention can be used as molecular targets for HCC in a patient. In such methods, a sample of HCC are obtained from the subject, some of the sample is treated with a test agent and the reset of the sample is maintained as a control. The level of expression of the markers identified herein is compared between the two separate samples to identify whether the test composition is an inhibitor of HCC, where if the agent increases LYVE1 (XLKD1), E-cadherin (CDH1), IGFBP3, PDGFRA, TGFA, cyclin D1 (CCND1) and HGF and/or decreases TERT, Glypican-3

(GPC3), gankyrin (PSMD10), and survivin (BRIC5), and TOP2A, the agent is shown to be an inhibitor of HCC. The method would then further comprise the step of administering to the patient at least one of the compositions which are identified as an inhibitor of HCC.

According to the invention, any of the aforementioned methods may be performed using or detecting a plurality (e.g. 2, 3, 4, 5, 6, 7, 8, 9, 10, 11, or 12) of the HCC markers identified herein (i.e., TERT, GPC3, gankyrin, survivin, TOP2A, LYVE1, Ecadherin, IGFBP3, PDGFRA, TGFA, cyclin D1 and HGF), including a combination of the provided markers of the invention with additional HCC markers known in the art. In such methods, the level of expression in the sample of each of a plurality of markers, at least one of which is a marker of the invention, is compared with the normal level of expression of each of the plurality of markers in samples of the same type obtained from control humans not afflicted with HCC. A significantly altered (i.e., increased or decreased as specified in the described methods using a single marker) level of expression in the sample of one or more markers of the invention, or some combination thereof, relative to that marker's corresponding normal or control level, is an indication that the patient is afflicted with HCC.

Also contemplated by the present invention are various diagnostic and test kits. Such kits may be used for determining whether a patient has HCC or is in the early stages of developing HCC or is at risk of developing HCC. The kit comprises a reagent for assessing expression of the marker genes of interest. Yet another embodiment provides a kit which may be used for assessing whether a patient is afflicted with an aggressive liver tumor. The kit comprises a reagent for assessing expression of at least one marker of the invention. In another embodiment, the invention provides a kit for assessing the suitability of a chemical or biologic agent for inhibiting liver cancer in a patient. Such a kit comprises reagents for assessing expression of at least one marker of the invention, and may also comprise one or more of such agents. In a further embodiment, the invention provides kits for assessing the presence of liver cancer cells or treating liver cancers. Such kits may comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

The invention provides a kit for assessing the presence of HCC cells, wherein the kit comprises at least one nucleic acid probe that binds specifically with at least one marker nucleic acid or a fragment of the nucleic acid. The kit may further comprise a plurality of probes, wherein each of the probes binds specifically with a marker nucleic acid, or a fragment of the nucleic acid.

In a further aspect, the invention relates to methods for treating a patient afflicted with liver cancer or at risk of developing liver cancer. Such methods may comprise reducing the expression and/or interfering with the biological function of at least one marker of the invention selected from the group consisting of TERT, Glypican-3 (GPC3), gankyrin (PSMD10), and survivin (BRIC5), and TOP2A (i.e., the group of genes shown herein in the Example to be up-regulated in HCC) or increasing and/or promoting the biological function of at least one marker selected from the group consisting of LYVE1 (XLKD1), E-cadherin (CDH1), IGFBP3, PDGFRA, TGFA, cyclin D1 (CCND1) and HGF (i.e., the genes shown herein in the Example to be down-regulated in HCC).

It will be appreciated that the methods and kits of the present invention may also include known cancer markers including known liver cancer markers. It will further be appreciated that the methods and kits may be used to identify cancers other than liver cancer.

The invention also extends to microarrays. In one aspect, a microarray is provided for measuring gene expression of genes that are differentially expressed in HCC comprising at least 2 polynucleotides wherein each of the at least 2 polynucleotides has a distinct sequence from two separate genes selected from the group consisting of TERT, GPC3, gankyrin, survivin, TOP2A, LYVE1, Ecadherin, IGFBP3, PDGFRA, TGFA, cyclin D1 and HGF. In some embodiments, the microarray of the invention comprises at least 5, 10, 15, 25, or 50 polynucleotides, wherein, in each such embodiment, each of the expressly enumerated number of polynucleotides has a distinct sequence from two separate genes selected from the group consisting of TERT, GPC3, gankyrin, survivin, TOP2A, LYVE1, Ecadherin, IGFBP3, PDGFRA, TGFA, cyclin D1 and HGF. In some embodiments, the microarray is prepared using a plurality probes that hybridize to different sections of each of the genes selected from the group consisting of TERT, GPC3, gankyrin, survivin, TOP2A, LYVE1, Ecadherin, IGFBP3, PDGFRA, TGFA, cyclin D1 and HGF. For example, the microarray may comprise 5, 10, 15, 20, 25, 30, 40, 45, 50 or more probes that hybridize to different parts of the TERT gene, and may comprise an equal or different number of distinct probes that hybridize to different parts of the GPC3 gene, and may comprise an equal or different number of distinct probes that hybridize to different parts of the survivin gene etc. The microarray may comprise probes directed to each of the genes selected from the group consisting of TERT, GPC3, gankyrin, survivin, TOP2A, LYVE1, Ecadherin, IGFBP3, PDGFRA, TGFA, cyclin D1 and HGF or only some of the genes from this group. In specific embodiments, the primers or probes may be between 5 to 25 bases in length. Of course longer probes also may be used.

The invention is founded in the discovery that there is a set of markers that can reliably distinguish between HCC and dysplastic small liver nodules. It has been discovered that the higher than normal level of expression of any of the markers selected from the group consisting of TERT, Glypican-3 (GPC3), gankyrin (PSMD10), and survivin (BRIC5), and TOP2A; lower than normal level of expression of any of the markers selected from the group consisting of LYVE1 (XLKD1), E-cadherin (CDH1), IGFBP3, PDGFRA, TGFA, cyclin D1 (CCND1) and HGF; or combination of these markers correlates with the presence of HCC in a patient.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of nucleotide SEQ ID NO or the complement of such a sequence. The marker nucleic acids also include RNA comprising the entire or a partial sequence of any nucleotide SEQ ID NO or the complement of such a sequence, wherein all thymidine residues are replaced with uridine residues. A "marker protein" is a protein encoded by or corresponding to a marker of the invention. A marker protein comprises the entire or a partial sequence of any of the amino acid SEQ ID NO. The terms "protein" and "polypeptide' are used interchangeably.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

Probes from any one or more of the genes shown herein to be markers of HCC may be used as primers in an RT-PCR assay method to detect a specific RNA molecule through its reverse transcription into DNA, followed by amplification of its copy DNA using the polymerase chain reaction. As used herein, the term "reverse transcription followed by polymerase chain reaction", or "RT-PCR", refers to a technique for synthesizing and amplifying a DNA molecule with a sequence that is a copy of an RNA sequence. RT-PCR is useful for detecting RNA species such as in quantitative analysis of gene expression, as well as for producing DNA copies of RNA for use in cloning, cDNA library construction, probe synthesis, and signal amplification in in situ hybridizations. The technique consists of two parts: synthesis of cDNA from RNA by reverse transcription (RT), and amplification of a specific cDNA by polymerase chain reaction (PCR). Reverse transcriptase is an RNA dependent DNA polymerase that catalyses the polymerization of nucleotides using template RNA or the RNA molecule in an RNA:DNA hybrid.

As used herein, the term "primer" refers to an oligonucleotide, synthetic or naturally occurring, which is capable of acting as a point of initiation of nucleic acid synthesis or replication along a template strand when placed under conditions in which the synthesis of a complementary strand is catalyzed by a polymerase. Within the context of reverse transcription, primers are composed of nucleic acids and prime on RNA templates. Within the context of PCR, primers are composed of nucleic acids and prime on DNA templates.

The methods of the present invention thus use an "RT-PCR reaction composition," i.e., a composition having all the elements required to perform reverse transcription—polymerase chain reaction including but not limited to: primers having specificity for the sequence of the diagnostic target RNA; a heat activated thermostable polymerase; a reverse transcriptase; dNTPs and appropriate buffers in order to assess the presence of one or more of the markers of the present invention.

An "amplification product" refers to nucleic acid fragments that are produced during a primer directed amplification reaction. Typical methods of primer directed amplification include polymerase chain reaction (PCR), RT-PCR, ligase chain reaction (LCR) or strand displacement amplification (SDA).

In the present methods, the presence of diagnostic target RNAs of HCC can be tested by reverse transcription alone or by reverse transcription and polymerase chain reaction. In preferred embodiments, the RNA is detected using real-time RT PCR. "Real time RT-PCR" refers to a method or device used therein that allows for the simultaneous amplification and quantification of specific RNA transcripts in a sample. When used together, reverse transcription and polymerase chain reaction may be performed sequentially in two steps, or together in one step with all reaction composition reagents being added to the cell sample.

Incubation of the cell sample in the reverse transcription reaction composition allows a DNA copy from the target RNA to be synthesized. The RT composition includes a primer that hybridizes to the target RNA to prime the synthesis of the copy DNA. In addition, the RT composition includes dNTPs, $MgCl_2$, a reverse transcriptase and a reverse transcriptase buffer. More than one primer may be included if it is desired to make DNA copies from more than one target RNA. Additionally the RT composition may optionally contain an RNase inhibitor as described herein.

The product of the reverse transcription reaction may be detected directly, or a sample of this reaction may be transferred to another assay tube containing PCR composition including a pair of primers that initiate synthesis of the desired segment of DNA from the reverse transcribed template. In addition, the PCR composition contains dNTPs, a thermostable DNA polymerase such as Taq polymerase, and polymerase buffer. More than one pair of primers may be included if synthesis of multiple segments of DNA is desired. Also a single new primer may be added that will amplify a DNA segment with the original RT-PCR primer as the second primer of the pair.

Additional reverse transcriptases that may be used include, but are not limited to, HIV Reverse Transcriptase (Ambion), Transcriptor Reverse Transcriptase (Roche), Thermoscript Reverse Transcriptase (Invitrogen). Additional DNA polymerases that may be used include, but are not limited to, Pfu, Vent, and Sequitherm DNA Polymerase (EPICENTRE).

Regardless of whether the RT-PCR is carried out as two steps or one step, the RT step is run first and typically consists of a single temperature incubation at a temperature of between about 37° C. and about 70° C. Different temperatures are appropriate for different RT enzymes and different primers, as is known to one skilled in the art. The subsequent PCR reaction typically consists of an initial incubation at about 94° C. to about 96° C. for about 6 to about 15 minutes. This step is used to denature the cDNA and also to activate heat activated Taq polymerase enzymes. This is then followed by multiple cycles of amplification of the cDNA target.

Three operations are performed during each cycle: target denaturation, primer annealing and primer extension. Target denaturation typically occurs at greater than about 90° C. Primer annealing temperature is dictated by the melting temperature of the specific primers used in the reaction and primer extension is performed at temperatures ranging from about 60° C. to about 72° C. depending on the thermostable polymerase being used. When primer annealing and extension are performed at the same temperature, this is a two temperature PCR compared with a three temperature PCR in which each of the three steps occur at a different temperature. After the amplification phase is complete, a final extension time is typically added to ensure the synthesis of all amplification products.

In specific embodiments, the present invention provides kits, which include instructions for performing the present methods utilizing an RT-PCR composition or an RT-composition to obtain either RT-PCR or RT reaction product, respectively, and amplifying the product. Alternatively, the instructions relate to direct detection of an RT-product without further amplification of it. Additionally, the kit may contain either an RT-PCR composition or RT composition, which results in an RT-PCR or RT reaction mixture, respectively, upon contact with the sample. The kits will typically contain one or more primers for the detection of one or more genes selected from the group consisting of TERT, GPC3, gankyrin, survivin, TOP2A, LYVE1, Ecadherin, IGFBP3, PDGFRA, TGFA, cyclin D1 and HGF.

The instant invention is not limited as to the method of detection and may be used by any such method that detects the product of the RT or RT-PCR reaction. Methods for directly detecting the cDNA product of an RT reaction are well known to one skilled in the art and make use of labels incorporated into or attached to the cDNA product. Signal generating labels that may be used are well known in the art and include, for example, fluorescent moieties, chemiluminescent moieties, particles, enzymes, radioactive tags, or light emitting moieties or molecules.

Fluorescent labels are particularly useful, especially fluorescent dyes capable of attaching to nucleic acids and emitting a fluorescent signal. A variety of dyes are known in the art such as fluorescein, Texas Red, and rhodamine. Particularly useful are the mono reactive dyes Cy3 and Cy5, both available commercially (from, for example, Amersham Pharmacia Biotech, Arlington Heights, Ill.). A more sensitive way to specifically detect the labeled DNA is to hybridize the products against target DNA sequence molecules that are immobilized in a matrix, such as a nylon membrane or a glass slide. The signals after hybridization can then be scanned with a laser scanner with appropriate filtering to detect the specific dye used. This is well known in the art, especially in DNA microarray technology.

A label may be incorporated into the cDNA during its synthesis in the RT reaction, or it may be attached to the cDNA product after its synthesis. For example, the RT reaction can be carried out with labeled primers. One type of labeled primer has attached particles having a large number of signal generating molecules. Reverse transcription using a labeled nucleotide, such as dye-labeled UTP and/or CTP, incorporates a label into the transcribed nucleic acids. Alternatively, a post-synthesis coupling reaction can be used to detect the cDNA products.

Attaching labels to nucleic acids is well known to those of skill in the art and may be done by, for example, nick translation or end-labeling with, e.g. a labeled RNA or by treatment of the nucleic acid with kinase and subsequent attachment of a nucleic acid linker joining the sample nucleic acid to the label, e.g., a fluorophore. In another labeling method, the DNA products from the RT reaction are amplified by coupling to an in vitro transcription reaction. For example, the T7 promoter region is incorporated into the primer used for the RT reaction. A T7 in vitro transcription kit can then be used to generate a large amount of RNA to increase the detection sensitivity. The T7 in vitro transcriptional kit can be purchased from Ambion (2130 Woodward, Austin, Tex.) or other commercial sources.

Methods for RT-PCR product detection include gel electrophoresis separation and ethidium bromide staining, or detection of an incorporated fluorescent label or radiolabel in the product. Methods that do not require a separation step prior to detection of the amplified product may also be used. These methods are commonly referred to as Real-Time PCR or homogeneous detection. Most real time methods detect amplified product formation by monitoring changes in fluorescence during thermocycling. These methods include but are not limited to: TaqMan® dual labeled probes (Applied Biosystems, Foster City, Calif. 94404), Molecular Beacons (Tyagi S and Kramer FR (1996) Nat Biotechnol 14:303-308), and SYBR® Green dye (Molecular Probes, Inc Eugene, Oreg. 97402-0469). Some of these same homogeneous methods can be used for end point detection of amplified products as well. An example of this type of method is SYBR® Green dye dissociation curve analysis. In dissociation curve analysis a final slow ramp in temperature, generally about 60° C. to 90° C., combined with fluorescence monitoring can detect the melting point and thereby the presence of an amplified product.

In addition, to RT-PCR, detection of differentially expressed genes also may use other methods of evaluating differential gene expression. Examples include indexing differential display reverse transcription polymorase chain reaction (DDRT-PCR; Mahadeva et al, 1998, J. Mol. Biol. 284: 1391-1318; WO 94/01582; subtractive mRNA hybridization (See Advanced Mol. Biol.; R. M. Twyman (1999) Bios Scientific Publishers, Oxford, p. 334, the use of nucleic acid arrays or microarrays (see Nature Genetics, 1999, vol. 21, Suppl. 1061) and the serial analysis of gene expression (SAGE Valculesev et al, Science (1995) 270:484-487) and real time PCR (RT-PCR). Combinations of these methods can be used. Differential levels of a transcribed gene in an oocyte cell can be detected by use of Northern blotting, and/or RT-PCR.

Thus, in the methods shown herein, HCC cells will be obtained from a patient to be tested and subjected to gene expression analysis, i.e., by isolation of total RNA therefrom, amplification of said total RNA, quantification of the relative gene expression levels of said RNAs by microarray analysis and RT-PCR, and the identification of genes TERT, Glypican-3 (GPC3), gankyrin (PSMD10), and survivin (BRIC5), and TOP2A, the increased expression of which correlates to HCC and genes LYVE1 (XLKD1), E-cadherin (CDH1), IGFBP3, PDGFRA, TGFA, cyclin D1 (CCND1) and HGF, the decreased expression of which also correlated with HCC.

In those embodiments where protein expression is to be detected, protein expression in a test HCC specimen or a normal control liver tissue can be determined by methods well known in the art for measuring protein expression. Commonly, detection of specific proteins involves the use of antibodies. Immunohistochemistry is broadly applicable, but western hybridization, radioimmunoassay (RIA), and flow cytometry can also be used; collectively protein determinations. Such methods include, but are not limited to, immunohistochemical staining, ELISA, immunoprecipitation, western blot (immunoblot), radioimmuno assay (RIA), and fluorescence-activated cell sorting (FACS).

A "HCC-associated" body sample that can be tested using the methods of the invention is a sample which, when in the body of a patient, contacts or passes through liver cells or into which cells or proteins shed from liver cells are capable of passing. Such an HCC-sample may be liver tissue obtained from a biopsy, or may be fluid associated with an HCC patient. Exemplary HCC-associated body fluids include blood fluids (e.g. whole blood, blood serum, blood having platelets removed therefrom), lymph, urine, prostatic fluid and semen. HCC-associated body fluids (i.e. usually excluding urine) can have HCC cells therein, particularly when the liver cells are cancerous, and, more particularly, when the liver cancer is metastasizing.

It should be understood that while the HCC may be HCC from a patient that has had an HCV infection, the methods of the invention may be used to detect, diagnose and monitor any HCC regardless of its etiology.

The "sample(s)" or "patient sample(s)" comprise cells or liver-associated body fluid obtained from a patient. The cells may be isolated from, identified, or found in a liver tissue sample collected, for example, by a liver tissue biopsy or histology section, or a bone marrow biopsy. Alternatively, the patient sample is in vivo. Yet another alternative sample (for example in the screening embodiments discussed elsewhere in the specification) includes in vitro cells or cell lines which are liver cancer cells or liver cancer primary cells.

The "normal" level of expression of a marker is the level of expression of the marker in liver cells of a human subject or patient not afflicted with liver cancer.

An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subject not having the marker associated disease, i.e., liver cancer) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subjects not having the marker associated disease, i.e., liver cancer) and preferably, the average expression level of the marker in several control samples.

A "transcribed polynucleotide" or "nucleotide transcript" is a polynucleotide (e.g. an mRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

A cancer is "inhibited" if at least one symptom of the cancer is alleviated, terminated, slowed, or prevented. As used herein, HCC is also "inhibited" if recurrence or metastasis of the cancer is reduced, slowed, delayed, or prevented. A kit is any article of manufacture (e.g. a package or container) comprising at least one reagent, e.g. a probe, for specifically detecting the expression of an HCC marker identified herein. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The invention provides compositions, kits, and methods for assessing the cancerous state of liver cells (e.g. cells obtained from a human, cultured human cells, archived or preserved human cells and in vivo cells) as well as treating patients afflicted with HCC liver cancer.

The compositions, kits, and methods of the invention have the following uses, among others: assessing whether a patient is afflicted with HCC; assessing the metastatic potential of HCC in a human patient; making antibodies, antibody fragments or antibody derivatives that are useful for determining whether a subject has HCC and/or treating such a patient; determining the presence of liver cancer cells; determining the efficacy of one or more test compounds for inhibiting liver cancer in a patient; determining the efficacy of a therapy for inhibiting liver cancer in a patient; monitoring the progression of HCC in a patient; selecting a composition or therapy for inhibiting liver cancer in a patient; treating a patient afflicted with liver cancer; inhibiting liver cancer in a patient; and preventing the onset of liver cancer in a patient at risk for developing such cancer. As noted herein throughout, the methods, kits and compositions of the present invention are particularly useful in providing an early detection of HCC, particularly in nodules that are about 2 cm in diameter. Detection of such small liver nodules is particularly beneficial as it allows an early therapeutic intervention of the disease.

The invention thus includes a method of determining whether a patient is afflicted with liver cancer which includes determining if the patient has pre-metastasized liver cancer. This method comprises comparing the level of expression of a marker of the invention in a patient sample and the normal level of expression of the marker in a control, e.g., a non-HCC cancer sample. A significantly higher level of expression of TERT, Glypican-3 (GPC3), gankyrin (PSMD10), and survivin (BRIC5), and TOP2A in the patient sample and/or a significantly lower level of expression of LYVE1 (XLKD1), E-cadherin (CDH1), IGFBP3, PDGFRA, TGFA, cyclin D1 (CCND1) and HGF as compared to the normal level is an indication that the patient is afflicted with liver cancer.

As described herein, HCC in patients is associated with an altered level of expression of one or more markers selected from the group consisting of TERT, GPC3, gankyrin, survivin, TOP2A, LYVE1, Ecadherin, IGFBP3, PDGFRA, TGFA, cyclin D1 and HGF. While, as discussed above, some of these changes in expression level result from occurrence of the liver cancer, others of these changes induce, maintain, and promote the cancerous state of liver cancer cells. Thus, liver cancer characterized by an increase in the level of expression of one or more markers of the invention can be inhibited by reducing and/or interfering with the expression of the markers and/or function of the proteins encoded by those markers, and cancer characterized by a decrease in the level of expression of one or more markers of the invention can be inhibited by increasing and/or promoting the expression of the markers and/or function of the proteins encoded by those markers. Gene therapy methods to achieve such results may be employed Any marker or combination of markers identified in the present invention, as well as any known markers in combination with the markers identified herein, may be used in the compositions, kits, and methods of the present invention. In general, it is preferable to use markers for which the difference between the level of expression of the marker in liver cancer cells and the level of expression of the same marker in normal liver cells is as great as possible. Although this difference can be as small as the limit of detection of the method for determining expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-fold or greater than the level of expression of the same marker in normal liver tissue.

It is recognized that certain marker proteins may be secreted from liver cells (i.e. one or both of normal and cancerous cells) to the extracellular space surrounding the cells. These markers are preferably used in certain embodiments of the compositions, kits, and methods of the invention, owing to the fact that the such marker proteins can be detected in a HCC-associated body fluid sample, which may be more easily collected from a human patient than a tissue biopsy sample. In addition, preferred in vivo techniques for detecting the presence of a marker protein include introducing into a subject a labeled antibody directed against the protein. For example, the antibody can be labeled with a radioactive marker whose presence and location in a subject can be detected by standard imaging techniques.

It is a simple matter for the skilled artisan to determine whether any particular marker protein is a secreted protein. In order to make this determination, the marker protein is expressed in, for example, a mammalian cell, preferably a human liver cell line, extracellular fluid is collected, and the presence or absence of the protein in the extracellular fluid is assessed (e.g. using a labeled antibody which binds specifically with the protein).

It will be appreciated that patient samples containing liver cells may be used in the methods of the present invention. In these embodiments, the level of expression of the marker can be determined by detecting the amount (e.g. absolute amount or concentration) of the marker in a liver cell sample, e.g., a liver tissue biopsy obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample Likewise, liver tissue biopsies may also be subjected to post-collection preparative and storage techniques, e.g., fixation.

The compositions, kits, and methods of the invention can be used to detect expression of marker proteins having at least one portion which is displayed on the surface of cells which express it. To determine whether a marker protein, or a portion thereof, is presented on a cell surface, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the cell (e.g. using a labeled antibody which binds specifically with a cell-surface domain of the protein).

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a marker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair (e.g. biotin-streptavidin)), or an antibody fragment (e.g. a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e. a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g. single nucleotide polymorphisms, deletions, etc.) of a marker of the invention may be used to detect occurrence of a marker in a patient. RT-PCR is a particularly useful method for the detection of the markers.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a marker nucleic acid. If polynucleotides complementary to or homologous with are differentially detectable on the substrate (e.g. detectable using different chromophores or fluorophores, or fixed to different selected positions), then the levels of expression of a plurality of markers can be assessed simultaneously using a single substrate (e.g. a "gene chip" microarray of polynucleotides fixed at selected positions). When a method of assessing marker expression is used which involves hybridization of one nucleic acid with another, it is preferred that the hybridization be performed under stringent hybridization conditions.

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with liver cancer. When a plurality of markers is used, it is preferred that 2, 3, 4, 5, 8, 10, or all 12, of the individual markers identified herein (either in combination with two or more said 12 markers and/or in combination with other known HCC markers) can be used.

It is recognized that the compositions, kits, and methods of the invention will be of particular utility to patients having an enhanced risk of developing HCC cancer and their medical advisors. Patients recognized as having an enhanced risk of developing HCC cancer include, for example, patients having a familial history of liver cancer, patients identified as having a mutant oncogene (i.e. at least one allele), patients of advancing age (i.e. men older than about 50 or 60 years), particularly cirrhotic patients that have cirrhotic scarring due to alcohol abuse, or cirrhotic patients that have liver cirrhosis due to HCV or HBV infection.

The level of expression of a marker in normal (i.e. non-cancerous) human liver tissue can be assessed in a variety of ways. In one embodiment, this normal level of expression is assessed by assessing the level of expression of the marker in a portion of liver cells which appears to be non-cancerous and by comparing this normal level of expression with the level of expression in a portion of the liver cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of liver cancer in the patient, from archived patient samples, and the like.

The invention includes compositions, kits, and methods for assessing the presence of liver cancer cells in a sample (e.g. an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of liver cancer cells (e.g. in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g. SSC buffer) suitable for annealing complementary nucleic acids or for binding an antibody with a protein with which it specifically binds, one or more sample compartments, an instructional material which describes performance of a method of the invention, a sample of normal liver cells, a sample of liver cancer cells, and the like.

The invention also includes a method of determining the efficacy of a test compound for inhibiting liver cancer cells. As described above, differences in the level of expression of the markers of the invention correlate with the cancerous state of liver cells. Although it is recognized that changes in the levels of expression of certain of the markers of the invention likely result from the cancerous state of liver cells, it is likewise recognized that changes in the levels of expression of the markers of the invention induce, maintain, and promote the cancerous state of those cells. Thus, compounds which inhibit a liver cancer in a patient will cause the level of expression of one or more of the markers of the invention to change to a level nearer the normal level of expression for that marker (i.e. the level of expression for the marker in non-cancerous liver cells).

This method thus comprises comparing expression of a marker in a first liver cell sample and maintained in the presence of the test compound and expression of the marker in a second liver cell sample and maintained in the absence of the test compound. A significantly reduced expression of a marker such as TERT, Glypican-3 (GPC3), gankyrin (PSMD10), and survivin (BRIC5), and TOP2A (i.e., that set of genes shown in the Example to be up-regulated in HCC) or increased expression of a marker such as LYVE1 (XLKD1), E-cadherin (CDH1), IGFBP3, PDGFRA, TGFA, cyclin D1 (CCND1) and HGF (i.e., that set of genes shown in the Example to be down-regulated in HCC) in the presence of the test compound is an indication that the test compound inhibits liver cancer. The liver cell samples may, for example, be aliquots of a single sample of normal liver cells obtained from a patient, pooled samples of normal liver cells obtained from a patient, cells of a normal liver cell line, aliquots of a single sample of liver cancer cells obtained from a patient, pooled samples of liver cancer cells obtained from a patient, cells of a liver cancer cell line, or the like. In one embodiment, the samples are liver cancer cells obtained from a patient and a plurality of compounds known to be effective for inhibiting various liver cancers are tested in order to identify the compound which is likely to best inhibit the liver cancer in the patient.

This method may likewise be used to assess the efficacy of a therapy for inhibiting liver cancer in a patient. In this method, the level of expression of one or more markers of the invention in a pair of samples (one subjected to the therapy, the other not subjected to the therapy) is determined. As with the method of assessing the efficacy of test compounds, if the therapy significantly reduces expression of at least one marker such as TERT, Glypican-3 (GPC3), gankyrin (PSMD10), and survivin (BRIC5), and TOP2A (i.e., the set of genes that is shown in the Example as being up-regulated in HCC) or increases expression of a marker such as LYVE1 (XLKD1), E-cadherin (CDH1), IGFBP3, PDGFRA, TGFA, cyclin D1 (CCND1) and HGF (i.e., the set of genes that is shown in the Example as being down-regulated in HCC) in the presence of the therapy is an indication that the therapy is effective at treating the liver cancer. As above, if samples from a selected patient are used in this method, then alternative therapies can be assessed in vitro in order to select a therapy most likely to be efficacious for inhibiting liver cancer in the patient.

Polynucleotide-based or oligonucleotide-based arrays, preferably DNA-based arrays, provide a simple way to assess differential gene expression of a set of genes associated with a given disease. In some embodiments, 2 polynucleotides or more, and preferably at least 5 polynucleotides having unique sequences selected from SEQ ID NO:1 through SEQ ID NO:12 are presented in a DNA microarray, optionally with additional polynucleotides (including control polynucleotides, duplicates, and the like) for the analysis, such as expression analysis of the corresponding genes in various cell types. Microarray chips are well known to those of skill in the art (see, e.g., U.S. Pat. Nos. 6,308,170; 6,183,698; 6,306,643; 6,297,018; 6,287,850; 6,291,183, each incorporated herein by reference in its entirety). These are exemplary patents that disclose nucleic acid microarrays and those of skill in the art are aware of numerous other methods and compositions for producing microarrays.

The invention provides for a composition comprising a plurality of polynucleotide probes for use in detecting changes in expression of a large number of genes from HCC. As used herein, the term "polynucleotide probe" refers to a nucleic acid whose sequence comprises any of the sequences set forth in SEQ ID NOS: 1 through 12, or any fragment thereof. Preferably, the fragment is at least 9 nucleotides; also preferably, it is at least 15 to 20 nucleotides. Such a composition can be employed for the diagnosis and treatment of HCC from any etiology or disease in which the dysfunction or non-function of liver cells is implicated or suspected. It should be understood that sequences of SEQ ID NO:1-12 are merely exemplary sequences of each of the genes TERT, GPC3, gankyrin, survivin, TOP2A, LYVE1, Ecadherin, IGFBP3, PDGFRA, TGFA, cyclin D1 and HGF, and that other variants of these genes also are known to those of skill in the art and that such variants may readily be along with or instead of the sequences of SEQ ID NO:1-12.

In one aspect, the invention provides a composition comprising a plurality of polynucleotide probes, wherein each of the polynucleotide probes comprises at least a portion of an expressed gene selected from the group consisting of TERT, GPC3, gankyrin, survivin, TOP2A, LYVE1, Ecadherin, IGFBP3, PDGFRA, TGFA, cyclin D1 and HGF.

The composition is particularly useful as hybridizable array elements in a microarray for monitoring the expression of a plurality of target polynucleotides. The microarray comprises a substrate and the hybridizable nucleic acid array elements. The microarray is used, for example, in the diagnosis and treatment monitoring of a liver cancer.

The term "microarray" refers to an ordered arrangement of hybridizable array elements. The array elements are arranged so that there are preferably at least two or more different array elements, more preferably at least 100 array elements, and most preferably at least 1,000 array elements, on a solid support. Preferably, the solid support is a 1 cm2 substrate surface, bead, paper, nylon or other type of membrane, filter, chip, glass slide, or any other suitable solid support. The hybridization signal from each of the array elements is individually distinguishable. In a preferred embodiment, the array elements comprise polynucleotide probes.

A "polynucleotide" refers to a chain of two or more nucleotides. Preferably, the chain has from about 10, 15, 20, 25, 30, 35, 40, 45, 50, 75 to 10,000 nucleotides, more preferably from about 100 to 3,500 nucleotides. An "oligonucleotide" refers to a chain of nucleotides extending from 2-100 nucleotides, and preferably 9-79 nucleotides. The term "probe" refers to a polynucleotide sequence capable of hybridizing with a target sequence to form a polynucleotide probe/target complex. A "target polynucleotide" refers to a chain of nucleotides to which a polynucleotide probe can hybridize by base pairing. In some instances, the sequences will be perfectly complementary (no mismatches) when aligned. In other instances, there may be up to a 10% mismatch.

A "plurality" refers to a group of at least 2 members, preferably 5 or more members, preferably at least 9 members, preferably to a group of at least about 100, and preferably to a group of at least about 1,000, members. The maximum number of members is unlimited, but is at least 100,000 members.

The term "gene" or "genes" refers to a nucleic acid (DNA, RNA or other polynucleotide derivatives) which can be of any origin (prokaryote, eukaryote, viral, etc.). The gene may encode, e.g., an antisense RNA, a ribozyme or a messenger (mRNA) that will be translated into a protein of interest. It includes genomic DNA, cDNA or mixed types (e.g., minigene). It may code for a mature polypeptide, a precursor (i.e., precursor intended to be secreted and comprising a signal sequence, a precursor to be matured by proteolytic cleavage, and the like), a fragment of a protein (truncated protein), a chimeric polypeptide originating from the fusion of diverse sequences or a mutated polypeptide displaying improved and/or modified biological properties. The gene may be isolated from any organism or cell by the conventional techniques of molecular biology (PCR, cloning with appropriate probes, chemical synthesis) and, if needed, its sequence may be modified by mutagenesis, PCR or any other protocol known in the art for sequence modification. The genes were initially identified from HCC cells.

The microarray can be used for large-scale genetic or gene expression analysis of a large number of target polynucleotides. The microarray can also be used in the diagnosis of liver diseases and in the monitoring of treatments of such diseases, particularly liver cancer. Further, the microarray can be employed to investigate an individual's predisposition to a liver disease, particularly to HCC. Furthermore, the microarray can be employed to investigate cellular responses to HCV infection, cancer drug treatment, and the like.

When the composition is employed as hybridizable array elements in a microarray, the array elements are preferably organized in an ordered fashion so that each element is present at a distinguishable, and preferably specified, location on the substrate. In preferred embodiments, because the array elements are at specified locations on the substrate, the hybridization patterns and intensities (which together create a unique expression profile) can be interpreted in terms of expression levels of particular genes and can be correlated with a particular disease or condition or treatment.

The composition comprising a plurality of polynucleotide probes can also be used to purify a subpopulation of mRNAs, cDNAs, genomic fragments and the like, in a sample. Typically, samples will include target polynucleotides of interest and other nucleic acids which may enhance the hybridization background; therefore, it may be advantageous to remove these nucleic acids from the sample. One method for removing the additional nucleic acids is by hybridizing the sample containing target polynucleotides with immobilized polynucleotide probes under hybridizing conditions. Those nucleic acids that do not hybridize to the polynucleotide probes are removed and may be subjected to analysis or discarded. At a later point, the immobilized target polynucleotide probes are released in the form of purified target polynucleotides.

Microarray production is well known to those of skill in the art. The nucleic acid probes can be genomic DNA or cDNA or mRNA, or any RNA-like or DNA-like material, such as peptide nucleic acids, branched DNAs, and the like. The probes can be sense or antisense polynucleotide probes. Where target polynucleotides are double-stranded, the probes may be either sense or antisense strands. Where the target polynucleotides are single-stranded, the probes include complementary single strands.

In one embodiment, the probes are cDNAs. The size of the DNA target sequence may vary and is preferably from 100 to 10,000 nucleotides, more preferably from 150 to 3,500 nucleotides.

The probes can be prepared using a variety of synthetic or enzymatic techniques, which are well known in the art. The probes can be synthesized, in whole or in part, using chemical methods well known in the art (Caruthers et al., Nucleic Acids Res., Symp. Ser., 215-233, 1980). Alternatively, the probes can be generated, in whole or in part, enzymatically.

A nucleotide analog can be incorporated into the probes by methods well known in the art. The only requirement is that the incorporated nucleotide analog must serve to base pair with a target nucleotide, or must be compatible with the base pairing activities of other probe nucleotides. For example, certain guanine nucleotides can be substituted with hypoxanthine, which base pairs with cytosine residues. However, these base pairs are less stable than those between guanine and cytosine. Alternatively, adenine nucleotides can be substituted with 2,6-diaminopurine, which can form stronger base pairs than those between adenine and thymidine.

Additionally, the probes can include nucleotides that have been derivatized chemically or enzymatically. Typical chemical modifications include derivatization with acyl, alkyl, aryl or amino groups.

The polynucleotide probes can be immobilized on a substrate. Preferred substrates are any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound. Preferably, the substrates are optically transparent.

Complementary DNA (cDNA) can be arranged and then immobilized on a substrate. The probes can be immobilized by covalent means such as by chemical bonding procedures or UV irradiation. In one such method, a cDNA is bound to a glass surface which has been modified to contain epoxide or aldehyde groups. In another case, a cDNA probe is placed on a polylysine coated surface and then UV cross-linked (Shalon et al., PCT publication WO95/35505, incorporated herein by reference in its entirety). In yet another method, a DNA is actively transported from a solution to a given position on a substrate by electrical means (Heller et al., U.S. Pat. No. 5,605,662). Alternatively, individual DNA clones can be gridded on a filter. Cells are lysed, proteins and cellular components degraded, and the DNA coupled to the filter by UV cross-linking.

Furthermore, the probes do not have to be directly bound to the substrate, but rather can be bound to the substrate through a linker group. The linker groups are typically about 6 to 50 atoms long to provide exposure to the attached probe. Preferred linker groups include ethylene glycol oligomers, diamines, diacids and the like. Preferably, reactive groups on the substrate surface react with one of the terminal portions of the linker to bind the linker to the substrate. The other terminal portion of the linker is then functionalized for binding the probe.

The probes can be attached to a substrate by dispensing reagents for probe synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

In order to conduct sample analysis, a sample containing target polynucleotide(s) is provided. The samples can be any sample containing target polynucleotide(s) and can be obtained from any bodily fluid (blood, urine, saliva, phlegm, gastric juices, etc.), cultured cells (e.g., primary liver cells or cell lines), biopsies, or other tissue preparations.

DNA or RNA is isolated from the sample according to any of a number of methods well known to those of skill in the art. For example, methods of purification of nucleic acids are described in the art (Tijssen, Laboratory Techniques in Biochemistry and Molecular Biology Hybridization With Nucleic Acid Probes, Part I. Theory and Nucleic Acid Preparation, Elsevier, New York N.Y. 1993). In one embodiment, total RNA is isolated using the TRIZOL reagent (Life Technologies), and mRNA is isolated using oligo d(T) column chromatography or glass beads. Alternatively, when target polynucleotides are derived from an mRNA, the target polynucleotides can be a cDNA reverse-transcribed from an mRNA, an RNA transcribed from that cDNA, a DNA amplified from that cDNA, an RNA transcribed from the amplified DNA, and the like. When the target polynucleotide is derived from DNA, the target polynucleotide can be DNA amplified from DNA or RNA reverse-transcribed from DNA. In yet another alternative, the targets are target polynucleotides prepared by more than one method.

When target polynucleotides are amplified, it is desirable to amplify the nucleic acid sample and maintain the relative abundancies of the original sample, including low abundance transcripts. Total mRNA can be amplified by reverse transcription using a reverse transcriptase and a primer consisting of oligo d(T) and a sequence encoding the phage T7 promoter to provide a single-stranded DNA template. The second DNA strand is polymerized using a DNA polymerase and an RNase which assists in hydrolyzing the RNA strand of a DNA/RNA hybrid. After synthesis of the double-stranded DNA, T7 RNA polymerase is added, and RNA transcribed from the second DNA strand template (Van Gelder et al. U.S. Pat. No. 5,545,522). RNA can be amplified in vitro, in situ or in vivo (See Eberwine, U.S. Pat. No. 5,514,545).

Quantitation controls may be included within the sample to assure that amplification and labeling procedures do not change the true distribution of target polynucleotides in a sample. For this purpose, a sample is spiked with a known amount of a control target polynucleotide and the composition of probes includes reference probes which specifically hybridize to the control target polynucleotides. After hybridization and processing, the hybridization signals obtained should accurately reflect the amounts of control target polynucleotide added to the sample.

Prior to hybridization, it may be desirable to fragment the nucleic acid target polynucleotides. Fragmentation improves hybridization by minimizing secondary structure and cross-hybridization to other nucleic acid target polynucleotides in the sample or to noncomplementary polynucleotide probes. Fragmentation can be performed by mechanical or chemical means.

The target polynucleotides may be labeled with one or more labeling moieties (including reporters used to associate a detectable label with a compound of interest) to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as 3H, 14C, 32P, 33P or 35S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like.

Exemplary dyes include quinoline dyes, triarylmethane dyes, phthaleins, azo dyes, cyanine dyes, and the like. Preferably, fluorescent markers absorb light above about 300 nm, preferably above 400 nm, and usually emit light at wavelengths at least greater than 10 nm removed from, and preferably above, the wavelength of the light absorbed. Preferred fluorescent markers include fluorescein, phycoerythrin, rhodamine, lissamine, and Cy3 and Cy5 available from Amersham Pharmacia Biotech (Piscataway N.J.).

Labeling can be carried out during an amplification reaction, such as polymerase chain reactions and in vitro transcription reactions, or by nick translation or 5' or 3'-end-labeling reactions. When the label is incorporated after or without an amplification step, the label may be incorporated by using terminal transferase or by phosphorylating the 5' end of the target polynucleotide using, e.g., a kinase and then incubating overnight with a labeled oligonucleotide in the presence of T4 RNA ligase.

Alternatively, the labeling moiety can be incorporated after hybridization, i.e., after a probe/target complex has formed.

In certain embodiments, a polynucleotide comprising the sequence of any one of SEQ ID NOS: 1-12 may be used for the diagnosis of conditions or diseases with which the abnormal expression of any one of the genes encoded by SEQ ID NOS: 1-12 is associated. For example, a polynucleotide comprising any one of the sequences set forth in SEQ ID NOS: 1-12 may be used in hybridization or PCR (e.g., RT-PCR) assays of fluids or tissues (e.g., biopsies) to detect abnormal gene expression in liver cancer or tissue suspected of being cancerous. Such methods may be qualitative or quantitative in nature and may include Southern or Northern analyses, dot blot or other membrane-based technologies, PCR technologies, dip stick, pin, chip and ELISA technologies.

All of these techniques are well known in the art and their use is facilitated by the availability of commercial kits in many instances.

In addition, such assays may be useful in evaluating the efficacy of a particular therapeutic treatment regimen in animal studies, in clinical trials, or in monitoring the treatment of an individual patient. In order to provide a basis for the diagnosis of disease, a normal or standard profile for the expression of polynucleotides comprising any one of the sequences of SEQ ID NOS: 1-12 is preferably established. This generally involves a combination of body fluids or cell extracts taken from normal subjects, either animal or human, under conditions suitable for hybridization or amplification. Standard hybridization may be quantified by comparing the values obtained for normal subjects with a dilution series of a given leukemia-related gene product encoded by a polynucleotide comprising any sequence set forth in SEQ ID NOS: 1-12 run in the same experiment where a known amount of purified gene product is used. Standard values obtained from normal samples may be compared with values obtained from samples from subjects affected by abnormal gene expression in leukemic cells. Deviation between standard and subject values establishes the presence of a disease or condition.

Once a disease condition is diagnosed, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of time.

PCR as described in U.S. Pat. Nos. 4,683,195 and 4,965,188 provides additional uses for oligonucleotides based upon any one of the sequences set forth in SEQ ID NOS: 1-12. Such oligomers are generally chemically synthesized, but they may be generated enzymatically or produced from a recombinant source as described herein. Oligomers are preferably employed in perfectly complementary pairs, one with a sense orientation and one with an antisense orientation, for identification of particular gene expression and attendant disease or disorder diagnosis and/or monitoring. The same two oligomers, nested sets of oligomers, or even a degenerate pool of oligomers may be employed under less stringent conditions for detection and/or quantitation of closely related DNA or RNA sequences.

Additionally, methods to quantify the expression of a particular molecule include radiolabeling (Melby et al., J. Immunol. Methods 159: 235-44, 1993) or biotinylating (Duplaa et al., Anal. Biochem. 229-36, 1993) nucleotides, coamplification of a control nucleic acid, and standard curves to which the experimental results are compared. Quantitation of multiple samples may be accelerated by running the assay in an ELISA format where the oligomer of interest is presented in various dilutions and a spectrophotometric or colorimetric response gives rapid quantitation. For example, the presence of abnormal levels of any one of the proteins encoded by the sequences of SEQ ID NOS: 1-12 in extracts of biopsied liver tissues may indicate the onset of a particular disease. A definitive diagnosis of this type may allow health professionals to begin aggressive treatment and prevent further worsening of the condition. Similarly, further assays can be used to monitor the progress of a patient during treatment.

The arrays will be used in hybridization and detection studies for determining presence of HCC. Hybridization causes a denatured probe and a denatured complementary target to form a stable nucleic acid duplex through base pairing. Hybridization methods are well known to those skilled in the art (see, e.g., Ausubel, Short Protocols in Molecular Biology, John Wiley & Sons, New York N.Y., units 2.8-2.11, 3.18-3.19 and 4-6-4.9, 1997). Conditions can be selected for hybridization where only an exactly or perfectly complementary target and probe can hybridize, i.e., each base must interact with its complementary base. Alternatively, conditions can be selected where a target and a probe have mismatches but are still able to hybridize. Suitable conditions can be selected, for example, by varying the concentrations of salt in the prehybridization, hybridization and wash solutions, by varying the hybridization and wash temperatures, or by varying the polarity of the prehybridization, hybridization or wash solutions.

Hybridization can be performed at low stringency with buffers, such as 6×SSPE with 0.005% Triton X-100 at 37° C., which permits hybridization between target and probes that contain some mismatches to form target polynucleotide/probe complexes. Subsequent washes are performed at higher stringency with buffers, such as 0.5×SSPE with 0.005% Triton X-100 at 50° C., to retain hybridization of only those target/probe complexes that contain exactly complementary sequences. Alternatively, hybridization can be performed with buffers, such as 5×SSC/0.2% SDS at 60° C. and washes are performed in 2×SSC with 0.2% SDS and then with 0.1× SSC. Background signals can be reduced by the use of detergent, such as sodium dodecyl sulfate, Sarcosyl or Triton X-100, or a blocking agent, such as salmon sperm DNA.

After hybridization, the microarray is washed to remove non-hybridized nucleic acids, and complex or hybrid formation between the hybridizable array elements and the target polynucleotide(s) is detected. Methods for detecting complex formation are well known to those skilled in the art. In a preferred embodiment, the target polynucleotides are labeled with a fluorescent label, and measurement of levels and patterns of fluorescence indicative of complex formation is accomplished by fluorescence microscopy, preferably confocal fluorescence microscopy. An argon ion laser excites the fluorescent label, emissions are directed to a photomultiplier, and the amount of emitted light is detected and quantitated. The detected signal is proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance/expression level of each hybridized target polynucleotide.

Typically, microarray fluorescence intensities can be normalized to take into account variations in hybridization intensities when more than one microarray is used under similar test conditions. In a preferred embodiment, individual probe/target hybridization intensities are normalized using the intensities derived from internal normalization controls contained on each microarray.

Expression profiles may be generated using the compositions. The expression profile can be used to detect changes in the expression of genes implicated in liver disease.

The expression profile includes a plurality of detectable complexes. Each complex is formed by hybridization of one or more nucleic acids to one or more complementary target polynucleotides. At least one of the nucleic acids, and preferably a plurality thereof, is exposed to a potentially complementary target polynucleotide forming at least one, and preferably a plurality, of complexes. A complex is detected by incorporating at least one labeling moiety in the complex as described above. The expression profiles provide "snapshots" that can show unique expression patterns that are characteristic of the presence or absence of a disease or condition.

After performing hybridization experiments and interpreting detected signals from a microarray, particular probes can be identified and selected based on their expression patterns. Such probe sequences can be used to clone a full-length gene or to produce a polypeptide.

The composition comprising a plurality of probes can be used as hybridizable elements in a microarray. Such a microarray can be employed in several applications including diagnostics, prognostics and treatment regimens, drug discovery and development, toxicological and carcinogenicity studies, forensics, pharmacogenomics, and the like.

In one aspect of the invention, the microarray is used to monitor the progression of disease. Researchers can assess and catalog the differences in gene expression between healthy and diseased tissues or cells. By analyzing changes in patterns of gene expression, diseases or conditions can be diagnosed at earlier stages, before the patient is symptomatic. The invention can also be used to monitor the efficacy of treatment. For some treatments with known side effects, the microarray is employed to "fine tune" the treatment regimen. A dosage is established that causes a change in genetic expression patterns indicative of successful treatment. Expression patterns associated with undesirable side effects are avoided. This approach is expected to be more sensitive and rapid than waiting for the patient to show inadequate improvement, or to manifest side effects, before altering the course of treatment.

Alternatively, animal models which mimic a disease, rather than patients, are used to characterize expression profiles associated with a particular disease or condition. This gene expression data is useful in diagnosing and monitoring the course of the disease or condition in a patient, in determining gene targets for intervention, and in testing treatment regimens.

Also, the microarray is useful in rapidly screening large numbers of candidate drug molecules, looking for ones that produce an expression profile similar to those of known therapeutic drugs, with the expectation that molecules with the same expression profile will likely have similar therapeutic effects. Thus, the invention provides the means to determine the molecular mode of action of a drug.

In other embodiments, the present invention relates to methods of screening for compounds which can be used to treat liver cancer, especially hepatocellular carcinoma (HCC). The present invention also relates to methods of treating or ameliorating cancers, in particular, liver cancer, especially hepatocellular carcinoma, by administering the drugs selected by the screening methods of the present invention. The present invention further relates to pharmaceutical compositions for treating or ameliorating liver cancers, as well as kits containing such compositions.

It is well known that various cancer cells exhibit altered levels of gene expression compared to the normal cells. The present methods for screening potential anti-cancer drugs may employ cells that have express one or more of the genes selected from the group consisting of TERT, GPC3, gankyrin, survivin, TOP2A, LYVE1, Ecadherin, IGFBP3, PDGFRA, TGFA, cyclin D1 and HGF. Such cells may be primary HCC cancer cells, cell lines derived from such cancer cells or may even be recombinant cells that have been engineered to express the genes of interest in a manner that mimics HCC gene profile discussed herein. Accordingly, the present invention provides a method of screening for an agent comprising: contacting the desired cancer cell that has an increased expression of one or more genes selected from the group consisting of TERT, Glypican-3 (GPC3), gankyrin (PSMD10), and survivin (BRIC5), and TOP2A (Group A, i.e., that set of five genes shown in the Example to be up-regulated in HCC) and/or a decreased expression of one or more genes selected from the group consisting of LYVE1 (XLKD1), E-cadherin (CDH1), IGFBP3, PDGFRA, TGFA, cyclin D1 (CCND1) and HGF (Group B, i.e., that set of seven genes shown in the Example to be down-regulated in HCC) with a candidate substance; determining whether the candidate substance alters the level of expression of the genes (e.g., decreases the expression of the one or more genes of Group A or increases the level of expression of the one or more genes in Group B) as compared to the level of expression of those genes in that cell in the absence of the candidate substance; wherein if the candidate substance achieves an appropriate alteration in the expression of the genes tested will be indicative of the candidate substance being useful for the treatment of liver cancer.

In a specific embodiment, the cancer is liver cancer originating from the liver, preferably HCC, that overexpresses a gene selected from Group A and/or underexpresses a gene selected from Group B.

Cytotoxicity of candidate substances can be measured by various methods known to ordinary skill in the art, including, but not limited to, LDH-release assay and Cr51-release assay. By employing various cancer cell cultures which overexpress particular enzymes having broad spectrum of substrates, the screening method of the present invention can be applied to drug discoveries for other types of cancers than liver cancer.

As used herein the term "candidate substance" refers to any molecule that is capable of modulating the expression of the genes identified herein. Thus, it could be a molecule or agent that modulates protein activity of the expression products of one of the genes identified herein. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known anti-cancer agents. The active compounds may include fragments or parts of naturally-occurring compounds or may be only found as active combinations of known compounds which are otherwise inactive. However, prior to testing of such compounds in humans or animal models, it will be necessary to test a variety of candidates to determine which ones have potential.

Accordingly, the active compounds may include fragments or parts of naturally-occurring compounds or may be found as active combinations of known compounds which are otherwise inactive. Accordingly, the present invention provides screening assays to identify agents which return the expression of one or more genes selected from TERT, GPC3, gankyrin, survivin, TOP2A, LYVE1, Ecadherin, IGFBP3, PDGFRA, TGFA, cyclin D1 and HGF from the pattern seen in HCC liver cells to normal expression pattern/levels seen in normal, non-cancer liver cells. Compounds isolated from natural sources, such as animals, bacteria, fungi, plant sources, including leaves and bark, and marine samples may be assayed as candidates for the presence of potentially useful pharmaceutical agents. Alternatively, the agents to be screened could also be derived or synthesized from chemical compositions or man-made compounds. Thus, it is understood that the candidate substance identified by the present invention may be polypeptide, polynucleotide, small molecule inhibitors or any other inorganic or organic chemical compounds that may be designed through rational drug design starting from known stimulators or inhibitors of apoptosis.

The candidate screening assays are simple to set up and perform. Thus, in assaying for a candidate substance, after obtaining the appropriate cell, one will admix a candidate substance with the cell, under conditions which would allow measurable expression of one or more of the identified genes to occur. In this fashion, one can measure the ability of the candidate substance to stimulate or inhibit the expression of the genes in the cell in the absence of the candidate substance.

"Effective amounts" in certain circumstances are those amounts effective to reproducibly alter a given expression pattern and/or cancer phenotype e.g., appearance, from the cell in comparison to the normal levels of such an event. Compounds that achieve significant appropriate changes in such activity will be used.

Significant changes in expression or function are represented by an increase/decrease in apoptotic activity of at least about 30%-40%, and most preferably, by changes of at least about 50%, with higher values of course being possible. The active compounds of the present invention also may be used for the generation of antibodies which may then be used in analytical and preparatory techniques for detecting and quantifying further such inhibitors.

There are a number of different libraries used for the identification of small molecule modulators including chemical libraries, natural product libraries and combinatorial libraries comprised or random or designed peptides, oligonucleotides or organic molecules. Chemical libraries consist of structural analogs of known compounds or compounds that are identified as hits or leads via natural product screening or from screening against a potential therapeutic target. Natural product libraries are collections of products from microorganisms, animals, plants, insects or marine organisms which are used to create mixtures of screening by, e.g., fermentation and extractions of broths from soil, plant or marine organisms. Natural product libraries include polypeptides, non-ribosomal peptides and non-naturally occurring variants thereof. Combinatorial libraries are composed of large numbers of peptides oligonucleotides or organic compounds as a mixture. They are relatively simple to prepare by traditional automated synthesis methods, PCR cloning or other synthetic methods. Of particular interest will be libraries that include peptide, protein, peptidomimetic, multiparallel synthetic collection, recombinatorial and polypeptide libraries. A review of combinatorial libraries and libraries created therefrom, see Myers Curr. Opin. Biotechnol. 8: 701 707 (1997). A candidate modulator identified by the use of various libraries described may then be optimized to modulate activity or expression of a given cancer-associated gene through, for example, rational drug design.

It will, of course, be understood that all the screening methods of the present invention are useful in themselves notwithstanding the fact that effective candidates may not be found. The invention provides methods for screening for such candidates, not solely methods of finding them.

Twelve genes have been identified herein as being of particular interest for determining the presence of cancerous HCC cells in small liver nodules. The genes are TERT, GPC3, gankyrin, survivin, TOP2A, LYVE1, Ecadherin, IGFBP3, PDGFRA, TGFA, cyclin D1 and HGF and their sequences are known to those of skill in the art. For example, Table 1 below provides the Genbank Accession numbers for these and other genes that could serve as useful markers for HCC. In some embodiments, it may be desirable to achieve expression or knock-out expression of those genes in specific cells. In some embodiments of treatment methods, the expression of the genes (e.g., oncogenes) is abrogated in order to ameliorate the deleterious oncogenic phenotypes that result from the expression of such genes in cells. For example, it is contemplated that antisense oligonucleotides directed against such genes will prove useful in selectively reducing the expression of the gene without interfering with the function of other normally expressed genes.

Any reference to a nucleic acid should be understood as encompassing a vector comprising that polynucleotide and a host cell containing that vector or nucleic acid and, in some cases, capable of expressing the protein product of that nucleic acid. Cells expressing nucleic acids are useful in certain therapeutic applications, and methods of making and using such cells are described below.

The nucleic acid sequences disclosed in SEQ ID NOS: 1-12 are expected to be found in genomic DNA, cDNA, mRNA, as well as recombinant and synthetic sequences and partially synthetic sequences, which may encode an entire protein, polypeptide, or allelic variant thereof.

Nucleic acids having sequences corresponding to any one of SEQ ID NOS:1-12 may be obtained from genomic DNA, i.e., cloned directly from the HCC cells. However, the nucleic acid also could be obtained from complementary DNA (cDNA). Also contemplated is a cDNA plus a natural intron or an intron derived from another gene; such engineered molecules are sometimes referred to as "mini-genes." These and other nucleic acids are useful as markers of HCC, and therefore are markers for liver cancer generally.

The term "cDNA" is intended to refer to DNA prepared using messenger RNA (mRNA) as a template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are targets in antisense methods of modulating gene expression.

It may be advantageous to combine portions of genomic DNA with cDNA or synthetic sequences to generate specific constructs. For example, where an intron is desired in the ultimate construct, a genomic clone is suitable. The cDNA or a synthesized polynucleotide may provide more convenient restriction sites for the remaining portion of the construct and, therefore, would be used for the rest of the sequence.

As used herein, the term "complementary sequences" means nucleic acid sequences that are substantially complementary, or as defined as being capable of hybridizing to a nucleic acid having a sequence of SEQ ID NOS: 1-12 under stringent conditions. Those of skill in the art will understand what is meant by stringent conditions and are referred to page 11.45 of Molecular Cloning: A Laboratory Manual, $2^{nd}$ Ed. Cold Spring Harbor Laboratory Press, Cold Spring Harbor, N.Y., or the conditions set forth in the Summary of the Invention, above.

The term "nucleic acid" as used herein also includes antisense nucleic acids. Antisense nucleic acids are able to bind to a specific mRNA through base-pairing, thereby interfering with protein expression. RNAi, may also be employed where, e.g., a synthesized 21-base double-stranded RNA is transfected into a mammalian cell. This double-stranded RNA will hybridize to an endogenously expressed target transcript, which will then be degraded by RNases, thereby interfering with protein expression.

The hybridizing nucleic acids may be relatively short (i.e., oligonucleotides). Nucleic acids, e.g., oligonucleotides, that specifically hybridize to any of the nucleic acid sequences of SEQ ID NO: 1-12 are useful as probes and/or primers. As used herein, an oligonucleotide that "specifically hybridizes" to a nucleic acid means that hybridization under suitably (e.g., high) stringent conditions allows discrimination of one or a few hybridizing sequences, preferably one sequence, from other sequences. Although shorter oligomers are easier to make and increase in vivo accessibility, numerous other factors are involved in determining the specificity of hybridization. Both potential binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others may be used. Longer polynucleotides encoding 250, 500, or 1000 nucleotides and longer are contemplated as well. Such oligonucleotides will find use, for example, as probes in Southern and Northern blots and as primers in amplification reactions.

Microarrays of the invention comprise a plurality of polynucleotides, the plurality comprising, e.g., at least 2 polynucleotides and preferably between 5 and 71 polynucleotides, wherein each enumerated polynucleotide has a distinct sequence selected from the group consisting of SEQ ID NOS: 1-12. In this context, an enumerated polynucleotide is a polynucleotide having a distinct sequence of any one of SEQ ID NOS: 1-12. Microarrays may have more than one polynucleotide that have a particular sequence selected from SEQ ID NOS:1-12. The microarrays may also have non-enumerated polynucleotides, e.g., control polynucleotides for use in hybridization-based assays using the microarray, as well as duplicates of enumerated and/or non-enumerated polynucleotides.

Hybridization means contacting two or more nucleic acids under conditions suitable for base pairing. Hybridization includes interaction between partially or perfectly complementary nucleic acids. Suitable hybridization conditions are well known to those of skill in the art. In certain applications, it is appreciated that lower stringency conditions may be required. Under these conditions, hybridization may occur even though the sequences of the interacting strands are not perfectly complementary, being mismatched at one or more positions. Conditions may be rendered less stringent by adjusting conditions in accordance with the knowledge in the art, e.g., increasing salt concentration and/or decreasing temperature. Suitable hybridization conditions are those conditions that allow the detection of gene expression from identifiable expression units such as genes. Preferred hybridization conditions are stringent hybridization conditions, such as hybridization at 42° C. in a solution (i.e., a hybridization solution) comprising 50% formamide, 1% SDS, 1 M NaCl, 10% dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration, as described in Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

One method of using probes and primers is in the search for gene expression in human cells. Normally, the target DNA will be a genomic or cDNA library, although screening may involve analysis of RNA molecules. By varying the stringency of hybridization and the target binding site (i.e., the sequence of the probe, corresponding to a subset of one of the sequences set forth at SEQ ID NOS: 1-12), different degrees of homology are expected to result in hybridization.

Given the foregoing disclosure of the nucleic acid constructs, it is possible to produce the gene product of any of the genes comprising the sequence of SEQ ID NO:1-12 by routine recombinant DNA/RNA techniques. A variety of expression vector/host systems may be utilized to contain and express the coding sequence. These include, but are not limited to, microorganisms such as bacteria transformed with recombinant bacteriophage, plasmid, phagemid, or cosmid DNA expression vectors; yeast transformed with yeast expression vectors; insect cell systems infected with viral expression vectors (e.g., baculovirus); plant cell systems transfected with virus expression vectors (e.g., Cauliflower Mosaic Virus, CaMV; Tobacco Mosaic Virus, TMV) or transformed with bacterial expression vectors (e.g., Ti or pBR322 plasmid); or even animal cell systems. Mammalian cells that are useful in recombinant protein productions include, but are not limited to, VERO cells, HeLa cells, Chinese hamster ovary (CHO) cells, COS cells (such as COS-7), WI38, BHK, HepG2, 3T3, RIN, MDCK, A549, PC12, K562 and HEK 293 cells.

Throughout this application, the term "expression construct" or "expression vector" is meant to include any type of genetic construct containing a nucleic acid coding for a gene product in which part or all of the nucleic acid encoding sequence is capable of being transcribed. The transcript may be translated into a protein and this process may be facilitated by inclusion of a ribosome binding site and/or a stop codon(s) in the expression vector, but it need not be. In certain embodiments, expression includes both transcription of a DNA (e.g., a gene) and translation of the cognate mRNA into a protein gene product.

The nucleic acid encoding a gene product is under transcriptional control of a promoter. A "promoter" refers to a DNA sequence recognized by the native synthetic machinery of the cell, or introduced synthetic machinery, required to initiate the specific transcription of the DNA. The phrase "under transcriptional control" means that the promoter is in the correct location and orientation in relation to the coding region of interest to control RNA polymerase initiation and appropriate extension of the nascent mRNA corresponding to the gene.

The term "promoter" is given its ordinary meaning in the art and is used herein to preferably refer to a group of transcriptional control modules that are clustered around the initiation site for eukaryotic RNA polymerase II. Additional promoter elements regulate the frequency of transcriptional initiation. Typically, these are located in the region 30-110 bp upstream of the transcription start site, although a number of promoters have recently been shown to contain functional elements downstream of the start site as well, and constructs containing such promoters are contemplated by the invention. The spacing between promoter elements frequently is flexible, so that promoter function is preserved when elements are inverted or moved relative to one another. In the tk promoter, for example, the spacing between promoter elements can be increased to 50 bp before activity begins to decline. Depending on the promoter, it appears that individual elements can function either cooperatively or independently to activate transcription.

The particular promoter employed to control the expression of a nucleic acid sequence of interest is not believed to be important, as long as it is capable of directing the expression of the nucleic acid in the cell of interest. Thus, where a bacterial host cell is used, it is preferable to position the nucleic acid coding region adjacent to, and under the control of, a promoter that is capable of being expressed in a bacterial cell. Generally speaking, such a promoter is a bacterial or a phage promoter.

Suitable promoters for prokaryotes include, for example, the trp promoter (de-repressible by tryptophan deprivation), the lac promoter (inducible with the galactose analog IPTG), the β-lactamase promoter, and the lambda phage-derived $P_L$ promoter (derepressible by temperature variation if the $cI_{ts}$ marker is also used in the expression system). Other useful promoters include those for alpha-amylase, protease, Spo2, spac, and hybrid or fusion promoters, such as tac promoters. Preferred promoters include the kanamycin resistance promoter, G13, and the endogenous or native promoter for whichever gene is being introduced.

Promoters that may be used for expression in yeast include the 3-phosphoglycerate kinase promoter and those for other glycolytic enzymes, as well as promoters for alcohol dehydrogenase and yeast phosphatase. Also suited are the promoters for transcription elongation factor (TEF) and lactase. Mammalian expression systems generally may include the SV40 promoter, known constitutive promoters functional in such cells, or regulable promoters such as the metallothionein promoter, which is controlled by heavy metals or glucocorticoid concentration.

All of the above promoters, well known and readily available to those of skill in the art, can be used to obtain controlled and/or high-level expression of the coding sequence of interest. The use of other viral or mammalian cellular, viral or bacteriophage promoters which are well known in the art to achieve expression of a coding sequence of interest are contemplated as well, provided that the levels of expression are sufficient for a given purpose. By employing a promoter with well-known properties, the level and pattern of expression of the protein of interest following transfection or transformation can be optimized.

Selection of a promoter that is regulated in response to a specific physiologic or synthetic signal(s) can permit inducible or de-repressible (i.e., controllable) expression of the gene product. Several such promoter systems are available for production of viral vectors. One exemplary system is the ecdysone system (Invitrogen, Carlsbad, Calif.), which is designed to allow regulated expression of a gene of interest in mammalian cells. It consists of a tightly regulated expression mechanism that allows barely detectable basal level expression of a heterologous DNA such as a transgene, with over 200-fold inducibility of expression.

Translation control sequences include a ribosome binding site (RBS) in prokaryotic systems, whereas in eukaryotic systems translation may be controlled by a "TATA" box sequence which may also contain an initiation codon such as AUG.

Another regulatory element contemplated for use in the invention is an enhancer. These are genetic elements that increase, or enhance, transcription; enhancers may be located a considerable distance from a functionally related coding region (separation of several kb or more), the relative locations of enhancer and coding region is not specific (the enhancer may be 5', 3' or internal to the coding region), and the orientation of the enhancer itself is not specific (some enhancers function in inverted orientation). Promoters and enhancers are often overlapping and contiguous, often seeming to have a very similar modular organization. Enhancers useful in the invention are well known to those of skill in the art and will depend on the particular expression system being employed (Scharf et al., Results Probl Cell Differ, 20, 125-62, 1994; Bittner et al., Methods in Enzymol, 15, 516-544, 1987).

There are a number of ways in which expression vectors may be introduced into cells. In certain embodiments of the invention, the expression construct comprises a virus or engineered construct derived from a viral genome. In other embodiments, non-viral delivery is contemplated. The ability of certain viruses to enter cells via receptor-mediated endocytosis, to integrate into host cell genomes, and to express viral genes stably and efficiently have made them attractive candidates for the transfer of foreign genes into mammalian cells (Ridgeway, In: Vectors: A survey of molecular cloning vectors and their uses, Rodriguez and Denhardt (eds.), Stoneham: Butterworth, pp. 467-492, 1988; Nicolas et al., In: Vectors: A survey of molecular cloning vectors and their uses, Rodriguez & Denhardt (eds.), Stoneham: Butterworth, pp. 493-513, 1988; Baichwal et al., In: Gene Transfer, Kucherlapati ed., New York, Plenum Press, pp. 117-148, 1986; Temin, In: Gene Transfer, Kucherlapati (ed.), New York: Plenum Press, pp. 149-188, 1986).

Several non-viral methods for the transfer of expression constructs into cultured bacterial cells are contemplated by the invention. This section provides a discussion of methods and compositions of non-viral gene transfer. DNA constructs are generally delivered to a cell and, in certain situations, the nucleic acid or the protein to be transferred may be transferred using non-viral methods. The non-viral methods include calcium phosphate precipitation, direct microinjection, DNA-loaded liposomes, cell sonication, gene bombardment using high velocity microprojectiles, conjugation and receptor-mediated transfection. The expression construct also may be entrapped in a liposome. Also contemplated in the invention are various commercial approaches involving "lipofection" technology. Other vector delivery systems that can be employed to deliver a nucleic acid encoding a given gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu et al., 1993, supra). Receptor-mediated gene targeting also can be used. Another embodiment of the invention for transferring a naked DNA expression construct into cells involves particle bombardment. This method depends on the ability to accelerate DNA-coated microprojectiles to a high velocity, allowing them to pierce cell membranes and enter cells without killing them (Klein et al., Nature, 327:70-73, 1987). Several devices for accelerating small particles have been developed. One such device relies on a high-voltage discharge to generate an electrical current, which in turn provides the motive force (Yang et al., Proc. Natl. Acad. Sci. (USA), 87:9568-9572, 1990). The microprojectiles used to date have consisted of biologically inert substances such as tungsten or gold beads.

Example

Experimental Determinations to Elucidate Molecular Signature to Discriminate Dysplastic Nodules from Early hepatocellular Carcinoma in HCV-Cirrhosis The following example presents preferred embodiments and techniques, but is not intended to limit the scope of the invention. Those of skill in the art will, in light of the present disclosure, appreciate that many changes can be made in the specific materials and methods which are disclosed and still obtain a like or similar result without departing from the spirit and scope of the invention.

Patients and Methods

Patients and samples. Samples were obtained from patients undergoing resection or liver transplantation in three University Hospitals in the U.S. (Mount Sinai Hospital, New York) and Europe (Hospital Clinic, Barcelona, Spain; and National Cancer Institute, Milan, Italy). Laboratory techniques have been centralized in the labs of the Division of Liver Diseases, Hematology/Oncology and the Center of Life Sciences of the Mount Sinai School of Medicine, New York. The research protocol was approved by the Institutional Review Boards of the three institutions and informed consent was obtained in all cases.

Characteristics of the samples. A total of 77 samples were selected to assess the gene transcriptional profiles. Twenty samples from patients with early HCC undergoing resection (15 cases) or liver transplantation (5 cases) were included as cases (Table 1). All patients presented with HCV-induced well- or moderately-differentiated HCC, with a median tumor size of 18 mm [14 cases less than 20 mm; range 8-45 mm]. Two cases showed presence of vascular invasion and/or satellite lesions at the pathological examination. Patients with HBV-positive markers, or a background of alcohol consumption, non-alcoholic steatohepatitis, hemochromatosis or other causes of chronic liver disease were excluded. Patients with lesions previously treated by loco-regional therapies—percutaneous ablation or chemoembolization/lipiodolization—were also excluded. The gene transcriptional profiles of these tumors were compared with 17 dysplastic nodules—10 low grade dysplastic nodules [median size: 8.5 mm (range: 6-12 mm)] and 7 high grade dysplastic nodules [median size: 8.5 mm (range: 7-15 mm)] obtained from patients undergoing liver transplantation. Results were compared with 10 non-tumoral cirrhotic tissues from HCC patients and 10 samples of normal tissue obtained from the healthy liver of patients undergoing resection for hepatic hemangioma (Sangiovanni et al., Gastroenterology, 126(4):1005-1014 (2004)), focal nodular hyperplasia (Sangiovanni et al., Gastroenterology, 126(4):1005-1014 (2004)), adenoma/cystadenoma (Bosch et al., Gastroenterology, 127(5 Suppl 1):S5-S16 (2004)), neuroendocrine tumor (Llovet et al., Lancet, 362:1907-1917 (2003)) and living donor liver transplantation (Llovet et al., Lancet, 362:1907-1917 (2003)).

The mRNA expression profiles of the selected candidate genes was additionally measured in 20 samples of advanced HCC to confirm the presence of a consistent dysregulation at more advanced stages of the disease.

Sample collection and pathological data. Once written informed consent was obtained, the main clinical and pathological variables of the patients were recorded. Fresh tissue specimens were collected in the Operating Room/Pathology Department and processed within one hour to minimize the alteration of gene expression due to ischemia. Samples were split in two. One part of each specimen was collected in either liquid nitrogen or RNAlater® solution (Ambion Corp, The Woodlands, Tex.), and stored at −80° C. until use, whereas the other half was formalin-fixed and paraffin-embedded for morphological examination and immunostaining analysis. In cases of liver transplantation, explanted livers were sectioned at 5-mm slices to identify all visible lesions. All nodules that on gross examination were distinct from the surrounding liver tissue in terms of size, color, texture or degree of bulging were recorded and examined microscopically (minimum diameter of 5 mm). Tissue sampling was handled by using thin sections (4 µM) of the target area, which was micro-dissected under a scanning microscope for PCR studies.

Pathological examination was considered the gold standard. Two expert pathologists reviewed each slide independently, then reached an agreement on the diagnosis of the lesions (ST and IF). Nodules were classified as either low-grade dysplastic nodules (LGDN), HGDN or HCC according to the terminology of the International Working Party (Aerts et al., Biotechniques, 36:84-86, 88, 90-91 (2004)). In addition, two pathological stages were defined among the 20 target HCC samples: 1. Very early HCC was defined as well-differentiated tumors<2 cm in diameter without vascular invasion or satellites. 2. Early HCC: HCC<2 cm with microscopic vascular invasion/satellites or 2-5 cm well-moderately differentiated HCC without vascular invasion/satellites or 2-3 nodules<3 cm well-differentiated. The key genes were further tested in 20 samples of patients with advanced HCC, including 10 samples of patients with macroscopic vascular invasion/diffuse HCC.

Quantitative Real Time Reverse Transcriptase-PCR(RT-PCR). RNA isolation, quality and cDNA synthesis. We collected 40 mg to 1000 mg of tissue from each lesion. Fresh tissue specimens collected were saturated in RNAlater-ICE® reagent (Ambion, Austin, Tex.) and quickly ground under liquid nitrogen to maintain the RNA integrity and enhance the yield. The resulting tissue powder was homogenized in Trizol® reagent (Invitrogen, Carlsbad, Calif.) with a Polytron homogenizer. Total RNA was extracted from tissue homogenates according to the manufacturer's instructions, and was additionally digested with RNase-free DNase and purified with RNeasy® columns (Qiagen, Valencia, Calif.). The purity of RNA samples was assessed by measuring the OD260/0D280 ratios on a Nanoprop ND-1000 spectrometer (Nanoprop, Wilmington, Del.), resulting in a ratio of 2.00-2.08 in all cases. The quality and integrity of RNA was measured by a bio-analyzer (Agilent, Palo Alto, Calif.). Complementary DNA was synthesized from 5 µg of purified total RNA derived from each sample using SuperScript III reverse transcriptase (Invitrogen, Carlsbad, Calif.) according to the manufacturers' instructions.

Real Time-RT-PCR. Expression of mRNA for genes of interest was measured by Taqman Real-time PCR method using an ABI PRISM 7900HT Sequence Detection System (Applied Biosystems, Foster City, Calif.). The probe and primer set for each gene was derived from Taqman Gene Expression Assays (Applied Biosystems). The real-time reactions were set up as triplicates for each gene in 384-well plates and run at the default PCR thermal cycling conditions: 50° C., 2 min; 95° C., 10 min; 40 cycles of 95° C., 15 sec and 60° C. 1 min. Median Conn. value from the triplicates was used in all the calculations.

Normalization and genes tested. Fifty-five genes were selected from a thorough review of previous studies identifying those consistently reported as potential molecular markers of early HCC or involved in any of the pathways of hepatocarcinogenesis (Table 1). Because of its more constant expression levels among HCC tissues, ribosomal RNA (18S) was chosen for normalization (Gong et al., Hepatology, 26:803 (1997)). To ensure the validity of using 18S to calculate the relative expression fold change, the 55 genes were tested together with the assay for 18S gene at 5 dilutions (2-fold series) of randomly selected HCC cDNA samples. All genes showed slope values (Ct versus log concentration blot) within a slope18S±0.1. Significant results were validated using SYBR green.

Immunohistochemistry. Formalin-fixed, paraffin-embedded tissue sections were baked at 55° C. overnight, deparaffinized in xylene, and rehydrated in a graded series of ethanol solutions. Antigen retrieval was performed by immersing the slides in 10 mmol/L citrate buffer, pH 6.0 and heating them in microwave at power level 10 for 3 minutes, followed by power level "7" for 10 minutes. To reduce background staining, the sections were incubated in 10% normal serum from the species in which the secondary antibody was raised. The optimal dilutions of the primary antibodies (monoclonal anti-GPC3 1:50, Zymed Laboratories, South San Francisco, Calif.; rabbit anti-survivin 1:250, Abcam) were applied to the sections for overnight in 4° C. After washing in PBS, sections were incubated with the biotinylated secondary antibodies for 30 minutes in 37° C. Endogenous peroxide was blocked by immersing the slides in 3% hydrogen peroxide for 15 minutes. The antibody binding was detected with avidinbiotin peroxidase complex system (Dako, Carpinteria, Calif.). Sections were then counterstained with hematoxylin, dehydrated in a graded series of alcohol and xylene, and coverslipped.

The variables measured were as follows: 1. Determination of immunostaining intensity (score 0-3+; 0=negative, 1=weak, 2=moderate, 3=strong). 2. Staining pattern (focal, diffuse) 3. Sub-cellular localization (membrane, cytoplasm or nucleus).

Statistical analysis. Results are expressed as mean±SD for continuous variables with normal distribution, and median (95 percent confidence interval) for the other continuous and categorical variables. All the RT-PCR calculations were analyzed by using the expression of each gene in a given sample (Ct) normalized by the level of 18S in the sample (Ct−Ct18S=dCt), and further adjusted by the gene expression in the control group (ddCt). Results are expressed as fold-changes (log 2 scale), considering the gene expression of the control group as 1. Comparisons between groups were done by the non-parametric Mann-Whitney test for continuous variables, and the Fisher exact test for comparison of proportions. The area under the receiving operating curves (ROC) was assessed for all the genes to discriminate dysplastic nodules and early cancer. Correlations were calculated with the nonparametric Spearman's coefficient.

Strategy for selecting the best model. Genes significantly dysregulated in HCC in comparison to dysplastic nodules by Mann-Whitney test, Fisher exact test and showing an area under the ROC curve (AUC)>0.8 were included in a multi-variate forward step-wise logistic regression analysis to determine the independent predictors of early HCC. In addition, ROC curves were used to establish the best cut-off to categorize each gene for the regression analysis.

The diagnostic accuracy of the gene signatures proposed was calculated by sensitivity, specificity, positive and negative predictive values and likelihood ratio, considering early HCC as the disease. The likelihood ratio for a positive result is the ratio of the chance of a positive result in a cancer sample to the chance of a positive result in the dysplastic sample. The molecular signatures identified were obtained from the analysis of two groups of genes: 1. Including 12 genes significantly and consistently up or down-regulated in HCC, 2. Including only the 5 genes significantly up-regulated in early HCC. A gene dendogram was obtained by hierarchical clustering of expression data by samples and genes using average linkage and Pearson correlation distance by using the TIGR-MEV program (Saeed et al., Biotechniques, 34:374-378 (2003)). All other calculations were done by the SPSS package (SPSS12.0, Inc. Chicago, Ill.).

Results

Gene Expression Profiles of Dysplastic Nodules and Early HCC.

Selection of the significant genes. Twelve genes were significantly, differentially expressed in early HCC compared with dysplastic nodules: five genes were up-regulated in cancer including TERT, Glypican-3 (GPC3), gankyrin (PSMD10), and survivin (BRIC5), TOP2A while seven were down-regulated including LYVE1 (XLKD1), E-cadherin (CDH1), IGFBP3, PDGFRA, TGFA, cyclin D1 (CCND1) and HGF (Table 3). Differential expression of all twelve genes was associated with an area under the ROC>0.8, and more than 2 fold-change (either up- or down-regulation). Among the up-regulated genes, the median increase of GPC3 was 18-fold, TERT 10.8-fold and survivin 2.2-fold increase in early HCC compared with dysplastic nodules. Among the downregulated genes, LYVE1 was decreased 12-fold in early HCC compared to dysplastic nodules, IGFBP3 8.5-fold, and E-cadherin 2.8-fold. A dendrogram heatmap graph was generated that displays a hierarchical clustering of these 12 genes and 37 samples according to the transcriptional profiles obtained by real time RT-PCR (FIG. 1). By using the 12-gene set, all early HCCs were properly classified, and only one dysplastic nodule was misclassified.

Figure 2B:
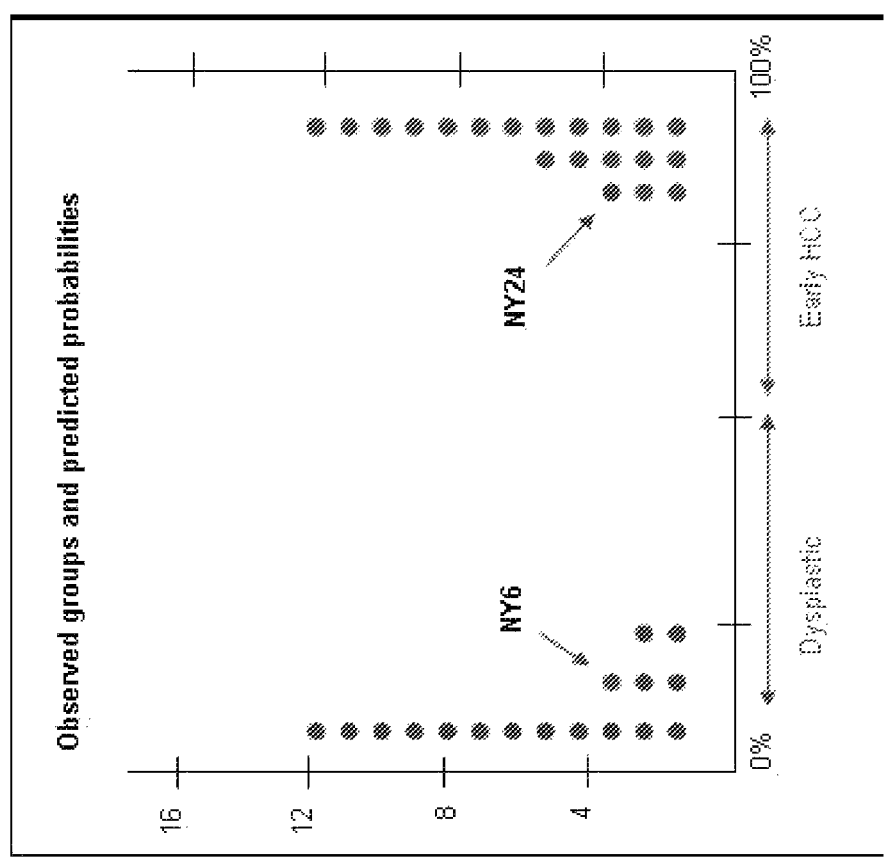
FIG. 2. Observed groups and predicted probabilities using the best model of combination of 3 genes (LYVE1, GPC3 and BRIC5). Graphic displaying the observed groups and predicted probabilities. Y axis shows number of samples, and X axis shows the percentage of certainty of classification of a given sample (0%=dysplastic nodule; 100%=early HCC). By using this model, only two samples were misclassified (arrows, NY24 and NY6). Overall, the accuracy of the model was of 94%.
Figure 3A:
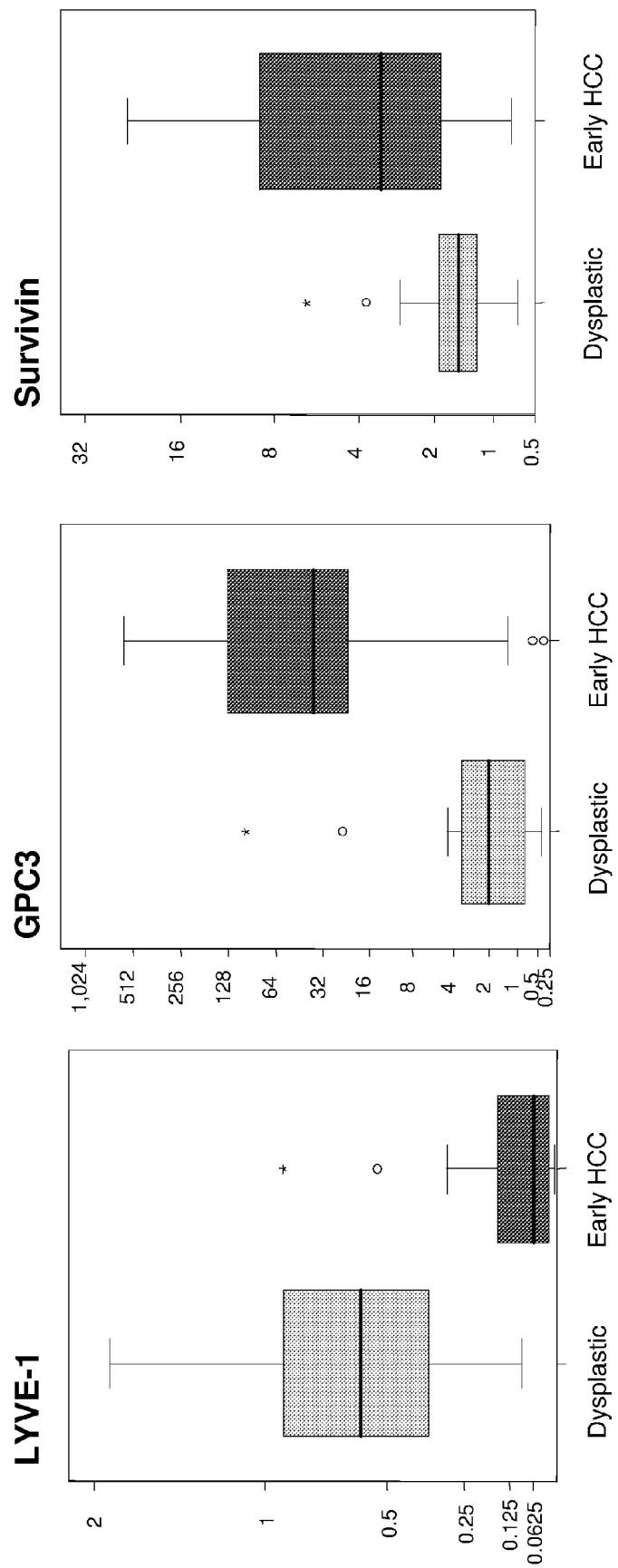
FIG. 3. 3A. Gene expression profiles of the 3 most informative genes comparing dysplastic nodules (n=17) and early HCC (n=20). Results are expressed as foldchange. Boxes reflect median gene expression (25-75 percentile). 3B. Area under the ROC curve considering HCC as disease: two genes were up-regulated, GPC3 (AUC=0.84) and survivin (AUC=0.8), and one was down-regulated LYVE1 (AUC=0.9).
Figure 3B:
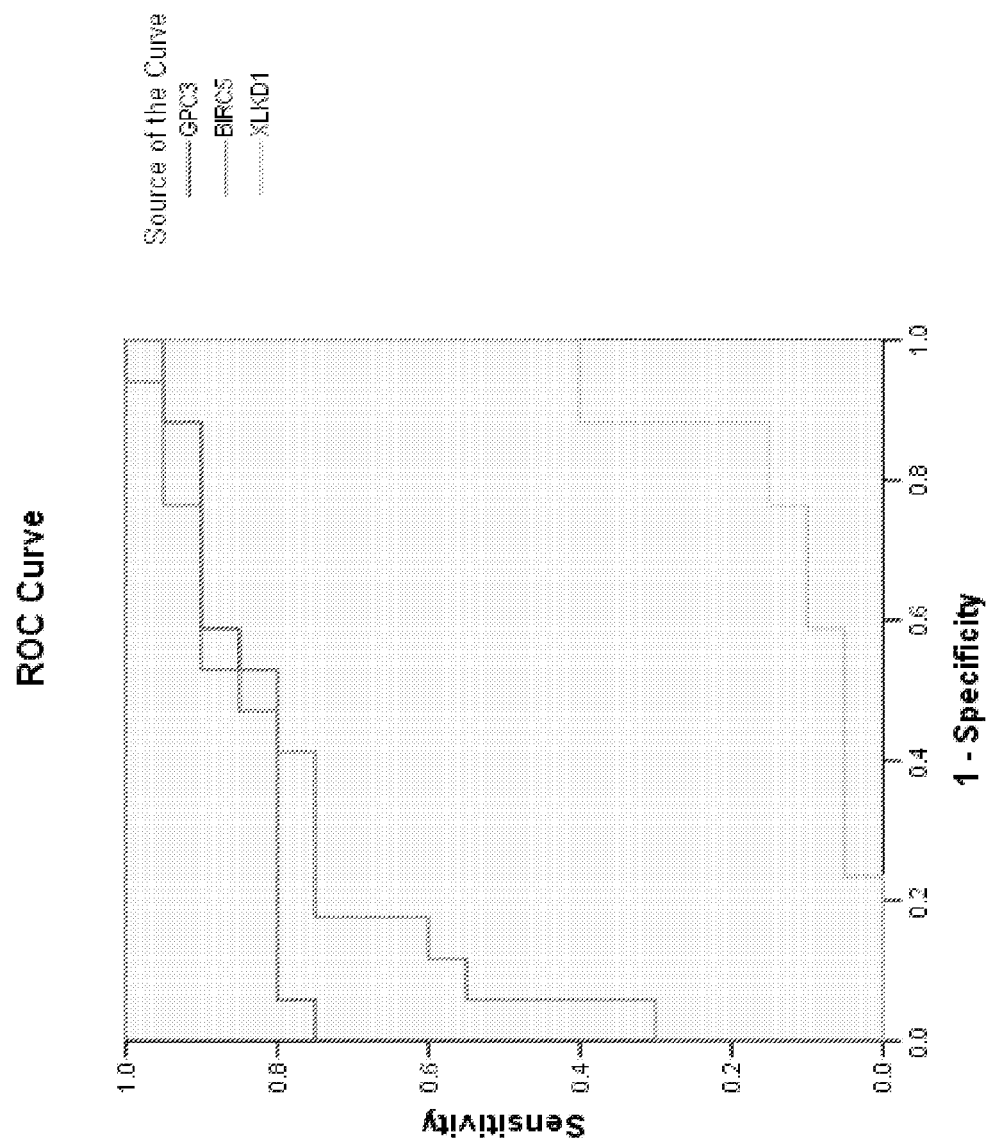

Gene signatures and accuracy of the models. To optimize the selection of the most informative set of genes we used logistic regression analysis categorizing the genes according to the best cut-off as determined by ROC curves. Several models were obtained depending on whether the analysis included the regression analysis with the 12 de-regulated genes, or only the 5 genes up-regulated in cancer (Table 4). Two 3-gene sets showed an accuracy of 94% in discriminating early HCC from dysplastic nodules. The best model includes LYVE1 (p=0.0001), GPC3 (p=0.0001) and survivin (p=0.001), with a sensitivity of 95%, specificity of 94%, positive predictive value of 95%, negative predictive value of 94% and likelihood ratio for a positive result of 16. When applying this model, only two samples were misclassified, one dysplastic nodule and one early HCC (NY24, NY6; FIG. 2). Transcriptional profiles of these genes along with the ROC curves are shown in FIG. 3. The other 3-gene set model included LYVE1, survivin and E-cadherin (accuracy 94%, sensitivity: 90%). We also searched for models including only genes up-regulated in early HCC. Two models were generated either combining GPC3-survivin or GPC3-TERT that showed an accuracy of 92%, although the latter presented a better likelihood ratio (5.8 vs 8.5, respectively).

Gene expression profiles of the 5 relevant genes in cirrhotic tissue and in advanced HCC. The gene transcriptional profiles of the five genes involved in the selected models were further tested in a set of 10 cirrhotic tissues and in 20 patients with HCC at more advanced stages of the disease, including 10 cases with macroscopic vascular invasion/diffuse hepatic disease. As shown in Table 5 and FIG. 4, all five genes displayed a consistent trend of up-regulation (GPC3, TERT, Survivin) or down-regulation (LYVE1, E-cadherin) at advanced stages of the neoplasm. All of them except LYVE1 demonstrated a significant up-regulation in cirrhosis compared with control samples [GPC3 14-fold (p=0.0001), TERT 1.8-fold (p=0.04), E-cadherin 3.9-fold (p=0.001) and Survivin 2.6-fold (p=0.005)].

Immunohistochemistry analysis. The immunostaining analysis was designed to assess the in situ protein expression of the up-regulated genes comprising the best molecular signature of early HCC (GPC3, survivin). The analysis was performed in 27 paired samples of non-tumoral cirrhotic tissue and 7 dysplastic nodules, 20 HCC samples (7 early HCC and 13 advanced HCC) and 3 healthy controls. All results are summarized in Table 6.

Figure 5C:
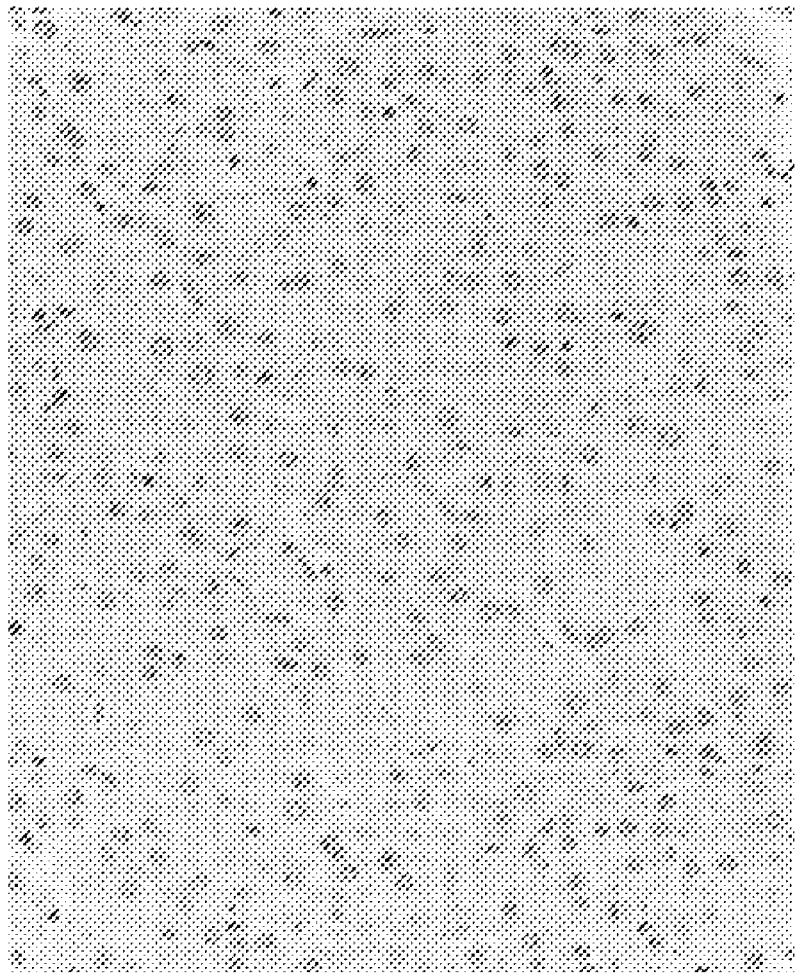
Figure 6B:
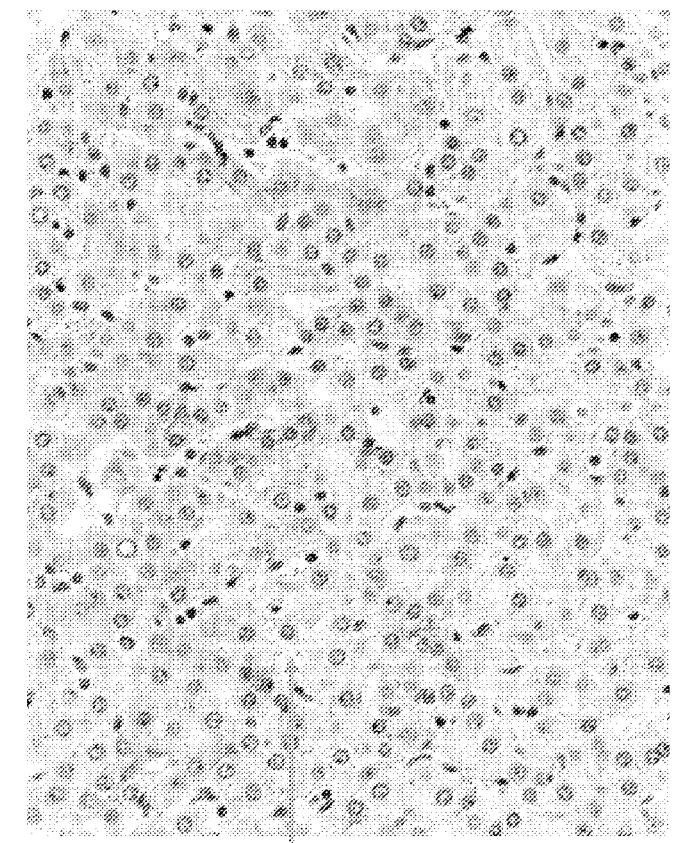
FIGS. 6A-B: Focal staining of hepatocytes in a cirrhotic nodule for GPC3 (Counterstained with hematoxylin; A, ×100; B, ×400).
Figure 6A:

GPC3 immunostaining was positive in all HCC cases and was negative in all dysplastic nodules (20/20 vs 0/7, p<0.001), and normal controls. FIG. 5 displays examples of GPC3 negative staining of cirrhotic tissue and dysplastic nodules, and positive staining for early HCC. The number of cells stained varied from focal areas (focal pattern) to all cells (diffuse pattern). There were several patterns of GPC3 staining: 1. Diffuse staining of the cytoplasm—sometimes accompanied by membranous staining—was more often seen in advanced poorly differentiated HCCs. Nuclear staining was visible only in 2 advanced HCCs, but was also identified in infiltrating inflammatory cells within the tumor; 2. Perinuclear distribution was more frequently noted in the early cases than in advanced cases (7/7 cases vs 4/13 cases); 3. In pseudoglandular HCCs, staining was observed along the apical surface. Stronger staining intensity along canalicular membrane was also seen. A weak focal staining was detected in 7/27 non-tumoral cirrhotic tissues, as shown in FIGS. 6A-B. Overall, there was a significant correlation between the gene expression of GPC3 and the immunostaining status and intensity (Spearman's correlation:0.8, p=0.0001).

Figure 7B:
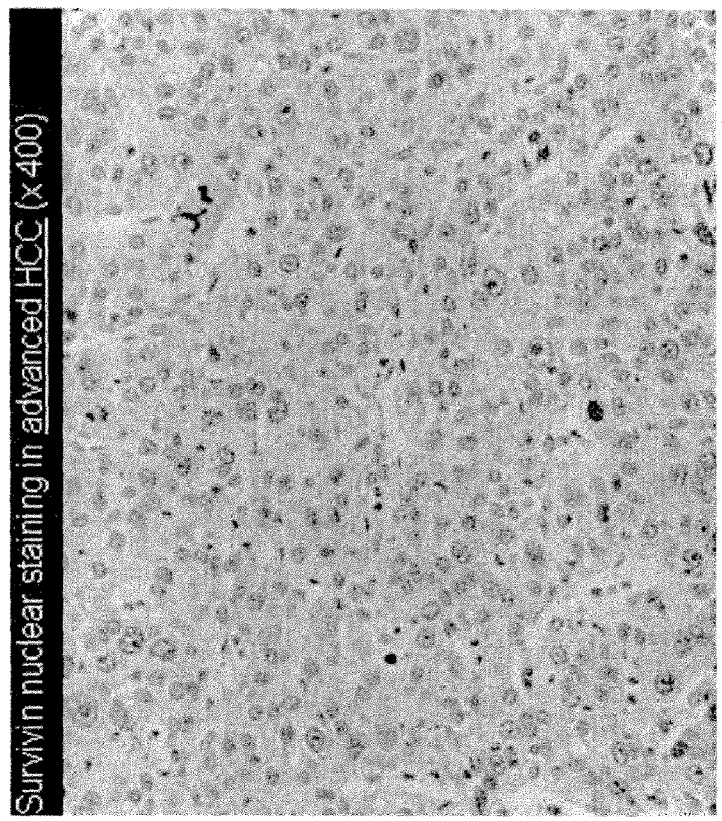
FIGS. 7A-B: Immunostaining for survivin, counterstained with hematoxylin: A. Very early HCC (right) and the surrounding cirrhotic tissue showing diffuse cytoplasmic staining (×100). B. Nuclear staining for survivin is seen in an advanced HCC; the cytoplasm is negative (×400).
Figure 7A:
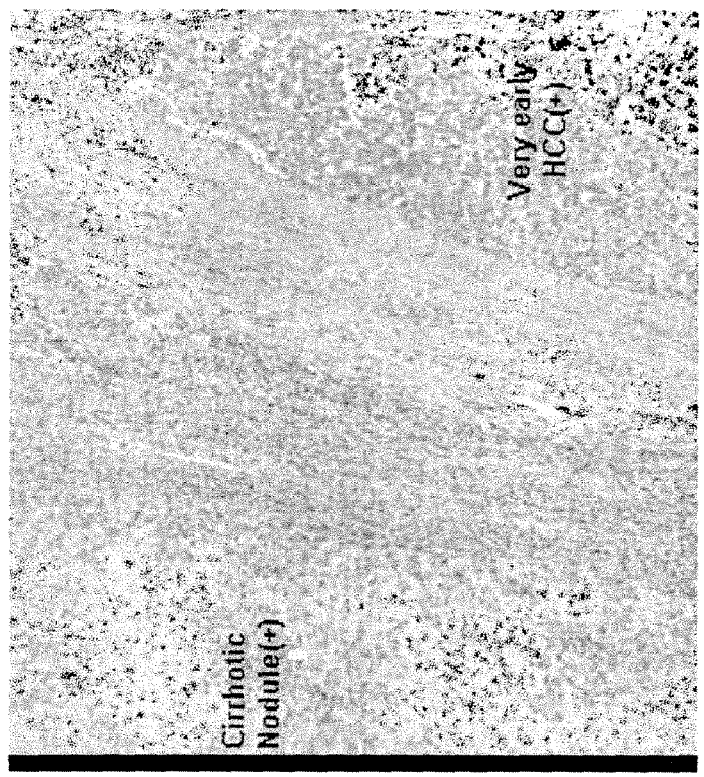

Cytoplasmic survivin staining was negative in the controls and positive in cirrhosis (22/27), dysplastic nodules (6/7) and HCC (19/20) (FIG. 7). There was a trend towards a stronger staining intensity in advanced HCC cases. Significant differences were observed in sub-cellular co-localization: nuclear survivin staining was positive in 12/13 advanced cases compared with 1/7 early case and none of the dysplastic and cirrhotic tissues (p=0.001). The number of positive cells ranged from 1 to >10 per 20× field. Tumor infiltrating inflammatory cells occasionally displayed nuclear staining for survivin. There was a significant correlation between the gene expression of survivin and the subcellular co-localization (positive nuclear staining) (Spearman's correlation: 0.73, p=0.0001).

Discussion

The wide implementation of surveillance programs in cirrhotic patients in the North America and Europe is leading to the detection of small liver nodules of <2 cm in size on which a definitive diagnosis is often difficult to establish. It is expected that this clinical problem will increase in the next 10 years in these regions due to the AASLD and EASL recommendations mandating surveillance by ultrasonography every 6 months in selected cirrhotic patients and other high risk populations (Bruix et al., J. Hepatol., 35:421-430 (2001); Bruix et al., Hepatology, 42:1208-1236 (2005)). As a result, the mean size of the nodules detected is decreasing, resulting in complex recall policies to determine their nature. In cirrhotic livers, only half of nodules of less than 1 cm are ultimately malignant, the proportion increases in nodules of 1-2 cm (Bolondi et al., Gut, 48:251-259 (2001); Tanaka et al., Hepatology, 31:890-898 (2000); O'Malley et al., Am. J. Gastroenterol., 100:1523-1528 (2005)). Pathological differentiation of pre-neoplastic lesions, particularly high grade dysplastic nodules and early HCC is difficult, even for expert hepatopathologists (Kojiro et al., Liver Transpl., 10(2 Suppl 1):S3-S8 (2004)). New advances in imaging techniques enable the characterization of small tumors (<2 cm) as likely HCC (hypervascularization in the arterial phase and wash out in the late phase) in only a small proportion of cases, and additionally require sophisticated radiological equipment and expertise (Bolondi et al., Hepatology, 42:27-34 (2005)).

The present study provides the rationale to use a small group of molecular tissue markers to clarify this situation. To our knowledge, this is the first attempt to devise a molecular model for the diagnosis of small early HCC in HCV patients that is technically simple and applicable in the clinical practice. The 3-gene set signature with highest accuracy includes GPC3, survivin and LYVE1 as the key genes to differentiate dysplastic nodules from early HCC by real time RT-PCR. The accuracy of the model was 94%, and the individual genes showed>2-fold change and an area under the ROC of >0.8. In addition, the study also devises two alternative gene-sets focusing on up-regulated genes that include either GPC3-survivin or GPC3-TERT. To date, solitary genes and molecular indexes have been proposed as markers of HCC. Most of these studies, however, compared gene expression between cirrhotic tissue and cancer, generally at advanced stages, leading to signatures unable to resolve the diagnostic problem. In contrast, we directly compared these two clinically conflicting entities in HCV patients, dysplastic nodules and early cancer. There is an urgent need to distinguish between these two lesions, with major therapeutic implications.

GPC3 is a heparin sulfate proteoglycan previously reported to be up-regulated in HCC in comparison to preneoplastic lesions and cirrhotic tissues at the mRNA (Zhu et al., Gut, 48:558-564 (2001); Hsu et al., Cancer Res., 57:5179-5184 (1997)) and protein levels (Capurro et al., Gastroenterology, 125:89-97 (2003); Yamauchi et al., Mod. Pathol., 18:1591-1598 (2005)). Although its role in the hepatocarcinogenic process is not clear, recent studies suggest that GPC3 promotes the growth of HCC by stimulating the canonical Wnt pathway (Capurro et al., Cancer Res., 65:6245-6254 (2005)). Transcriptional profiles of GPC3 were increased 18-fold in early HCC compared with dysplastic nodules, showing an area under the ROC of 0.84 for HCC diagnosis. Additionally there is a 38-fold increase and 412-fold increase in GPC3 mRNA in early and advanced HCC, respectively, compared to normal tissue. In the immunohistochemical study, GPC3 was very specific for HCC, in concordance with recent studies (Yamauchi et al., Mod. Pathol., 18:1591-1598 (2005)), showing a significant correlation between gene expression and the staining intensity. Unlike previous studies, however, we successfully used a commercially available antibody (monoclonal anti-GPC3 1:50, Zymed Laboratories, South San Francisco, Calif.). Thus, GPC3 is a useful tissue marker both at mRNA and at protein level. However, GPC3 was already up-regulated in non-tumoral cirrhotic tissue (median gene expression 14.8-fold increase compared with control tissue), which translated into a weak focal positive immunostaining in 7/27 cirrhotic tissues analyzed. Although these results do not curtail the utility of GPC3 as a tissue marker, they should be kept in mind when using it as a serum marker in the surveillance setting, as has been proposed in three recent investigations (Capurro et al., Gastroenterology, 125: 89-97 (2003); Nakatsura et al., Biochem. Biophys. Res. Commun., 306:16-25 (2003); Hippo et al., Cancer Res., 64:2418-2423 (2004)).

Survivin is a member of the inhibitor of apoptosis proteins (IAP) family. This molecule is actively suppressed by p53, and has been functionally positioned down-stream of several signaling pathways (Li, Br. J. Cancer, 92:212-216 (2005)). Survivin has been implicated in colorectal, non-small-cell lung and melanoma carcinogenesis (Li, Br. J. Cancer, 92:212-216 (2005)). In HCC, it has been involved in cell proliferation and as an inhibitor of apoptosis (Ito et al., Hepatology, 31:1080-1085 (2000)). Survivin mRNA expression was increased 3.3-fold in early HCC and 24-fold in advanced HCC, compared to normal tissue. In our model, survivin added information to the gene-set of GPC3-LYVE1, despite the fact that the amount of transcript was only slightly increased in early HCC (2.2-fold change; AUC=0.8) compared with dysplastic nodules. We identified a correlation between the level of mRNA expression and sub-cellular localization of the protein, since 12/13 advanced HCC showed positive nuclear staining, a very specific feature. A potential limitation of this marker is that three alternatively spliced transcripts have also been described (survivin-DeltaEx3, survivin 2B and survivin 3B), although survivin wild-type was the most abundant transcript in HCC (Kannangai et al., Int. J. Gastrointest. Cancer, 35:53-60 (2005)).

LYVE1 is a hyaluronan receptor expressed by endothelial cells of normal lymphatic vessels, but not by blood vessels. LYVE-1 is reportedly down-regulated within some solid tumors, such as breast, lung and endometrial cancer, as a result of the destruction of the lymph vessels, whereas its expression is conserved in the tumor periphery (Mouta Carreira et al., Cancer Res., 61:8079-8084 (2001); Colombat et al., J. Pathol., 201:260-267 (2003); Williams et al., J. Pathol., 200:195-206 (2003)). Expression of LYVE1 was previously reported to be down regulated in HCC at the mRNA (Colombat et al., J. Pathol., 201:260-267 (2003)) and protein levels (Mouta Carreira et al., Cancer Res., 61:8079-8084 (2001)). Our data suggests a clear and progressive down regulation of LYVE1 from cirrhosis to HCC. In fact, LYVE1 was 1.6-fold decreased in dysplastic nodules, but 20-fold decreased in early HCC (12-fold change difference; AUC=0.9).

Other genes relevant in our models were TERT and E-cadherin. Activation of TERT is well-documented in early stages of HCC, and it is thought to be required for telomere stabilization and tumor progression (Satyanarayana et al., Hepatology, 40:276-283 (2004)). TERT was clearly upregulated in early HCC (10.8 fold increase compared with dysplastic nodules), and showed an exponential increase in advanced HCC (187-fold increase). One limitation of this marker is the low amount of transcript in early tumors (Cycle 32-34), consistent with the absence of signal/call detected in microarray studies (Wurmbach et al., Proceedings of the AACR, 46:A836 (2005)). Finally, E-cadherin displayed a consistent down-regulation in early tumors, compared with dysplastic nodules (2.8-fold decrease). This protein, which is implicated in the Wnt canonical signaling pathway, is reportedly down-regulated in other cancers, as well as in HCC (Wei et al., Hepatology, 36:692-701 (2002)). Testing the key genes previously reported, as has been done in other neoplasms (Lossos et al., N. Engl. J. Med., 350:1828-1837 (2004)), also enables us to exclude other biomarkers implicated in previous investigations, such as HSP70, STK6, PLA2G13, FLT-3, and AFP.

The novelty of our investigation relies on the identification of a 3 gene-set for the differential diagnosis of small nodules (median size of the early HCCs was of 18 mm, and of dysplastic nodules 10 mm) in HCV-patients. The combined analysis of these genes at the mRNA level provides an accurate, simple and objective diagnosis of the nature of the lesion, applicable in routine clinical use. For that purpose, we used standard commercially available PCR reagents enabling the reproducibility of the results. In addition, we performed an extremely careful pathological examination, dissecting the target lesions from the surrounding tissue and thus enabling the translation in the clinical practice through core biopsies. Finally, we proved that the data generated at early stages is consistent with changes also observed at advanced stages of the disease, where the alterations were much more evident. These advantages make the current investigation unique compared with the signatures reported to date, either using microarray analysis (Paradis et al., Am. J. Pathol., 163:733-741 (2003); Paradis et al., Hepatology, 41:40-47 (2005)) or real time RT-PCR (Nam et al., Hepatology, 42:809-818 (2005)). Smith et al proposed a 50-gene signature to discriminate early HCC and cirrhosis (Paradis et al., Am. J. Pathol., 163:733-741 (2003)); Nam et al reported a 120-gene signature in HBV patients to differentiate dysplastic nodules and HCC (Paradis et al., Hepatology, 41:40-47 (2005)). Finally, Paradis et al reported the first molecular index generated by RT-PCR. In this latter study, the training and testing samples included smaller numbers of dysplastic nodules/small tumors than reported herein, and 13 genes were required to obtain adequate diagnostic accuracies (Nam et al., Hepatology, 42:809-818 (2005)). Despite the adequate sample size, still our training sample might be potentially considered underpowered. However, in our point of view, due to the accuracy of the techniques used, the amount of tissue specimens tested provides a robust data set that is able to consistently identify molecular differences. Before translating the results into clinical practice, however, this gene-set must be tested in a validation set within a prospective surveillance study.

Finally, in parallel to the clinical validation of our gene-set, the search for new and more precise biomarkers must continue. In order to identify new genes or clusters of genes previously implicated in hepatocarcinogenesis or as biomarkers, DNA microarray interrogating the entire human genome and tissue proteomics are the most powerful technologies, and should be thoroughly tested in adequate target lesions and patient populations.

TABLE 1

Genes tested by real-time quantitative RT-PCR (TaqMan) as potential markers of early HCC.

| Name | Symbol | Gene ID | Unigene | GB Accession | Cytoband | TaqMan Assay ID |
|---|---|---|---|---|---|---|
| Postulated as markers of dysplasia or early HCC | | | | | | |
| Telomerase reverse transcriptase | TERT | 7015 | Hs.492203 | NM_003219 | 5p15.33 | Hs00162669_m |
| Fms-related tyrosine kinase 3 | FLT3 | 2322 | Hs.507590 | NM_004119 | 13q12 | Hs00174690_m1 |
| Caveolin 1, caveolae protein, 22kDa | CAV1 | 857 | Hs.74034 | NM_001753 | 7q31.1 | Hs00184697_m1 |

TABLE 1-continued

Genes tested by real-time quantitative RT-PCR (TaqMan) as potential markers of early HCC.

| Name | Symbol | Gene ID | Unigene | GB Accession | Cytoband | TagMan Assay ID |
|---|---|---|---|---|---|---|
| Sema domain, immunoglobulin domain (Ig), short basic domain, secreted, (semaphorin) 3C | SEMA3C | 10512 | Hs.269109 | NM_006379 | 7q21-q31 | Hs00170762_m1 |
| Lymphatic vessel endothelial hyaluronan receptor I, LYVE-1 | XLKD1 | 10894 | Hs.246769 | NM_006691 | 11p15 | Hs00272659_m1 |
| Heat shock 70kDa protein 1-like, HSP70 | HSPA1L | 3305 | Hs.558337 | NM_005527 | 6p21.3 | Hs00271466_s1 |
| Serine/threonine kinase 6 | STK6 | 6790 | Hs.250822 | NM_003600 | 20813.2-q13.3 | Hs00269212 |
| Glypican 3 | GPC3 | 2719 | Hs.356794 | NM_004484 | Xq26.1 | Hs00170471_m1 |
| Phospholipase A2, group XIIB | PLA2G12B | 84647 | Hs.333175 | NM_032562 | 10822.1 | Hs00261432 |
| Plasma glutamate carboxypeptidase | PGCP | 10404 | Hs.156178 | NM_016134 | 8q22.2 | Hs00255440_m1 |
| Cell cycle regulation | | | | | | |
| Tumor protein p53 (Li-Fraumeni syndrome) | TP53 | 7157 | Hs.408312 | NM_000546 | 17p13.1 | Hs00153340_m1 |
| Cyclin-dependent kinase inhibitor 2A (melanoma, p16, inhibits CDK4) | CDKN2A | 1029; 51198 | Hs.512599 | NM_000077 | 9p21 | Hs00233365_m1 |
| Cyclin-dependent kinase inhibitor 1B (p27, Kip1) | CDKN1B | 1027 | Hs.238990 | NM_004064 | 12p13.1-p12 | Hs00153277_m1 |
| Cyclin D1 | CCND1 | 595 | Hs.523852 | NM_053056 | 11q13 | Hs00277039_m1 |
| Retinoblastoma 1 (including osteosarcoma) | RB1 | 5925 | Hs.408528 | NM_000321 | 13q14.2 | Hs00153108_m1 |
| Gankyrin. Proteasome 26S subunit, non-ATPase, 10 | PSMD10 | 5716 | Hs.522752 | NM_170750 | Xq22.3 | Hs00829508_s1 |
| Survivin | BIRC5 | 332; 8475 | Hs.514527 | NM_001168 | 17q25 | Hs00153353_m1 |
| Signal transduction pathways | | | | | | |
| Catenin (cadherin-associated protein), beta 1, 88kDa | CTNNB1 | 1499 | Hs.476018 | NM_001904 | 3p21 | Hs00170025_m1 |
| Cadherin 1, type 1, E-cadherin (epithelial) | CDH1 | 999 | Hs.461086 | NM_004360 | 16822.1 | Hs00170423 |
| Axin 1 | AXIN1 | 8312 | Hs.512765 | NM_181050 | 16p13.3 | Hs00394718_m1 |
| Frizzled homolog 7 (Drosophila) | FZD7 | 8324 | Hs.173859 | NM_003507 | 2q33 | Hs00275833_m1 |
| V-myc myelocytomatosis viral oncogene homolog (avian), c-myc | MYC | 4609 | Hs.202453 | NM_002467 | 8q24.12-q24.13 | Hs00153408_m1 |
| Transforming growth factor, beta 1 | TGFB1 | 7040 | Hs.1103 | NM_000660 | 19q13.2 | Hs0171257 |
| SMAD, mothers against DPP homolog 2 | SMAD2 | 4087 | Hs.465061 | NM_005901 | 18q21.1 | Hs00183425_m1 |
| Paternally expressed 10 | PEG10 | 23089 | Hs.147492 | XM_496907 | 7q21 | Hs00248288 |
| Suppressor of cytokine signaling 1 | SOCS1 | 8651 | Hs.50640 | NM_003745 | 16p13.13 | Hs00705164_s1 |
| Ethylmalonic encephalopathy 1 | ETHE1 | 23474 | Hs.7486 | NM_014297 | 19q13.31 | Hs00204752_m1 |
| Phosphatase and tensin homolog 1 | PTEN | 5728 | Hs.500466 | NM_000314 | 10823.3 | Hs00829813_s1 |
| Growth factors and receptors | | | | | | |
| Insulin-like growth factor 2 (somatomedin A) | IGF2 | 3481;492304 | Hs.523414 | NM_000612 | 11p15.5 | Hs00171254_m1 |
| Mannose-6-phosphate receptor (cation dependent) | M6PR | 4074 | Hs.134084 | NM_002355 | 12p13 | Hs00158987_m1 |
| Insulin-like growth factor binding protein 3 | IGFBP3 | 3486 | Hs.450230 | NM_000598 | 7p13-p12 | Hs00426287_m1 |
| Platelet-derived growth factor receptor, alpha polypeptide | PDGFRA | 5156 | Hs.74615 | NM_006206 | 4q11-q13 | Hs00183486_m1 |
| Fibroblast growth factor 2 (basic) | FGF2 | 2247 | Hs.284244 | NM_002006 | 4q26-q27 | Hs00266645_m1 |
| Hepatocyte growth factor (hepapoietin A; scatter factor) | HGF | 3082 | Hs.396530 | NM_000601 | 7q21.1 | Hs00300159_m1 |
| Met proto-oncogene (hepatocyte growth factor receptor) | MET | 4233 | Hs.132966 | NM_000245 | 7q31 | Hs00179845_m1 |
| Epidermal growth factor (beta-urogastrone) | EGF | 1950 | Hs.419815 | NM_001963 | 4q25 | Hs00153181_m1 |
| Epidermal growth factor receptor (erythroblastic leukemia viral (v-erb-b) oncogene homolog, avian) | EGFR | 1956 | Hs.488293 | NM_005228 | 7p12 | Hs00193306_m1 |
| Transforming growth factor, alpha | TGFA | 7039 | Hs.170009 | NM_003236 | 2p13 | Hs00177401_m1 |
| Angiogenesis, matrix degradation and invasion | | | | | | |
| Vascular endothelial growth factor | VEGF | 7422 | Hs.73793 | NM_003376 | 6p12 | Hs00173626_m1 |
| Kinase insert domain receptor (a type III receptor tyrosine kinase) | KDR | 3791 | Hs.479756 | NM_002253 | 4q11-q12 | Hs00176676_m1 |
| Inhibin, beta A (activin A, activin AB alpha polypeptide | INHBA | 3624 | Hs.28792 | NM_002192 | 7p15-p13 | Hs00170103 |
| Angiopoietin 2 | ANGPT2 | 285 | Hs.553484 | NM_001147 | 8p23.1 | Hs00169867_m1 |
| Non-metastatic cells 1, protein (NM23A) expressed in | NME1 | 4830; 4831 | Hs.118638 | NM_000269 | 17q21.3 | Hs00264824_m1 |
| Ras homolog gene family, member C | RHOC | 389 | Hs.502659 | NM_175744 | 1p13.1 | Hs00733980_m1 |
| CD82 antigen, Kangai 1 | KAI1 | 3732 | Hs.527778 | NM_002231 | 11p11.2 | Hs00174463_m1 |
| Matrix metallopeptidase 9 (gelatinase B, 92kDa gelatinase, 92kDa type IV collagenase) | MMP9 | 4318 | Hs.297413 | NM_004994 | 20q11.2-q13.1 | Hs00234579_m1 |
| Matrix metallopeptidase 14 (membrane-inserted) | MMP14 | 4323 | Hs.2399 | NM_004995 | 14q11-q12 | Hs00237119_m1 |

TABLE 1-continued

Genes tested by real-time quantitative RT-PCR (TaqMan) as potential markers of early HCC.

| Name | Symbol | Gene ID | Unigene | GB Accession | Cytoband | TaqMan Assay ID |
|---|---|---|---|---|---|---|
| Topoisomerase (DNA) II alpha 170kDa | TOP2A | 7153 | Hs.156346 | NM_001067 | 17q21-q22 | Hs00172214_m1 |
| Secreted phosphoprotein 1 (osteopontin, bone sialoprotein I, early T-lymphocyte activation 1) | SPP1 | 6696 | Hs.313 | NM_000582 | 4q21-q25 | Hs00167093_m1 |
| Others | | | | | | |
| Retinoid X receptor, alpha | RXRA | 6256 | Hs.20084 | NM_002957 | 9q34.3 | Hs00172565 |
| Hypoxia-inducible factor 1, alpha subunit (basic helix-loop-helix transcription factor) | HIF1A | 3091 | Hs.509554 | NM_181054 | 14q21-q24 | Hs00153153_m1 |
| Serine/threonine kinase 11 (Peutz-Jeghers syndrome) | STK11 | 6794 | Hs.515005 | NM_000455 | 19p13.3 | Hs00176092_m1 |
| Kruppel-like factor 6 | KLF6 | 1316 | Hs.4055 | NM_001300 | 10p15 | Hs00154550_m1 |
| Alpha-fetoprotein | AFP | 174 | Hs.518808 | NM_001134 | 4q11-q13 | Hs00173490_m1 |

TABLE 2

Main characteristics of the 20 HCV-cirrhotic patients with early HCC

| | |
|---|---|
| Age (yr, mean + SD) | 62 ± 9.4 |
| Sex (Male /Female) | 16/4 |
| Race (White/Afro-American/Asian) | 18/1/1 |
| Ethnicity (Hispanic/Non-Hispanic) | 7/13 |
| Child-Pugh (A/B-C) | 15/5 |
| Treatment | |
| Surgical resection | 15 |
| Liver transplantation | 5 |
| Pathological characteristics | 10 |
| Group: Very early HCC* | 10 |
| Early HCC | 21.8 ± 10.8 |
| Size (mm, mean + SD) | 14 |
| Maximum diameter ≦2 cm | 6 |
| >2 cm | 15/5 |
| Differentiation degree (well/moderately) | 2/18 |
| Microscopic vascular invasion (yes/no) | 2/18 |
| Satellites (yes/no) | 2/18 |

*Very early HCC was defined as a solitary well-differentiated tumor less than 2 cm in diameter without vascular invasion/satellites.

TABLE 3

Genes significantly dysregulated in early HCC.*

| Genes | Dysplastic (n = 17) | Early HCC (n = 20) | Auc** | P |
|---|---|---|---|---|
| Up-regulated (n = 5) | | | | |
| Telomerase reverse transcriptase: TERT | 3.5 (0.1-36) | 38 (4.7-382) | 0.92 | .0001 |
| Glypican-3: GPC3 | 2 (0.4-24) | 36.6 (0.3-578) | 0.84 | .001 |
| Gankyrin: PSMD10 | 1.1 (0.5-2.3) | 2.6 (0.4-4.7) | 0.82 | .0001 |
| Survivin: BIRC5. | 1.5 (0.7-6.2) | 3.3 (0.8-23.5) | 0.80 | .002 |
| Topoisomerase II: TOP2A | 2.1 (0.9-7.3) | 6.5 (0.5-59) | 0.85 | .0001 |
| Down-regulated (n = 7) | | | | |
| Lymphatic Vessel endothelial hyaluronan 1 (LYVE1): XLKD1 | 0.6 (0.1-1.8) | 0.05 (0.01-0.3) | 0.90 | .0001 |
| E-cadherin: CDH1 | 2.2 (1.1-5) | 0.8 (0.2-3.9) | 0.84 | .0001 |
| Insulin-like growth factor binding protein-3: IGFBP3 | 1.7 (0.6-3) | 0.2 (0.02-1.7) | 0.85 | .0001 |
| Platelet-derived growth factor receptor-A: PDGFRA | 1.8 (0.5-6.3) | 0.2 (0.02-1.7) | 0.85 | .0001 |
| Transforming growth factor-alpha: TGFA | 1.2 (0.5-2.3) | 0.3 (0.06-1.3) | 0.86 | .0001 |
| Cyclin D1: CCND1 | 2.8 (1.3-6.1) | 1.6 (0.6-13) | 0.91 | .0001 |
| Hepatocyte growth factor: HGF | 1.3 (0.6-2.4) | 0.3 (0.04-2.1) | 0.90 | .0001 |

*Gene expression is presented as fold-changes considering gene expression in normal tissue = 1. Results are presented as median (95 percent confidence interval). All genes showed significant dys-regulation by Mann-Whitney test, >2-fold change in HCC compared with dysplasia and AUC > 0.80.

**AUC = Area under the ROC curve.

TABLE 4

Accuracy of the models

| Models tested | Early HCC (n = 20) | Dysplastic nodule (n = 17) | Accuracy Overall | S/Sp | PPV/NPV | LR |
|---|---|---|---|---|---|---|
| Combination of 3 de-regulated genes : | | | | | | |
| 1. LYVE1, Glypican-3, Survivin | | | 94.6% | 95%/94% | 95%/94% | 16 |
| Predicted: Early HCC | 19 | 1 | | | | |
| No HCC | 1 | 16 | | | | |
| 2. LYVE1, Survivin, E-cadherin | | | 94.6% | 90%/100% | 100%/89% | —* |
| Predicted: Early HCC | 18 | 0 | | | | |
| No HCC | 2 | 17 | | | | |
| Combination of 2 up-regulated genes: | | | | | | |
| 1. Glypican-3, Survivin | | | 92% | 100%/82% | 86%/100% | 5.8 |
| Predicted: Early HCC | 20 | 3 | | | | |
| No HCC | 0 | 14 | | | | |
| 2. Glypican-3, TERT | | | 92% | 95%/88% | 90%/93% | 8.6 |
| Predicted: Early HCC | 19 | 2 | | | | |
| No HCC | 1 | 15 | | | | |

S = Sensitivity;

Sp = specificity;

PPV = positive predictive value;

NPV = negative predictive value;

LR = Likelihood ratio for a positive result.

*LR can not be calculated, zero denominator.

TABLE 5

Gene transcriptional profiles of the 5 key genes selected in the models [Glypican-3, Survivin, LYVE1, TERT and E-cadherin] tested in cirrhosis, dysplastic nodules, early and advanced HCC*.

| Genes | Cirrhosis (n = 10) | Dysplastic (n = 17) | Early HCC (n = 20) | Advanced HCC (n = 20) |
|---|---|---|---|---|
| Glypican-3 (GPC3) | 14.8 (5.1-118) | 2 (0.4-24) | 36.6 (0.3-578) | 412 (1-2364) |
| TERT | 1.8 (0.7-13) | 3.5 (0.1-36) | 38 (4.7-382) | 187 (0.8-2277) |
| Survivin (BIRC5) | 2.6 (1.5-4.2) | 1.5 (0.7-6.2) | 3.3 (0.8-23.5) | 24 (1.6-122) |
| LYVE1 (XLKD1) | 0.9 (0.4-1.5) | 0.6 (0.1-1.8) | 0.05 (0.01-0.3) | 0.08 (0.01-0.32) |
| E-cadherin (CDH1) | 3.9 (2-8) | 2.2 (1.1-5) | 0.8 (0.2-3.9) | 0.8 (0.3-3.2) |

*Gene expression is presented as fold-changes considering gene expression in normal tissue = 1. Results are presented as median (95 percent confidence intervals)

TABLE 6

Results of immunostaining for Glypican-3 and survivin in 57 samples, and correlation with gene expression profiles*.

| | Controls (n = 3) | Cirrhosis (n = 27) | Dysplastic (n = 7) | HCC Early (n = 7) | HCC Advanced (n = 13) |
|---|---|---|---|---|---|
| Glypican-3 | | | | | |
| mRNA (fold-changes)* | 1.3 (0.6-1.5) | 16 (5-118) | 1.2 (0.4-2.7) | 99(0.4-578) | 592 (16-2364) |
| Staining Intensity | | | | | |
| Negative | 3 | 20 | 7 | 0 | 0 |
| Positive | 0 | 7 | 0 | 7*** | 13 |
| (+) | 0 | 7 (patchy)* | 0 | 3 | 3 |
| (++) | 0 | 0 | 0 | 4 | 5 |
| (+++) | 0 | 0 | 0 | 0 | 5 |
| Localization | | | | | |
| Focal | — | 7 | — | 5 | 3 |
| Diffuse | — | — | — | 2 | 10 |

TABLE 6-continued

Results of immunostaining for Glypican-3 and survivin in 57 samples, and correlation with gene expression profiles*.

|  | Controls (n = 3) | Cirrhosis (n = 27) | Dysplastic (n = 7) | HCC Early (n = 7) | HCC Advanced (n = 13) |
|---|---|---|---|---|---|
| Survivin |  |  |  |  |  |
| mRNA (fold-changes)* | 0.7 (0.5-2.7) | 2.5 (1.5-4.5) | 1.6 ( 1-2.8) | 4.7(1.6-10.5) | 30 (8.3-122) |
| Staining Intensity |  |  |  |  |  |
| Negative | 3 | 5 | 1 | 0 | 1 |
| Positive | 0 | 22 | 6 | 7 | 12 |
| (+) | 0 | 10 | 5 | 3 | 3 |
| (++) | 0 | 12 | 1 | 4 | 4 |
| (+++) | 0 | 0 | 0 | 0 | 5 |
| Sub-cellular localization |  |  |  |  |  |
| Cytoplasm | — | 22 | 6 | 5 | 0 |
| Cytoplasm&nucleus | — | 0 | 0 | 0 | 5# |
| Nucleus | — | 0 | 0 | 1 | 7# |

Positive immunostaining: + = weak, +++ moderate and +++ = strong.
*Gene expression was available in 3 controls, 9 cirrhotic tissue, 7 dysplastic nodules and 20 HCCs.
Expressed as fold-changes, median (95% confidence interval).
**Patchy GPC3 staining in 7 cases in cirrhotic tissue
***GPC3 staining : Dysplastic vs early p = 0.0001
Survivin nuclear staining was present in 12/13 advanced HCC vs 0/7 dysplastic and 1/7 early HCC (p = 0.001)

The invention claimed is:

1. A method of determining whether a patient is afflicted with hepatocellular carcinoma (HCC), the method comprising:
    a) determining the level of expression of at least two markers in a patient sample comprising a liver nodule two centimeters or less in diameter, wherein the markers are selected from the group consisting of GPC3, survivin and LYVE1;
    b) determining the level of expression of the markers in a control sample;
    c) comparing the level of expression of each of the markers in the patient sample and in the control sample; and
    d) identifying the patient as being afflicted with HCC when there is a difference between the level of expression of the markers in the patient sample and the control sample, thereby determining whether the patient is afflicted with HCC.

2. The method of claim 1, wherein the level of expression from a control sample is determined by a method selected from:
    a) a level determined from liver cells from the patient which are non-cancerous;
    b) a level determined from liver cells from a subject having benign dysplasia or normal tissue; and
    c) a predetermined level using an average of the levels of expression from a population of subjects having benign dysplastic nodules or normal liver cells.

3. The method of claim 1, wherein the markers correspond to a secreted protein.

4. The method of claim 1, wherein the markers comprise transcribed polynucleotides or portions thereof.

5. The method of claim 3, wherein the presence of the markers are detected using reagents which specifically bind with the markers.

6. The method of claim 5, wherein the reagents are each selected from the group consisting of an antibody, and an antibody fragment.

7. The method of claim 4, wherein detecting the transcribed polynucleotides comprises amplifying the transcribed polynucleotides.

8. The method of claim 4, wherein the levels of expression of the markers in the patient sample are determined by detecting the presence in the patient sample of a transcribed polynucleotide which anneals with at least one of the markers or a portion thereof under stringent hybridization conditions comprising 42° C. in a hybridization solution comprising 50% formamide, 1% SDS, 1M NaCl, and 10% dextran sulfate followed by washing twice for 30 minutes at 60° C. in a wash solution comprising 0.1×SSC and 1% SDS.

9. The method of claim 1, wherein the level of expression of at least one of the markers in the patient sample differs from the level of expression of that marker in the control sample by a factor of at least 2.

10. The method of claim 1, wherein said patient is identified as having HCC when said patient sample comprises up-regulation of GPC3 and survivin.

11. The method of claim 1, wherein said patient is identified as having HCC when said patient sample comprises a down-regulation of LYVE1.

12. The method of claim 1, wherein said method further comprises identification of the patient as having HCC when said patient sample comprises a down-regulation of LYVE1.

13. The method of claim 1, wherein said at least two markers are GPC3 and LYVE1.

14. The method of claim 1, wherein the expression of the markers is determined by using real-time RT-PCR.

15. The method according to claim 1 wherein the patient sample liver nodule is 1.5 centimeters or less in diameter.

16. The method according to claim 15 wherein the patient sample liver nodule is 1.2 centimeters or less in diameter.

17. A method for monitoring the progression of HCC in a patient, the method comprising:
 a) determining the level or expression of at least two markers in a patient sample comprising a liver nodule two centimeters or less in diameter from a first point in time, wherein the markers are selected from the group consisting of GPC3, survivin and LYVE1;
 b) determining the level of expression of the markers in a sample comprising a liver nodule of any size from the patient at a subsequent point in time; and
 c) comparing the levels of expression detected in steps a) and b), thereby monitoring the progression of HCC in the patient, wherein a change in expression of the markers is indicative of either progression or regression of HCC.

* * * * *